(12) United States Patent
Endl et al.

(10) Patent No.: US 8,354,516 B2
(45) Date of Patent: Jan. 15, 2013

(54) POLYPEPTIDE PRODUCING CELLS

(75) Inventors: Josef Endl, Weilheim (DE); Erhard Kopetzki, Penzberg (DE); Oliver Ploettner, Munich (DE); Ursula Schwarz, Bichl (DE); Georg Tiefenthaler, Sindelsdorf (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 196 days.

(21) Appl. No.: 12/299,918

(22) PCT Filed: May 15, 2007

(86) PCT No.: PCT/EP2007/004313
§ 371 (c)(1),
(2), (4) Date: Nov. 7, 2008

(87) PCT Pub. No.: WO2007/131774
PCT Pub. Date: Nov. 22, 2007

(65) Prior Publication Data
US 2009/0311725 A1 Dec. 17, 2009

(30) Foreign Application Priority Data
May 17, 2006 (EP) .................................... 06010146

(51) Int. Cl.
*C07H 21/04* (2006.01)
*C12N 15/00* (2006.01)
(52) U.S. Cl. .................................. 536/23.53; 435/320.1
(58) Field of Classification Search ........................ None
See application file for complete search history.

(56) References Cited

U.S. PATENT DOCUMENTS 7,741,465 B1 * 6/2010 Eshhar et al. ................ 536/23.4

FOREIGN PATENT DOCUMENTS

| WO | WO 01/92291 | 12/2001 |
| WO | WO 2005/040213 | 5/2005 |
| WO | WO 2005/089285 | 9/2005 |

OTHER PUBLICATIONS

Harris C L et al: Jour. of Immunological AMethods, 268:2 (2002) 245-258 XP004379155.
Zhu Y et al, Molecular Therapy, 4:4 (2001) 375-3382 XP002992774.
European Search Report dated Sep. 28, 2010.
Prochownik E V et al, *Jour. of Biological Chem*, 259:24 (1984) 15386-15392.
Nussaume L et al, *Molecular and General Genetics*, 249:1 (1995) 91-101.
Modrek B et al *Nucleic Acids Research*, 29:13 (2001) 285-2859 XP002403630.
Danner D et al, *Proceedings of the Nat'l Acad of Sci of the USA*, 82:24 (1985) 8658-8662 XP002403631.
Yu, Q. and Toole, B.P. et al., *Journal Biological Chemistry 271*:20603-20607 ( 1996).
Ernst, L.K. et al., *Mol. Immunology* 35:943-954 ( 1998).
Tang, W et al., *PNAS USA* 97:6025-6030 ( 2000).
(*Translation of Japanese Office Action in Corres. Appl. 2009-510343* Jul. 20, 2011).

* cited by examiner

*Primary Examiner* — Michael Burkhart
(74) *Attorney, Agent, or Firm* — George W. Johnston; Dennis P. Tramaloni; Brian C. Remy

(57) ABSTRACT

The current invention describes a nucleic acid comprising in a 5' to 3' direction a) a first nucleic acid encoding a heterologous polypeptide without an in frame stop codon, b) a second nucleic acid beginning with a 5' splice donor site and terminated by a 3' splice acceptor site comprising an in frame translational stop codon and a polyadenylation signal, and c) a nucleic acid encoding i) at least a fragment of a transmembrane domain, or ii) a signal peptide for a GPI-anchor.

12 Claims, 10 Drawing Sheets

SEQUENCE LISTING

<160> NUMBER OF SEQ ID NOS: 176

<210> SEQ ID NO 1
<211> LENGTH: 2767
<212> TYPE: DNA
<213> ORGANISM: Homo sapiens

```
<400> SEQUENCE: 1
gtgagtcacc cccaggccca gggttgggac ggggactctg aggggggcca taaggagctg        60
gaatccatac taggcagggg tgggcactgg gcagggcgg ggctaggctg tcctgggcac        120
acaggcccct tctcggtgtc cggcaggagc acagacttcc cagtactcct gggccatgga      180
tgtcccagcg tccatccttg ctgtccacac cacgtgctgg cccaggctgg ctggcacagt      240
gtaagaggtg gatacaaccc ctcgccgtgc cctgaggagt ggcggtttcc tcccaagaca      300
ttccccacgg ctgggtgctg ggcacaggcc ttccctggtg tgaccgtgaa tgtggtcacc      360
ctgaacagct gccctctctg gggacatctg actgtccaag accacagtca gcacctctgg      420
gagccagagg ggtctccaga gaccccccaga tgtcaggctt gggctcagtg cccagcgaaa      480
ggtcagcccc acacatgccc ataatgggcg cccacccaga gtgacagccc ccagcctcct      540
gccaggccca cccttttccg cccccttgag gcatggcaca cagaccagtg cgcccactgc      600
ccgagcatgg ccccagtggg atgtggtggc cacgaggggc tgtacacaca gcaggaggct      660
gtccgccctg ctcagggcct gctgcctatg ccccagctgt ccaaccaagg gaggcatgga      720
agggcccctg gtgtaagctg gagccaggca cccaggcccc cggccaccct gcagagccaa      780
ggaaaggaag acacccaagt caacaagggg cagggctgag ggctgtccca ggctcttttg      840
gcccgagggg ctgccagcag ccctgacccg gcatgggcct tccccaaaag cgaccctgtg      900
aggtggcctc acagagaacc ccctctgagg acagtgtctg accctgcctg cctcacacag      960
atgggcccca cagcagtggg caacctgggg ggcagcagcc caacctgacc ctgcagggac     1020 tgcccctgc agcagcagct gcttctcagt ccccaacct cctgtcccc gccagagggt       1080 cttcccgaa gctgcagccc caacccatgg ctgcccacct ggaaccggga ctccctgtcc     1140 actgcccct cccttcggg gccccatctg tgctggggcc caggttcggc ctacagattc       1200
ccatcattgc catggcctcc tgaccttgcc tatccacccc caaccaccgg ctccatgctg     1260
accctccccc aggctcccac gcccagctgg ccggccatcc ccaggcacag acagtctggg     1320
atctcacagg ttagcctgga ccatccacct ggccagacct gggagaggct ggaagctgcc     1380
ctgccaccat gctccagggc cccaggttgc agtactatgg ggtgagggtg tgtgtgcaca     1440
cctgtgtgta cctaggatat ccgagtgtac ccttgtgccc ccaagcacaa gtctccctcc     1500
caggcagtga ggcccagatg gtgcagtggt tagagctgag gcttatccca cagagaaccc     1560
tggcgccttg gtcaaggaag cccctatgcc tttcttgcct cgatttcccc tcttgtctgc     1620
tgagccagca ggggccacgt cctgggctgc tgtgaggagg aagcaagttg gtgctaggag     1680
gggctcctgt gtgtgcatgg gcgggagggg tgcaggtatc tgagcacccc ggtctccact     1740
tgagagagca gggcaggagc tccctgaccc acccagacta cacacgctgt gtccacgtgt     1800
ctcccattat ctgtggcaga ggatccggct tctttctcaa tttccagttc ttcacaaagc     1860
aatgcctttg taaaatgcaa taagaaatac tagaaaaatg atatgaacag aaagacacgc     1920 cgatttttg ttattagatg taacagacca tggccccatg aaatgatccc ggaccagatc     1980
cgtccacacc cgccactcag cagctctggc cgagctcaca gtacaaccac aataaactct     2040
tgttgaatga actctaggaa gtctgtgacg tggctggttc ttgtcaatgc ttcctgcctg     2100
cccacaggct cttcctcgtg gatggggctg tgcttgccac ggaagcgcgt ttttcccggc     2160
ctaggcttgc cttgggcccc actgccgtct ccagctggag atgaccttct atacacacat     2220
ttgctcatga cagaccctcg cttagccccc ttcatggct ccctcctgct gctgggataa       2280
aatcaccttg cctggatatc ccctcctggg cccctttcca ccctccttag tcagcacccc     2340
```

-continued

| | |
|---|---|
| cagttcaggg cacctgcttt ccccgctgcg gagaagccac tctctccttg ctgcccggct | 2400 |
| gtgtcttgcc ttccacacct tgtcacagtg gccacttcct aaggaaggcc tccctgtgtg | 2460 |
| caggtgtgca gaagtgcccc agcctcccgt cacctttgtc acgggagccc aatccatgag | 2520 |
| agtctatggt tctgtctgtc tgccccactc agggcagcga caagtccagg cggggaggac | 2580 |
| acagtaggca gagatttgtc gaggggacat atgagcaaga gggtgaggct gggagctccc | 2640 |
| tggagataac cacgcctcct gggaagactc gccgtcattt cagctccacg ctgtgcgggg | 2700 |
| gtgggtggag gggtagcctg gccctcatga ccagggagct tctcactcag ccctgttcc | 2760 |
| tccccag | 2767 |

<210> SEQ ID NO 2
<211> LENGTH: 1287
<212> TYPE: DNA
<213> ORGANISM: Homo sapiens

<400> SEQUENCE: 2

| | |
|---|---|
| gtaaatgagt gccacggccg gcaagccccc gctccccagg ctctcggggt cgcgcgagga | 60 |
| tgcttggcac gtaccccgtg tacatacttc ccaggcaccc agcatggaaa taaagcaccc | 120 |
| agcgcttccc tgggcccctg cgagactgtg atggttcttt ccacgggtca ggccgagtct | 180 |
| gaggcctgag tggcatgagg gaggcagagt gggtcccact gtccccacac tggcccaggc | 240 |
| tgtgcaggtg tgcctgggcc gctagggtg gggctcagcc aggggctgcc ctcggcaggg | 300 |
| tgggggattt gccagcgtgg ccctccctcc agcagcagct gccctgggct gggccacgag | 360 |
| aagccctagg agccctggg gacagacaca cagcccctgc ctctgtagga gactgtcctg | 420 |
| ttctgtgagc gccctgtcct ccgacccgca tgcccactcg ggggcatgcc tagtccatgt | 480 |
| gcgtagggac aggccctccc tcacccatct acccccacgg cactaacccc tggcagccct | 540 |
| gcccagcctc gcaccgcat ggggacacaa ccgactccgg ggacatgcac tctcgggccc | 600 |
| tgtggagaga ctggtccaga tgcccacaca cacactcagc ccagacccgt tcaacaaacc | 660 |
| ccgcactgag gttggccggc cacacggcca ccacacacac acgtgcacgc ctcacacacg | 720 |
| gagcctcacc cgggcgaacc gcacagcacc cagaccgag caaggtcctc gcacacgtga | 780 |
| acactcctcg gacacaggcc cccacgagcc ccacgcggca cctcaaggcc cacgagccgc | 840 |
| tcggcagctt ctccacatgc tgacctgctc agacaaaccc agccctcctc tcacaaggtg | 900 |
| cccctgcagc cgccacacac acacagggga tcacacacca cgtcacgtcc ctggccctgg | 960 |
| cccacttccc agtgccgccc ttccctgcag ctggggtcac atgaggtgtg gcttcacca | 1020 |
| tcctcctgcc ctctgggcct cagggaggga cacgggagac ggggagcggg tcctgctgag | 1080 |
| ggccaggtcg ctatctaggg ccgggtgtct ggctgagccc cggggccaaa gctggtgccc | 1140 |
| agggcgggca gctgtgggga gctgacctca ggacattgtt ggcccatccc ggccgggccc | 1200 |
| tacatcctgg gtcctgccac agagggaatc cccccagag gcccaagccc aggggacac | 1260 |
| agcactgacc accccctcc tgtccag | 1287 |

<210> SEQ ID NO 3
<211> LENGTH: 1301
<212> TYPE: DNA
<213> ORGANISM: Homo sapiens

<400> SEQUENCE: 3

| | |
|---|---|
| gtaaatgagt gccacggccg gcaagccccc gctccccagg ctctcggggt cgcgcgagga | 60 |
| tgcttggcac gtaccccgtc tacatacttc ccgggcaccc agcatggaaa taaagcaccc | 120 |

-continued

| | |
|---|---|
| agcgctgccc tgggcccctg cgagactgtg atggttcttt ccgtgggtca ggccgagtct | 180 |
| gaggcctgag tggcatgagg gaggcagagc gggttccact gtccccacac tggcccaggc | 240 |
| tgtgcaggtg tgcctgggcc gcctagggtg gggctcagcc aggggctgcc ctcggcaggg | 300 |
| tgggggattt gccagcgtgg ccctccctcc agcagcagct gccctgggct gggccacggg | 360 |
| aagccctagg agccctgggg acagacaca cagccctgc ctctgtagga gactgtcctg | 420 |
| tcctgtgagc gccctgtcct ccgacctcca tgcccactcg ggggcatgcc tagtccatgt | 480 |
| gcgtagggac aggccctccc tcacccatct accccacgg cactaacccc tggctgccct | 540 |
| gcccagcctc gcaccgcat ggggacacaa ccgactccgg ggacatgcac tctcgggccc | 600 |
| tgtggaggga ctggtccaga tgcccacaca cacactcagc ccagacccgt caacaaacc | 660 |
| ccgcgctgag gttggccggc cacacggcca ccacacacac acgtgcacgc ctcacacacg | 720 |
| gagcctcacc cgggcgaacc gcacagcacc cagaccagag caaggtcctc gcacacgtga | 780 |
| acactcctca gacacaggcc cccacgagcc ccacgcggca cctcaaggcc cacgagccgc | 840 |
| tcggcagctt ctccacatgc tgacctgctc agacaaaccc agccctcctc tcacaaggtg | 900 |
| cccctgcagc cgccacacac acacaggccc ccacacacag gggaacacac gccacgtcgc | 960 |
| gtccctggca ctggcccact tcccaatgcc gccctcccct gcagctgagg tcacatgagg | 1020 |
| tgtgggcttc accatcctcc tgccctctgg gcctcaggga gggacacagg agatggggag | 1080 |
| cgggtcctgc tgagggccag gtcgctatct agggctgggt gtctggctga gtcccggggc | 1140 |
| caaagctggt gccagggca ggcagctgtg gggagctgac ctcaggacac tgttggccca | 1200 |
| tcccggccgg gccctacatc ctgggtcctg ccacagaggg aatcaccccc agaggcccga | 1260 |
| gcccagcagg acacagtatt gaccacccac ttcctgtcca g | 1301 |

<210> SEQ ID NO 4
<211> LENGTH: 1914
<212> TYPE: DNA
<213> ORGANISM: Homo sapiens

<400> SEQUENCE: 4

| | |
|---|---|
| gtaaacccac cctgtacaac gtgtccctgg tcatgtccga cacagctggc acctgctact | 60 |
| gaccctgctg gcctgcccac aggctcgggg cggctggccg ctctgtgtgt gcatgcaaac | 120 |
| taaccgtgtc aacggggtga gatgttgcat cttataaaat tagaaataaa aagatccatt | 180 |
| caaaagatac tggtcctgag tgcacgatgc tctggcctac tggggtggcg gctgtgctgc | 240 |
| acccaccctg cgcctcccct gcagaacacc ttcctccaca gccccaccc ctgcctcacc | 300 |
| cacctgcgtg cctcagtggc ttctagaaac ccctgaattc cctgcagctg ctcacagcag | 360 |
| gctgacctca gacttgccat tcctcctact gcttccagaa agaaagctga agcaaggcc | 420 |
| acacgtatac aggcagcaca caggcatgtg tggatacaca tggacagaca cggacacaca | 480 |
| caaacacatg gacacacaga gacgtgctaa cccatgggca cacacataca cagacatgga | 540 |
| cccacacaca aacatatgtg gacacacatg tacaaacatg cacaggcaca caaagagaac | 600 |
| actgactaca ggcacacaca cacacgggca cactacccac aggcacacaa cagatggaca | 660 |
| cgcgtacaca gacatgcaca cacccacagg cacaacacgt gcgcatgccg gccggccccc | 720 |
| gcccacattc tcccagggcc ctgccggata tctctgtccct gcagcagttt gctccctgcg | 780 |
| ctgtgctggc cccggggctt tgggcccagg ctctgcttgt ccttctgtct ctgcttggag | 840 |
| gtgctgccat ggcacccagc ttgggctctg cctggggagc ggaggcccca gggatagcat | 900 |
| gtgaccctg ctgaggccag gctcctgatg aaggcagcag atagccccca cacccaccgg | 960 |

```
tgagcagaac cagagcctgt gccatgtgct gagagcaggc agtgactaag catatgggcc    1020
cagagggcag agtggctgcc ctgggcagct gctcctctta gcaggaggcc tcaggagatg    1080
agctagagca agtctgcccc tgcaaatacc acctgctccc caacccacag cagggagcag    1140
gcgaggtcag acagcagcag cccgggaagg accgagcccc agcagggaag cagggcccg     1200 agtgaggtct ccacacccaa cgcacagtgc tgtctctaac tggggccacc tccgagtccc    1260
cgccacactc ttggcccttt ggagtcctgg gctccaggtg tctcccaagg gcccatctgt    1320 gcagggatg caaccccccg aatgtcctca tcccactgtg gagctcaggt ctctgtctgc     1380
tccctgggtc ctggcagggt aggacaagtc cgccaggatg tccccatgca gactctgctc    1440
caagagggag ctggagagtc agggccttgg tgagggagtc aggatcgggt tccccccagc    1500
tcagtcctcc cacctgccag cccccacagc acagggcagg gccacacccc ctgcttcccc    1560
ctccaggaga gtcaggacat gctggccgct gctccgctgg gccccgccc tccagccccc     1620 accttggtct gtgtgctgca tcccccacgc tctctctgcc accccaggac tctgaggaaa    1680
agacctcaga gtcccagccc tgcccagcct cggcctgtgc cccgctgca tcaggctttc     1740 aggggcccag cccatgccct gggcagtgcc cgagcccccc tgcacttgct ctccccaccc    1800
ctgggtgcag cacagcctag ggccaagggg tgggcctaga ggatgggccc cgggggggct    1860
ttgctgggtg ccaccccagc ctgacctat tcccccgtgc tgtgtctcct gcag           1914
```

<210> SEQ ID NO 5
<211> LENGTH: 2432
<212> TYPE: DNA
<213> ORGANISM: Mus musculus

<400> SEQUENCE: 5

```
gtaaacccac caatgtcagc gtgtctgtga tcatgtcaga gggagatggc atctgctact      60
gagccaccct gcctgtccct actcctgaaa taaactctgt gctcatccaa agtatccctg     120
cacttccatc cagtgcctgt ccatcatcct tagggtctac agaacacagg gagggggtcag    180 ggcccaggga gggagaaaca ccaccaccta agcttgtaag gcctcggaga ctttgaagac     240
ccttcatgcc tagagtatat gtgtatgcat gtctatgtat tggtgagtgc ttatggatgg    300
gtccatgtgc cttcatgtgt gtacctgtgt gcagcaagag aggagtgagt ttgtgtgcac    360
ctatggttta taggtatgta tatgggtata agtacatatg tggacacact atatctatgt    420
ccctgtgagc aagtgtgtgc ctgtgcatac ctatgagcat gcatatatct atgtgtgttc    480
atgttggtgg aaacatgaga gtgtgtgcac ctgccctgtg aatgtgcaat gagtgaatgg    540
gaagtaagaa taaactgggg atgaaatcca aggcgagcag actcagccaa gaaggcaaag    600
ctcatggagt agtccccagg gcagtgggtt gctgcacaag tactctgagt ggtgggtggt    660
gtggctgttt attagaccgc agcttctaac ccaaacaaga cagggataga tggagcaaaa     720
gggtagcacc atcaaggctg gtgccgtgtg gggtcacaa tagagatgat ggtatgagaa     780
tgaagggatg aacacagggg cactgggaag aagatgccac gcaccctcag taggccatcc     840
ctgaatggaa acatgcattc agggtgacca ctgactcatg agaaagacat atagcatggc    900
acagacaacc ctcagcagca ccctgctctt cacacatgca catgggcata caccctgttc     960
tgcatacatg cacatgggca tacatgcaca gacactcaca tttgcacact cacacagacc    1020
tgaaccctgg aggaagatga agttcacagc ccacacccag cttctggaaa gcaaggggag    1080
tcccctccaa gccccgggga gaattccag gccgacact gacaactaca cacaatggac      1140
aagggcatag gccctccag gtgccccctt tctaacctaa gtctcccttc ccatcctgag     1200
```

```
cccaagtatc acaaaccaga agcaggataa gaggcaaatc tgggaagaag caggagcagg   1260
ccatggagac cactcccaca caggcctcgg cctcctccat gggcacccct agaacacaaa   1320
gttctacaac caggtatact tggagcccag gtgtccacaa gagggcagtg ggggccctgc   1380
tcctgtctca caggccttca gaacttcggg ggggggggg aggagttgct ggtttctagc   1440
aacttccctc tgctctcaga gcaagagtgg agtaaaggcc catgcatgcc ctggatactc   1500
tccagcttga aagtccagtt ccctgagaat agcaagagca acagaccagc ttgggaaacc   1560
tgactcagaa aagtaccata gccacccatg gaatccaagg cctggcccat gacagagaat   1620
cctagtaagg aggagtcaat aggtgaaaga ctgaatcccc acaggagag ggggcagaga    1680 agctggagaa tcacgatagt cgggaaagat gatgagtgag cggctggagg gtaatggatg   1740
gctggctaca aggatgaacg atggggatga tggatggatt gatggatggc tgcagtgaca   1800
gaaatacgag tggttgacta tcagtacaca tttcctactg ccacttaaaa tgaaactctg   1860
tgcgcagaga acctgaggac agcagggttg gctctactgg gggtctttac tgttgcttaa   1920
cccccagtca cagctcttaa gaatgcaaca gagtcctctg accacatgtc caggccttgg   1980
tagtctaact ttggcccaga atcacattg gcctgtatct gtttgaaggt gtctgatctt    2040
acacaaccct agtacccaag ccaagattag cctaagaact ggggtttagg gaggtattgc    2100
taaatatcta gaaaggactg agacctaagg agccttgggt tcaaactctt ctcagagttt   2160
gacagaaaca actctcttac catgacaggt ctctaattaa ggtttcccta agagagagag   2220
atgggtcttg gggccatctc aagaactgct gggattccag tcccttacct gggaccctgc   2280
ctcctcatta tccctgaaca agtcccttcc cgggaataag ggaccctac caccactgtc    2340 cccaaagccc aaggaggcat agaagcagaa accttaagtc tgagccccca tccccatggg   2400
tttggatcta gaaggtcatc tatgtcttac ag                                 2432

<210> SEQ ID NO 6
<211> LENGTH: 1411
<212> TYPE: DNA
<213> ORGANISM: Mus musculus

<400> SEQUENCE: 6
gtaaatgatc ccagtgtcct tggagccctc tggtcctaca ggactctgac acctacctcc     60 accctccct gtaaataaa agcacccagc actgccttgg gaccctgcaa taatgtcctg      120
gtgatttctg agatgtagag tctagctagg tcatggaatg aggggtctcc atggtttgag   180
gcctgagttg tgactaagga aaaacccata ggcctacact gccacaccca gcactttga    240 atttgcctga catgaaaaga atttacctct ccctggaaag tggagcctta tccctaggca   300
gttcccttac cagaccttcc tctagcttgc actttgttct gggcacagaa tgtgtctaac   360
cccccaaagc aaggaagaca caacctctac ctccctcact ctgtccttac ccttttcct   420 ggctaagcat ctcactgagt gcgctgaata gatgcatgtg ccacagtct tgcagacaga    480 cccttgccat ctctccactc agctttccag aggctaagtc tagcccgtat ggtgataatg   540
cagggagctc tatgctatct cagtgctatc agactcccaa gtggaggatg aacatggacc   600
cattaaaacc aacctgcgca gcaacaccct gccaataagg cccgtatgtg aaaatgtgca   660
cacatctaca catgcacagg cacacacaca cacatgaca tgggcacaca cacatacaga    720
gagagagaat cacagaaact cccatgagca tcctatacag tactcaaaga taaaaaggta   780
ccaggtctac cccatgatc atcctcggca tttacaagtg ggccaactga tacagataaa   840
acttttctat gccaaggacg ccaacatata cacaagtccg ctcatgacaa atctgtccct    900
```

```
gaacctcaga ctggcgcccg tgactcatac agtggacact cctccaaagc tgtatagctt    960
cctttacttc cctgtgtgta ctttctctga agtacactca tcacacagaa gaggccctgt   1020
gattactctg gccctctgtt cttggtcatc agagaataga cagaagatca ggcaaactac   1080
acagacactt cccacaatca tcacaggccc tgactctgct ctccagtctc aaaactgaag   1140
gctggagcac acagaataag ctcctgcaca ggccaggcca gtatcgggtc cagtgtgtct   1200
gactgagccc agggacaaaa tggcagcact ttggggaact gaggtttctg gtccaagaag   1260
gagagatgga ggcccaggga gggtctgctg acccagccca gcccagccca gctgcagctt   1320
tctcctgggc ctccatacag cctcctgcca cacagggaat ggccctagcc ccaccttatt   1380
gggacaaaca ctgaccgccc tctctgtcca g                                  1411

<210> SEQ ID NO 7
<211> LENGTH: 1357
<212> TYPE: DNA
<213> ORGANISM: Mus musculus

<400> SEQUENCE: 7
gtaaatgagc tcagcaccca caaagctctc aggtcctaag agacactggc acccatatcc     60
atgcatccct tgtataaata aagcatccag caaagcctgg taccatgtaa aactgtcctg    120
gttctttcca aggtatagag catagctcac gggctgatag gtctggccag ggttggagga    180
cagccttgtc tataggaaga gaatgaggtt tctgcactgc atgactcaga ggtcatgagt    240
cattctgcct tggactgttg gggcttggct ttaggcagtg ccttttcctt gccttcccat    300
gaaccagcag ctgccagaca tagagataat cctaggaagc tcaaatggaa taagcacaca    360
aacccacctc ccttaggctg ttcctgtccc cctgccccat ttctctactt aggggttttt    420
ctgagtctat tgtggagtga cacatggcca ggggcattcc atagacccttt gtcatctata    480 ctctcaactc aggcagcttt tcacagacga ggtctgcaca cccatacaaa tggctcactc    540
ctgcctgtgc cacctggggc tgaggcacat ggctcttgat gccccaaggg agggactatt    600
agatagccac actcatgcta aatcctgacc ctgctgaaca ccatccagtc catatagcac    660
atgtatcctc atgctcgtga gcacaaaacg catttaacac actgggacaa ctcctctgtg    720
cccagcacag cacctacatc cagcaatgta tcaccataca cacggccaaa aattcaatgc    780
ccacgtttct gccatcacaa tcagacacac ctttcctctt ctgaggacac tccattctcc    840
gctcaaaaca agacctctga agccagattc atctctggta cctcggggtc atgcttcaac    900
cccacatgaa taattcaaac catagccata atggtctgaa tcacttcaca ctgggatgtt    960
cccaagttca ggcaagaaaa gccacaggct ctgctgatga ctgaagaata gcaaagggtc   1020
agtccagctg tatagccact gttgacctgg gtcacaggcc ctgctgaccc tccaccttct   1080
cctgtactga aggaatgaaa gatgagacaa gcatagaggg cacttgaata atccaggtca   1140
ctctgaggtc catccaaggc attattggac tcaggtggag gaagctgaga ctgatgtccc   1200
agagggaaag gaaggaaagc aggccccggg gagggtctgc tgtcccagtc aggctggaga   1260
tctctcctct gacttcatgc agacatgtct gcctcacagg gaatctctcc cagcatcaac   1320
catgttggga caaacactga ctgtcctctc tgttcag                            1357

<210> SEQ ID NO 8
<211> LENGTH: 1472
<212> TYPE: DNA
<213> ORGANISM: Mus musculus

<400> SEQUENCE: 8
```

```
gtaaatgaga acagcaccta gccattcctc gggtcttaca agacactgat accagccta      60
accggtgaac cctataaata aagcacccag agatgggacc ttgtgagatt atcttggttc     120
tttacatggc acatagttca tgatacacct cagccacagg ctgtggggtc tggccagggt     180
tcaaggtgta agttaacatc caagaaagaa caaggtctta tactgccaga cccagggcat     240
gcaagtggac ctgcccttgc cagagatcat ccctctctgc atagcaagtt tgacccaagg     300
ggccctcttc atactcttcc ccacaaccag caactgttct gtgatgagtc tggagataga     360
aatatcgccc tagaaaatat ccaaagaaag gaacacagaa agtgtatccc acctcaacac     420
gaaccccacc ttcatttgtc tgtccttccc tctaccgtga ctcccctacc ttgacctagg     480
aggtctctgt atgtattaca tagacaggca ggaagactca tacatgaagc ccgttcatct     540
ccaccacacc cctagcgata gggataggga tgagtactcc taagagacta cctcccatat     600
gacattcact cacacctaag ttccaagaca ctgagagact tatgacccta gctgccccca     660
aggaagtaac taatcaaata cctacataga tgctgagacc agaactatta gaaccagcct     720
gctaagcatc actcaaccca catggtacct ccaagcctac atacatccac tgatacctca     780
cctaggcagt atgaatagca accaaaccca tcttagtgtc gggatatccc tagacactac     840
ctaaatgtac acatttggac cagtgaagat gaaatagctc tcatgggtac ctaactgttt     900
tcccctaaca cacacaagta ccttcagacc cattctgtcc ctctatgcct aagcccctat     960
tttcatccct tacagttaac actctcccat agctgtataa cctgactcac ttcccaatgt    1020
ggaccttcta ggaagcccag gtatcatcaa acgcaggccc tactctcact ctgtccctct    1080
gtactcagtc accagggaac aagcagtagg tcaggcaagc tgcagagcta ttacctacag    1140
ggcttccaag ccttgaatca gccaagccag ccccagtact gagggatagg gtagacaaaa    1200
agggttcctg catagcccag gccagcatca ggtccagtgt atctggctct acccagggac    1260
aaaacggcag cacattgggg agctgaggtt tctggttcac agagaacata aggagagat    1320
ggccccaggg agggtcagat ggccccaggg agggtctgct gacccagtca ggctgcagct    1380
ttctcctggg cctccatgca gcctcctgcc acacagggaa tggccctagc tctaccttgt    1440
tgggacaaac actgactttc ctctctgttc ag                                  1472
```

<210> SEQ ID NO 9
<211> LENGTH: 1860
<212> TYPE: DNA
<213> ORGANISM: Mus musculus

<400> SEQUENCE: 9

```
gtaaacccac actgtacaat gtctccctga tcatgtctga cacaggcggc acctgctatt      60
gaccatgcta gcgctcaacc aggcaggccc tgggtgtcca gttgctctgt gtatgcaaac     120
taaccatgtc agagtgagat gttgcatttt ataaaaatta gaaataaaaa aaatccattc     180
aaacgtcact ggttttgatt atacaatgct catgcctgct gagacagttg tgttttgctt     240
gctctgcaca caccctgcat acttgcctcc accctggccc ttcctctacc ttgccagttt     300
cctccttgtg tgtgaactca gtcaggctta aacagacag agtatgaaca tgcgattcct     360
ccagctactt ctagatatat ggctgaaagc ttgcctaacc tggtgcaggc agcattcagg     420
cacatatata gacacacatg catttataca tagatatata ggtacacatg tgtagacaca     480
tacatgaatg tgtattcatg gacacacaga caaaggtaca catatataca catgagttca     540
tgcgcacaca catgcatgga cacttacaaa cgccttcaga gacaaatagg catagacaca     600
caaccactca cagaaacaga taccaatatg catggtcctg tgtacacaga aacagactat     660
```

```
aggcaaatat acacaaataa actatataga tacaaagata tgcatataca cacatgtaca    720
gaaacatctt cacatgtgta cactaacatg tgaacaggta tagcacacag atacacctgg    780
actctgacca gggctgtaat ctccaaggct cacggctcag agagcctaca ctaggctggg    840
tcactgatac tcctcaggag cccactctat gattgggaga gataacccca ggtacaaagt    900
atgcctatct gtctcaacac catggggcag aagatactcc actaaccacc catgacagaa    960
agttagcctt ggctgtgtct ccattaatag aacacctcag aagaccaatg tgaaattgcc   1020
taacccactc acacccaccc tgatctccag ttcaaaatgc agaaaacata atgcagttgt   1080
ccaaaagatg ccccaaccac acacacacac acacacacac acacacacac acacacacac   1140
acacacacac acacacacca tcaaggagcc tctgtaagga gtcaccaccc aataacactg   1200
cctctttggg ctcatatcct ggacattctt catattcata tccatttggg gcctaggctt   1260
tagatatccc caagggctca tctttacagg gatcagagat cccaataaat gccctggtcc   1320
cacagcctcc ctcaggtatc tgtctgttta tctcttggta ccaagaccca acattgctgg   1380
caggggtagg acaagcaacg cacgggaact ctgatcaaag aaagtcatga gatgcctgag   1440
tccttcagga agtaaggagg gacaacctct ggtatccctg ttcttattgc taaagcccaa   1500
gagacaggga gacctgctct aaattctcag tctaaacagc accgatggca ccacctgctc   1560
agggaaagtc cagagcacac caatatcatt ttgccacagt tcctgagtct gcctttaccc   1620
aggtccatac attgcatctg tcttgcttgc tctgctgccc cagggctcct ggaacaaagg   1680
ctccaaatta gtgtgtccta cagcttggcc tgttctgtgc ctccgtctag cttgagctat   1740
taggggacca gtcaatactc gctaagattc tccagaacca tcagggcacc ccaacccta    1800 tgcaaatgct cagtcacccc aagacttggc ttgaccctcc ctctctgtgt cccttcatag   1860

<210> SEQ ID NO 10
<211> LENGTH: 87
<212> TYPE: DNA
<213> ORGANISM: Homo sapiens

<400> SEQUENCE: 10
agcctgtgga ccaccctgtc cacgtttgtg gccctcttca tcctcaccct cctctacagc     60
ggcattgtca ctttcatcaa ggtgaag                                         87

<210> SEQ ID NO 11
<211> LENGTH: 78
<212> TYPE: DNA
<213> ORGANISM: Homo sapiens

<400> SEQUENCE: 11
gggctgtgga cgaccatcac catcttcatc acactcttcc tgttaagcgt gtgctacagt     60
gccaccgtca ccttcttc                                                   78

<210> SEQ ID NO 12
<211> LENGTH: 78
<212> TYPE: DNA
<213> ORGANISM: Homo sapiens

<400> SEQUENCE: 12
gggctgtgga ccaccatcac catcttcatc acactcttcc tgctaagcgt gtgctacagt     60
gccaccatca ccttcttc                                                   78

<210> SEQ ID NO 13
<211> LENGTH: 81
<212> TYPE: DNA
```

```
<213> ORGANISM: Homo sapiens

<400> SEQUENCE: 13
aacctgtggg ccaccgcctc caccttcatc gtcctcttcc tcctgagcct cttctacagt    60
accaccgtca ccttgttcaa g                                              81

<210> SEQ ID NO 14
<211> LENGTH: 63
<212> TYPE: DNA
<213> ORGANISM: Mus musculus

<400> SEQUENCE: 14
actgtgacct tcctcaccct cttcctactg agcttgttct acagcacagc actcactgtt    60
aca                                                                  63

<210> SEQ ID NO 15
<211> LENGTH: 84
<212> TYPE: DNA
<213> ORGANISM: Mus musculus

<400> SEQUENCE: 15
gggctctgga cgaccatcac catcttcatc agcctcttcc tgctcagtgt gtgctacagc    60
gctgctgtca cactcttcaa ggta                                           84

<210> SEQ ID NO 16
<211> LENGTH: 78
<212> TYPE: DNA
<213> ORGANISM: Mus musculus

<400> SEQUENCE: 16
gggctctgga cgaccatcac catcttcatc agcctcttcc tgctcagcgt gtgctacagc    60
gcctctgtca cactcttc                                                  78

<210> SEQ ID NO 17
<211> LENGTH: 78
<212> TYPE: DNA
<213> ORGANISM: Mus musculus

<400> SEQUENCE: 17
gggctctgga cgaccatcac catcttcatc agcctcttcc tgctcagcgt gtgctacagc    60
gcctctgtca ccctcttc                                                  78

<210> SEQ ID NO 18
<211> LENGTH: 84
<212> TYPE: DNA
<213> ORGANISM: Mus musculus

<400> SEQUENCE: 18
aacctgtgga ccactgcctc caccttcatc gtcctcttcc tcctgagcct cttctacagc    60
accaccgtca ccctgttcaa ggtg                                           84

<210> SEQ ID NO 19
<211> LENGTH: 30
<212> TYPE: PRT
<213> ORGANISM: Homo sapiens

<400> SEQUENCE: 19

Gly Glu Ala Ala Arg Arg Pro Gly Leu Pro Leu Pro Leu Leu Leu Leu
 1               5                  10                  15

His Gln Leu Leu Leu Leu Phe Leu Ser His Leu Arg Arg Leu
```

-continued

```
                    20                  25                  30

<210> SEQ ID NO 20
<211> LENGTH: 26
<212> TYPE: PRT
<213> ORGANISM: Homo sapiens

<400> SEQUENCE: 20

Asp Ala Ala His Pro Val Ala Ala Ser Leu Pro Leu Leu Ala Gly Thr
1               5                   10                  15

Leu Leu Leu Leu Gly Ala Ser Ala Ala Pro
            20                  25

<210> SEQ ID NO 21
<211> LENGTH: 24
<212> TYPE: PRT
<213> ORGANISM: Homo sapiens

<400> SEQUENCE: 21

Ser Ser Ala Gly Ser Leu Ala Ala Gly Pro Leu Leu Val Ala Leu Ala
1               5                   10                  15

Leu Tyr Pro Leu Ser Val Leu Phe
            20

<210> SEQ ID NO 22
<211> LENGTH: 30
<212> TYPE: PRT
<213> ORGANISM: Homo sapiens

<400> SEQUENCE: 22

Asp Ala Ala His Pro Gly Arg Ser Val Val Pro Ala Leu Leu Pro Leu
1               5                   10                  15

Leu Ala Gly Thr Leu Leu Leu Leu Glu Thr Ala Thr Ala Pro
            20                  25                  30

<210> SEQ ID NO 23
<211> LENGTH: 26
<212> TYPE: PRT
<213> ORGANISM: Homo sapiens

<400> SEQUENCE: 23

Ser Ala Ser Ser Asn Ile Ser Gly Gly Ile Phe Leu Phe Phe Val Ala
1               5                   10                  15

Asn Ala Ile Ile His Leu Phe Cys Phe Ser
            20                  25

<210> SEQ ID NO 24
<211> LENGTH: 27
<212> TYPE: PRT
<213> ORGANISM: Homo sapiens

<400> SEQUENCE: 24

Ala Ser Gly Thr Ser Pro Gly Leu Ser Ala Gly Ala Thr Val Gly Ile
1               5                   10                  15

Met Ile Gly Val Leu Val Gly Val Ala Leu Ile
            20                  25

<210> SEQ ID NO 25
<211> LENGTH: 29
<212> TYPE: PRT
<213> ORGANISM: Homo sapiens

<400> SEQUENCE: 25
```

-continued

```
Ser Gly Thr Thr Arg Leu Leu Ser Gly His Thr Cys Phe Thr Leu Thr
1               5                   10                  15

Gly Leu Leu Gly Thr Leu Val Thr Met Gly Leu Leu Thr
            20                  25
```

<210> SEQ ID NO 26
<211> LENGTH: 27
<212> TYPE: PRT
<213> ORGANISM: Homo sapiens

<400> SEQUENCE: 26

```
Asn Gly Gly Thr Ser Leu Ser Glu Lys Thr Val Leu Leu Val Thr
1               5                   10                  15

Pro Phe Leu Ala Ala Ala Trp Ser Leu His Pro
            20                  25
```

<210> SEQ ID NO 27
<211> LENGTH: 32
<212> TYPE: PRT
<213> ORGANISM: Homo sapiens

<400> SEQUENCE: 27

```
Cys Glu Gly Ile Ser Leu Leu Ala Gln Asn Thr Ser Trp Leu Leu Leu
1               5                   10                  15

Leu Leu Leu Ser Leu Ser Leu Leu Gln Ala Thr Asp Phe Met Ser Leu
            20                  25                  30
```

<210> SEQ ID NO 28
<211> LENGTH: 22
<212> TYPE: PRT
<213> ORGANISM: Homo sapiens

<400> SEQUENCE: 28

```
Ser Gly Ala Pro Thr Leu Ser Pro Ser Leu Leu Gly Leu Leu Leu Pro
1               5                   10                  15

Ala Phe Gly Ile Leu Val
            20
```

<210> SEQ ID NO 29
<211> LENGTH: 39
<212> TYPE: PRT
<213> ORGANISM: Homo sapiens

<400> SEQUENCE: 29

```
Asp Leu Cys Asn Glu Lys Leu His Asn Ala Ala Pro Thr Arg Thr Ala
1               5                   10                  15

Leu Ala His Ser Ala Leu Ser Leu Gly Leu Ala Leu Leu Leu Ala
            20                  25                  30

Val Ile Leu Ala Pro Ser Leu
        35
```

<210> SEQ ID NO 30
<211> LENGTH: 24
<212> TYPE: PRT
<213> ORGANISM: Homo sapiens

<400> SEQUENCE: 30

```
Ser Gly Ala Gly Pro Trp Ala Trp Pro Phe Leu Ser Leu Ala
1               5                   10                  15

Leu Met Leu Leu Trp Leu Leu Ser
            20
```

-continued

```
<210> SEQ ID NO 31
<211> LENGTH: 26
<212> TYPE: PRT
<213> ORGANISM: Homo sapiens

<400> SEQUENCE: 31

Asn Ala Gly Glu Met Leu His Gly Thr Gly Leu Leu Leu Ser Leu
1               5                   10                  15

Ala Leu Met Leu Gln Leu Trp Leu Leu Gly
            20                  25

<210> SEQ ID NO 32
<211> LENGTH: 49
<212> TYPE: PRT
<213> ORGANISM: Homo sapiens

<400> SEQUENCE: 32

Ala Arg Gly Leu Met Asn Gly Tyr Arg Gly Pro Ala Met Asp Ser Glu
1               5                   10                  15

Glu Asp Met Met Val Thr Ala Leu His Ser Leu Thr Leu Gln Thr Val
            20                  25                  30

Val Ile His Ser Leu Ser Ser Val Leu Pro Gly Ile Thr Leu Ala Ile
        35                  40                  45

Asn

<210> SEQ ID NO 33
<211> LENGTH: 30
<212> TYPE: PRT
<213> ORGANISM: Homo sapiens

<400> SEQUENCE: 33

Ser Ser Gly His Ser Arg His Arg Tyr Ala Leu Ile Pro Ile Pro Leu
1               5                   10                  15

Ala Val Ile Thr Thr Cys Ile Val Leu Tyr Met Asn Val Leu
            20                  25                  30

<210> SEQ ID NO 34
<211> LENGTH: 27
<212> TYPE: PRT
<213> ORGANISM: Homo sapiens

<400> SEQUENCE: 34

Ser Gly Ala Ser Ser Leu His Arg His Phe Gly Leu Leu Ala Ser
1               5                   10                  15

Leu Ala Pro Leu Val Leu Cys Leu Ser Leu Leu
            20                  25

<210> SEQ ID NO 35
<211> LENGTH: 26
<212> TYPE: PRT
<213> ORGANISM: Homo sapiens

<400> SEQUENCE: 35

Ser Thr Gly Ser His Cys His Gly Ser Phe Ser Leu Ile Phe Leu Ser
1               5                   10                  15

Leu Trp Ala Val Ile Phe Val Leu Tyr Gln
            20                  25

<210> SEQ ID NO 36
<211> LENGTH: 31
<212> TYPE: PRT
<213> ORGANISM: Homo sapiens
```

-continued

```
<400> SEQUENCE: 36

Gly Ala Ala Pro Gln Pro Gly Pro Ala His Leu Ser Leu Thr Ile Thr
1               5                   10                  15

Leu Leu Met Thr Ala Arg Leu Trp Gly Gly Thr Leu Leu Trp Thr
            20                  25                  30

<210> SEQ ID NO 37
<211> LENGTH: 30
<212> TYPE: PRT
<213> ORGANISM: Mus musculus

<400> SEQUENCE: 37

Asn Ala Ala Val Pro Thr Gly Ala Ser Thr Trp Thr Met Ala Gly Val
1               5                   10                  15

Leu Leu Phe Ser Leu Ser Ser Val Ile Leu Gln Thr Leu Leu
            20                  25                  30

<210> SEQ ID NO 38
<211> LENGTH: 35
<212> TYPE: PRT
<213> ORGANISM: Mus musculus

<400> SEQUENCE: 38

Asn Glu Arg Leu Val Ser Ala Ala Pro Gly His Ala Leu Leu Ser Ser
1               5                   10                  15

Val Thr Leu Gly Leu Ala Thr Ser Leu Ser Leu Leu Thr Val Met Ala
            20                  25                  30

Leu Cys Leu
        35

<210> SEQ ID NO 39
<211> LENGTH: 26
<212> TYPE: PRT
<213> ORGANISM: Mus musculus

<400> SEQUENCE: 39

Ser Ala Ala Ser His Tyr Gln Gly Ser Phe Pro Leu Val Ile Leu Ser
1               5                   10                  15

Leu Ser Ala Val Ile Phe Val Leu Tyr Gln
            20                  25

<210> SEQ ID NO 40
<211> LENGTH: 24
<212> TYPE: PRT
<213> ORGANISM: Mus musculus

<400> SEQUENCE: 40

Ser Ser Gly Val Cys Trp Thr Ala Thr Trp Leu Val Val Thr Thr Leu
1               5                   10                  15

Ile Ile His Arg Ile Leu Leu Thr
            20

<210> SEQ ID NO 41
<211> LENGTH: 32
<212> TYPE: PRT
<213> ORGANISM: Mus musculus

<400> SEQUENCE: 41

Asn Phe Ser Ala Ala Gly Leu Gly Leu Arg Ala Ser Ile Pro Leu Leu
1               5                   10                  15

Gly Leu Gly Leu Leu Leu Ser Leu Leu Ala Leu Leu Gln Leu Ser Pro
            20                  25                  30
```

```
<210> SEQ ID NO 42
<211> LENGTH: 16
<212> TYPE: PRT
<213> ORGANISM: Mus musculus

<400> SEQUENCE: 42

Ala Lys Ser Phe Tyr Phe Ile Cys Tyr Leu Cys Leu Tyr Leu Ala Leu
1               5                   10                  15

<210> SEQ ID NO 43
<211> LENGTH: 22
<212> TYPE: PRT
<213> ORGANISM: Rattus norvegicus

<400> SEQUENCE: 43

Gly Asn Ser Ala Glu Gly Ser Met Pro Ala Phe Leu Leu Phe Leu Leu
1               5                   10                  15

Leu Gln Leu Trp Asp Thr
            20

<210> SEQ ID NO 44
<211> LENGTH: 32
<212> TYPE: PRT
<213> ORGANISM: Rattus norvegicus

<400> SEQUENCE: 44

Cys Gly Gly Ile Ser Leu Leu Val Gln Asn Thr Ser Trp Leu Leu Leu
1               5                   10                  15

Leu Leu Leu Ser Leu Ser Phe Leu Gln Ala Thr Asp Phe Ile Ser Leu
            20                  25                  30

<210> SEQ ID NO 45
<211> LENGTH: 29
<212> TYPE: PRT
<213> ORGANISM: Rattus norvegicus

<400> SEQUENCE: 45

Ser Ala Ala Thr Arg Pro Glu Pro His Tyr Phe Phe Leu Leu Phe Leu
1               5                   10                  15

Phe Thr Leu Val Leu Ala Ala Ala Arg Pro Arg Trp Arg
            20                  25

<210> SEQ ID NO 46
<211> LENGTH: 24
<212> TYPE: PRT
<213> ORGANISM: Rattus norvegicus

<400> SEQUENCE: 46

Ser Ser Gly Val His Trp Ile Ala Ala Trp Leu Val Val Thr Leu Ser
1               5                   10                  15

Ile Ile Pro Ser Ile Leu Leu Ala
            20

<210> SEQ ID NO 47
<211> LENGTH: 26
<212> TYPE: PRT
<213> ORGANISM: Rattus norvegicus

<400> SEQUENCE: 47

Ser Ala Ala Ser His Tyr Gln Gly Ser Phe Pro Leu Ile Ile Leu Ser
1               5                   10                  15

Phe Trp Ala Val Ile Leu Val Leu Tyr Gln
```

-continued

```
<210> SEQ ID NO 48
<211> LENGTH: 22
<212> TYPE: PRT
<213> ORGANISM: Rattus norvegicus

<400> SEQUENCE: 48

Arg Asn Thr Gly Phe Leu Leu Ala Trp Pro Thr Phe Phe Leu Pro Val
1               5                   10                  15

Phe Leu Ala Trp Leu Phe
            20

<210> SEQ ID NO 49
<211> LENGTH: 30
<212> TYPE: PRT
<213> ORGANISM: Rattus norvegicus

<400> SEQUENCE: 49

Ser Ser Ala Gly Ala Arg Glu Ser Cys Val Ser Leu Phe Leu Val Val
1               5                   10                  15

Leu Pro Ser Leu Leu Val Gln Leu Leu Cys Leu Ala Glu Pro
            20                  25                  30

<210> SEQ ID NO 50
<211> LENGTH: 33
<212> TYPE: PRT
<213> ORGANISM: Candida albicans

<400> SEQUENCE: 50

Ser Ser Gly Val Lys Ala Thr Gln Gln Met Ser Met Val Lys Leu Val
1               5                   10                  15

Ser Ile Ile Thr Ile Val Thr Ala Phe Val Gly Gly Met Ser Val Val
            20                  25                  30

Phe

<210> SEQ ID NO 51
<211> LENGTH: 32
<212> TYPE: PRT
<213> ORGANISM: Saccharomyces cerevisiae

<400> SEQUENCE: 51

Asn Ala Ala Thr Asn Val Lys Ala Asn Leu Ala Gln Val Val Phe Thr
1               5                   10                  15

Ser Ile Ile Ser Leu Ser Ile Ala Ala Gly Val Gly Phe Ala Leu Val
            20                  25                  30

<210> SEQ ID NO 52
<211> LENGTH: 25
<212> TYPE: PRT
<213> ORGANISM: Sus scrofa

<400> SEQUENCE: 52

Ala Arg Ala Ala Pro Thr Thr Ser Leu Gly Ser Leu Met Thr Val Ser
1               5                   10                  15

Ala Leu Ala Ile Leu Gly Trp Ser Val
            20                  25

<210> SEQ ID NO 53
<211> LENGTH: 26
<212> TYPE: PRT
<213> ORGANISM: Sus scrofa
```

-continued

<400> SEQUENCE: 53

Ser Ala Ala Pro Ser Leu His Leu Pro Pro Gly Ser Leu Leu Ala Ser
1               5                   10                  15
Leu Val Pro Leu Leu Leu Ser Leu Pro
            20                  25

<210> SEQ ID NO 54
<211> LENGTH: 18
<212> TYPE: PRT
<213> ORGANISM: Trypanosoma brucei

<400> SEQUENCE: 54

Ser Asn Ser Phe Val Ile His Lys Ala Pro Leu Phe Leu Ala Phe Leu
1               5                   10                  15
Leu Phe

<210> SEQ ID NO 55
<211> LENGTH: 24
<212> TYPE: PRT
<213> ORGANISM: Trypanosoma brucei

<400> SEQUENCE: 55

Asp Ser Ser Ile Leu Val Thr Lys Lys Phe Ala Leu Thr Val Val Ser
1               5                   10                  15
Ala Ala Phe Val Ala Leu Leu Phe
            20

<210> SEQ ID NO 56
<211> LENGTH: 24
<212> TYPE: PRT
<213> ORGANISM: Trypanosoma brucei

<400> SEQUENCE: 56

Asn Gly Ser Phe Leu Thr Ser Lys Gln Phe Ala Phe Ser Val Val Ser
1               5                   10                  15
Ala Ala Phe Val Ala Leu Leu Phe
            20

<210> SEQ ID NO 57
<211> LENGTH: 18
<212> TYPE: PRT
<213> ORGANISM: Trypanosoma brucei

<400> SEQUENCE: 57

Ser Asn Ser Phe Val Ile Ser Lys Thr Pro Leu Trp Leu Ala Val Leu
1               5                   10                  15
Leu Phe

<210> SEQ ID NO 58
<211> LENGTH: 23
<212> TYPE: PRT
<213> ORGANISM: Trypanosoma brucei

<400> SEQUENCE: 58

Asp Gly Ser Phe Leu Val Asn Lys Lys Phe Ala Leu Met Val Tyr Asp
1               5                   10                  15
Phe Val Ser Leu Leu Ala Phe
            20

<210> SEQ ID NO 59
<211> LENGTH: 23
<212> TYPE: PRT

-continued

<213> ORGANISM: Trypanosoma brucei

<400> SEQUENCE: 59

Asn Gly Ser Phe Leu Thr Ser Lys Gln Phe Ala Leu Met Val Ser Ala
1               5                   10                  15

Ala Phe Val Thr Leu Leu Phe
            20

<210> SEQ ID NO 60
<211> LENGTH: 23
<212> TYPE: PRT
<213> ORGANISM: Trypanosoma brucei

<400> SEQUENCE: 60

Gly Ala Ala Thr Leu Lys Ser Val Ala Leu Pro Phe Ala Ile Ala Ala
1               5                   10                  15

Ala Ala Leu Val Ala Ala Phe
            20

<210> SEQ ID NO 61
<211> LENGTH: 18
<212> TYPE: PRT
<213> ORGANISM: Trypanosoma brucei

<400> SEQUENCE: 61

Ser Asn Ser Phe Val Ile Asn Lys Ala Pro Leu Leu Leu Gly Phe Leu
1               5                   10                  15

Leu Phe

<210> SEQ ID NO 62
<211> LENGTH: 20
<212> TYPE: PRT
<213> ORGANISM: Trypanosoma congolense

<400> SEQUENCE: 62

Ser Gly Ser Ser His Gly Thr Lys Ala Ile Arg Ser Ile Leu His Val
1               5                   10                  15

Ala Leu Leu Met
            20

<210> SEQ ID NO 63
<211> LENGTH: 28
<212> TYPE: PRT
<213> ORGANISM: Gallus sp.

<400> SEQUENCE: 63

Ala Gly Asn Lys Leu Ile Gln Gln His Leu Leu Val Ile Thr Phe Val
1               5                   10                  15

Pro Phe Ile Ile Leu Gly Gln Leu Gln Gly Leu Gly
            20                  25

<210> SEQ ID NO 64
<211> LENGTH: 26
<212> TYPE: PRT
<213> ORGANISM: Gallus sp.

<400> SEQUENCE: 64

Ala Thr Leu Gly Ser Pro Ser Thr Ser Ser Phe Val Ser Leu Leu
1               5                   10                  15

Leu Ser Ala Val Thr Leu Leu Leu Leu Cys
            20                  25

```
<210> SEQ ID NO 65
<211> LENGTH: 25
<212> TYPE: PRT
<213> ORGANISM: Torpedo marmorata

<400> SEQUENCE: 65

Ser Ser Ser Gly Thr Ser Ser Lys Gly Ile Ile Phe Tyr Val Leu
1               5                   10                  15

Phe Ser Ile Leu Tyr Leu Ile Phe Tyr
            20                  25

<210> SEQ ID NO 66
<211> LENGTH: 24
<212> TYPE: PRT
<213> ORGANISM: Mesocricetus brandti

<400> SEQUENCE: 66

Ser Ser Ala Val Leu Phe Ser Ser Pro Pro Val Ile Leu Leu Ile Ser
1               5                   10                  15

Phe Leu Ile Phe Leu Met Val Gly
            20

<210> SEQ ID NO 67
<211> LENGTH: 26
<212> TYPE: PRT
<213> ORGANISM: Bos taurus

<400> SEQUENCE: 67

Ser Ala Gly Ser His Cys Cys Gly Ser Phe Ser Leu Ile Phe Leu Ser
1               5                   10                  15

Val Leu Ala Val Ile Ile Ile Leu Tyr Gln
            20                  25

<210> SEQ ID NO 68
<211> LENGTH: 23
<212> TYPE: PRT
<213> ORGANISM: Polysphondylium pallidum

<400> SEQUENCE: 68

Ser Ser Ala Thr Thr Ile Ala Phe Asn Ala Phe Val Val Phe Ala Ile
1               5                   10                  15

Val Leu Ser Val Leu Leu Phe
            20

<210> SEQ ID NO 69
<211> LENGTH: 22
<212> TYPE: PRT
<213> ORGANISM: Polysphondylium pallidum

<400> SEQUENCE: 69

Gly Ser Ala Ser Thr Val Val Ala Ser Leu Ser Leu Ile Ile Phe Ser
1               5                   10                  15

Met Ile Leu Ser Leu Cys
            20

<210> SEQ ID NO 70
<211> LENGTH: 25
<212> TYPE: DNA
<213> ORGANISM: Homo sapiens

<400> SEQUENCE: 70
acctggccat gaccccctg atccc                                      25
```

```
<210> SEQ ID NO 71
<211> LENGTH: 29
<212> TYPE: DNA
<213> ORGANISM: Homo sapiens

<400> SEQUENCE: 71
agctgcaact ggaggagagc tgtgcggag                                    29

<210> SEQ ID NO 72
<211> LENGTH: 33
<212> TYPE: DNA
<213> ORGANISM: Homo sapiens

<400> SEQUENCE: 72
agctgcaact ggaggagagc tgtgcggagg cgc                               33

<210> SEQ ID NO 73
<211> LENGTH: 25
<212> TYPE: DNA
<213> ORGANISM: Homo sapiens

<400> SEQUENCE: 73 aggggaggt gagcgccgac gagga                                         25

<210> SEQ ID NO 74
<211> LENGTH: 31
<212> TYPE: DNA
<213> ORGANISM: Mus musculus

<400> SEQUENCE: 74
aacgtcaaga gccactttcc tatgtgctac t                                 31

<210> SEQ ID NO 75
<211> LENGTH: 48
<212> TYPE: DNA
<213> ORGANISM: Mus musculus

<400> SEQUENCE: 75
ggctgcaact ggacgagacc tgtgctgagg cccaggacgg ggagctgg               48

<210> SEQ ID NO 76
<211> LENGTH: 27
<212> TYPE: DNA
<213> ORGANISM: Mus musculus

<400> SEQUENCE: 76
ggctagacct ggatgatatc tgtgctg                                      27

<210> SEQ ID NO 77
<211> LENGTH: 23
<212> TYPE: DNA
<213> ORGANISM: Mus musculus

<400> SEQUENCE: 77
agctggaact gaatgagacc tgt                                          23

<210> SEQ ID NO 78
<211> LENGTH: 33
<212> TYPE: DNA
<213> ORGANISM: Mus musculus

<400> SEQUENCE: 78 aggggaggt gaatgctgag gaggaaggct ttg                                33
```

```
<210> SEQ ID NO 79
<211> LENGTH: 4
<212> TYPE: PRT
<213> ORGANISM: Homo sapiens

<400> SEQUENCE: 79

Gly Phe Thr His
1

<210> SEQ ID NO 80
<211> LENGTH: 4
<212> TYPE: PRT
<213> ORGANISM: Homo sapiens

<400> SEQUENCE: 80

Ala Cys Thr Thr
1

<210> SEQ ID NO 81
<211> LENGTH: 4
<212> TYPE: PRT
<213> ORGANISM: Homo sapiens

<400> SEQUENCE: 81

Cys Ala Pro Ala
1

<210> SEQ ID NO 82
<211> LENGTH: 4
<212> TYPE: PRT
<213> ORGANISM: Homo sapiens

<400> SEQUENCE: 82

Ala Gly Thr Thr
1

<210> SEQ ID NO 83
<211> LENGTH: 4
<212> TYPE: PRT
<213> ORGANISM: Homo sapiens

<400> SEQUENCE: 83

Thr Ser Ser Pro
1

<210> SEQ ID NO 84
<211> LENGTH: 4
<212> TYPE: PRT
<213> ORGANISM: Homo sapiens

<400> SEQUENCE: 84

Ile Thr Val Ser
1

<210> SEQ ID NO 85
<211> LENGTH: 4
<212> TYPE: PRT
<213> ORGANISM: Homo sapiens

<400> SEQUENCE: 85

Ser Gly Thr Thr
1

<210> SEQ ID NO 86
<211> LENGTH: 4
<212> TYPE: PRT
```

<213> ORGANISM: Homo sapiens

<400> SEQUENCE: 86

Glu Gln Leu Glu
1

<210> SEQ ID NO 87
<211> LENGTH: 4
<212> TYPE: PRT
<213> ORGANISM: Homo sapiens

<400> SEQUENCE: 87

Lys Leu Val Lys
1

<210> SEQ ID NO 88
<211> LENGTH: 4
<212> TYPE: PRT
<213> ORGANISM: Homo sapiens

<400> SEQUENCE: 88

Gln Val Lys Ile
1

<210> SEQ ID NO 89
<211> LENGTH: 4
<212> TYPE: PRT
<213> ORGANISM: Homo sapiens

<400> SEQUENCE: 89

Cys Cys Gln Glu
1

<210> SEQ ID NO 90
<211> LENGTH: 4
<212> TYPE: PRT
<213> ORGANISM: Homo sapiens

<400> SEQUENCE: 90

Ala Ala Ala Met
1

<210> SEQ ID NO 91
<211> LENGTH: 4
<212> TYPE: PRT
<213> ORGANISM: Homo sapiens

<400> SEQUENCE: 91

Ala Met His Val
1

<210> SEQ ID NO 92
<211> LENGTH: 4
<212> TYPE: PRT
<213> ORGANISM: Homo sapiens

<400> SEQUENCE: 92

Gly Ser Arg Gly
1

<210> SEQ ID NO 93
<211> LENGTH: 4
<212> TYPE: PRT
<213> ORGANISM: Homo sapiens

<400> SEQUENCE: 93

Thr Cys Ile Pro
1

<210> SEQ ID NO 94
<211> LENGTH: 4
<212> TYPE: PRT
<213> ORGANISM: Homo sapiens

<400> SEQUENCE: 94

Tyr Gly Tyr Ser
1

<210> SEQ ID NO 95
<211> LENGTH: 4
<212> TYPE: PRT
<213> ORGANISM: Homo sapiens

<400> SEQUENCE: 95

Arg Ile Lys Phe
1

<210> SEQ ID NO 96
<211> LENGTH: 4
<212> TYPE: PRT
<213> ORGANISM: Homo sapiens

<400> SEQUENCE: 96

Gln Tyr Arg Ser
1

<210> SEQ ID NO 97
<211> LENGTH: 4
<212> TYPE: PRT
<213> ORGANISM: Mus musculus

<400> SEQUENCE: 97

Glu Asp Leu Cys
1

<210> SEQ ID NO 98
<211> LENGTH: 4
<212> TYPE: PRT
<213> ORGANISM: Mus musculus

<400> SEQUENCE: 98

Thr Asp Leu Cys
1

<210> SEQ ID NO 99
<211> LENGTH: 4
<212> TYPE: PRT
<213> ORGANISM: Mus musculus

<400> SEQUENCE: 99

Arg Ile Lys Phe
1

<210> SEQ ID NO 100
<211> LENGTH: 4
<212> TYPE: PRT
<213> ORGANISM: Mus musculus

<400> SEQUENCE: 100

Asp Leu Ala Arg
1

```
<210> SEQ ID NO 101
<211> LENGTH: 4
<212> TYPE: PRT
<213> ORGANISM: Mus musculus

<400> SEQUENCE: 101

Ser Ser Phe Cys
1

<210> SEQ ID NO 102
<211> LENGTH: 4
<212> TYPE: PRT
<213> ORGANISM: Mus musculus

<400> SEQUENCE: 102

His Leu Met Phe
1

<210> SEQ ID NO 103
<211> LENGTH: 4
<212> TYPE: PRT
<213> ORGANISM: Rattus norvegicus

<400> SEQUENCE: 103

Ala Pro Ser Ser
1

<210> SEQ ID NO 104
<211> LENGTH: 4
<212> TYPE: PRT
<213> ORGANISM: Rattus norvegicus

<400> SEQUENCE: 104

Lys Leu Val Lys
1

<210> SEQ ID NO 105
<211> LENGTH: 4
<212> TYPE: PRT
<213> ORGANISM: Rattus norvegicus

<400> SEQUENCE: 105

Gly Gln Lys Thr
1

<210> SEQ ID NO 106
<211> LENGTH: 4
<212> TYPE: PRT
<213> ORGANISM: Rattus norvegicus

<400> SEQUENCE: 106

Thr Leu Ala Arg
1

<210> SEQ ID NO 107
<211> LENGTH: 4
<212> TYPE: PRT
<213> ORGANISM: Rattus norvegicus

<400> SEQUENCE: 107

Arg Ile Lys Phe
1

<210> SEQ ID NO 108
```

```
<211> LENGTH: 4
<212> TYPE: PRT
<213> ORGANISM: Rattus norvegicus

<400> SEQUENCE: 108

Asn Gly Thr Pro
1

<210> SEQ ID NO 109
<211> LENGTH: 4
<212> TYPE: PRT
<213> ORGANISM: Rattus norvegicus

<400> SEQUENCE: 109

Asn Cys Leu Tyr
1

<210> SEQ ID NO 110
<211> LENGTH: 4
<212> TYPE: PRT
<213> ORGANISM: Candida albicans

<400> SEQUENCE: 110

Gly Ser Ser Ser
1

<210> SEQ ID NO 111
<211> LENGTH: 4
<212> TYPE: PRT
<213> ORGANISM: Saccharomyces cerevisiae

<400> SEQUENCE: 111

Ser Ser Lys Lys
1

<210> SEQ ID NO 112
<211> LENGTH: 4
<212> TYPE: PRT
<213> ORGANISM: Sus scrofa

<400> SEQUENCE: 112

Glu Pro Leu Ser
1

<210> SEQ ID NO 113
<211> LENGTH: 4
<212> TYPE: PRT
<213> ORGANISM: Sus scrofa

<400> SEQUENCE: 113

Asn Tyr Gly Tyr
1

<210> SEQ ID NO 114
<211> LENGTH: 4
<212> TYPE: PRT
<213> ORGANISM: Trypanosoma brucei

<400> SEQUENCE: 114

Asn Thr Thr Gly
1

<210> SEQ ID NO 115
<211> LENGTH: 4
<212> TYPE: PRT
<213> ORGANISM: Trypanosoma brucei
```

<400> SEQUENCE: 115

Asn Ala Cys Lys
1

<210> SEQ ID NO 116
<211> LENGTH: 4
<212> TYPE: PRT
<213> ORGANISM: Trypanosoma brucei

<400> SEQUENCE: 116

Glu Lys Cys Arg
1

<210> SEQ ID NO 117
<211> LENGTH: 4
<212> TYPE: PRT
<213> ORGANISM: Trypanosoma brucei

<400> SEQUENCE: 117

Thr Thr Gly Ser
1

<210> SEQ ID NO 118
<211> LENGTH: 4
<212> TYPE: PRT
<213> ORGANISM: Trypanosoma brucei

<400> SEQUENCE: 118

Glu Lys Cys Cys
1

<210> SEQ ID NO 119
<211> LENGTH: 4
<212> TYPE: PRT
<213> ORGANISM: Trypanosoma brucei

<400> SEQUENCE: 119

Glu Asp Cys Arg
1

<210> SEQ ID NO 120
<211> LENGTH: 4
<212> TYPE: PRT
<213> ORGANISM: Trypanosoma brucei

<400> SEQUENCE: 120

Glu Pro Glu Pro
1

<210> SEQ ID NO 121
<211> LENGTH: 4
<212> TYPE: PRT
<213> ORGANISM: Trypanosoma brucei

<400> SEQUENCE: 121

Asn Thr Thr Ala
1

<210> SEQ ID NO 122
<211> LENGTH: 4
<212> TYPE: PRT
<213> ORGANISM: Trypanosoma congolense

<400> SEQUENCE: 122

Ser His Leu Pro
1

<210> SEQ ID NO 123
<211> LENGTH: 4
<212> TYPE: PRT
<213> ORGANISM: Gallus sp.

<400> SEQUENCE: 123

Gln Cys Ser Gly
1

<210> SEQ ID NO 124
<211> LENGTH: 4
<212> TYPE: PRT
<213> ORGANISM: Gallus sp.

<400> SEQUENCE: 124

Thr Val Ile Pro
1

<210> SEQ ID NO 125
<211> LENGTH: 4
<212> TYPE: PRT
<213> ORGANISM: Torpedo marmorata

<400> SEQUENCE: 125

Asp Gly Glu Leu
1

<210> SEQ ID NO 126
<211> LENGTH: 4
<212> TYPE: PRT
<213> ORGANISM: Mesocricetus brandti

<400> SEQUENCE: 126

Asp Gly Arg Arg
1

<210> SEQ ID NO 127
<211> LENGTH: 4
<212> TYPE: PRT
<213> ORGANISM: Bos taurus

<400> SEQUENCE: 127

Arg Ile Gln Phe
1

<210> SEQ ID NO 128
<211> LENGTH: 4
<212> TYPE: PRT
<213> ORGANISM: Polysphondylium pallidum

<400> SEQUENCE: 128

Asn Asn Val Cys
1

<210> SEQ ID NO 129
<211> LENGTH: 4
<212> TYPE: PRT
<213> ORGANISM: Polysphondylium pallidum

<400> SEQUENCE: 129

Ser Thr Thr Thr
1

<210> SEQ ID NO 130
<211> LENGTH: 2074
<212> TYPE: DNA
<213> ORGANISM: Homo sapiens

<400> SEQUENCE: 130

```
cctccaccaa gggcccatcg gtcttccccc tggcaccctc ctccaagagc acctctgggg     60
gcacagcggc cctgggctgc ctggtcaagg actacttccc cgaaccggtg acggtgtcgt    120
ggaactcagg cgccctgacc agcggcgtgc acaccttccc ggctgtccta cagtcctcag    180
gactctactc cctcagcagc gtggtgaccg tgccctccag cagcttgggc acccagacct    240
acatctgcaa cgtgaatcac aagcccagca acaccaaggt ggacaagaaa gttggtgaga    300
ggccagcaca gggagggagg gtgtctgctg gaagccaggc tcagcgctcc tgcctggacg    360
catcccggct atgcagcccc agtccagggc agcaaggcag gccccgtctg cctcttcacc    420
cggaggcctc tgcccgcccc actcatgctc agggagaggg tcttctggct ttttccccgg    480
ctctgggcag gcacaggcta ggtgccccta acccaggccc tgcacacaaa ggggcaggtg    540
ctgggctcag acctgccaag agccatatcc gggaggaccc tgcccctgac ctaagcccac    600
cccaaaggcc aaactctcca ctccctcagc tcggacacct tctctcctcc cagattccag    660
taactcccaa tcttctctct gcagagccca atcttgtga caaaactcac acatgcccac    720
cgtgcccagg taagccagcc caggcctcgc cctccagctc aaggcgggac aggtgcccta    780
gagtagcctg catccaggga caggccccag ccgggtgctg cacgtccac ctccatctct    840
tcctcagcac ctgaactcct ggggggaccg tcagtcttcc tcttcccccc aaaacccaag    900
gacaccctca tgatctcccg gacccctgag gtcacatgcg tggtggtgga cgtgagccac    960
gaagaccctg aggtcaagtt caactggtac gtggacggcg tggaggtgca taatgccaag   1020
acaaagccgc gggaggagca gtacaacagc acgtaccgtg tggtcagcgt cctcaccgtc   1080
ctgcaccagg actggctgaa tggcaaggag tacaagtgca aggtctccaa caaagccctc   1140
ccagccccca tcgagaaaac catctccaaa gccaaaggtg ggacccgtgg ggtgcgaggg   1200
ccacatggac agaggccggc tcggcccacc ctctgccctg agagtgaccg ctgtaccaac   1260
ctctgtccct acagggcagc cccgagaacc acaggtgtac accctgcccc catcccggga   1320
tgagctgacc aagaaccagg tcagcctgac ctgcctggtc aaaggcttct atcccagcga   1380
catcgccgtg gagtgggaga gcaatgggca gccggagaac aactacaaga ccacgcctcc   1440
cgtgctggac tccgacggct ccttcttcct ctacagcaag ctcaccgtgg acaagagcag   1500
gtggcagcag gggaacgtct tctcatgctc cgtgatgcat gaggctctgc acaaccacta   1560
cacgcagaag agcctctccc tgtctccggg taaatgagtg cgacggccgg caagcccccg   1620
ctccccgggc tctcgcggtc gcacgaggat gcttggcacg taccccctgt acatacttcc   1680
cgggcgccca gcatggaaat aaagcaccca gcgctgccct gggcccctgc gagactgtga   1740
tggttctttc cacgggtcag gccgagtctg aggcctgagt ggcatgaggg aggcagagcg   1800
ggtcccactg tccccacact ggcccaggct gtgcaggtgt gcctgggccg cctaggtgg    1860
ggctcagcca ggggctgccc tcggcagggt gggggatttg ccagcgtggc cctccctcca   1920
gcagcacctg ccctgggctg gccacgggga gccctagga gccccctgggg acagacacac   1980
agcccctgcc tctgtaggag actgtcctgt tctgtgagcg ccctgtcctc cgacctccat   2040
gcccactcgg gggcatgcga cagattgagg atcc                               2074
```

<210> SEQ ID NO 131

<211> LENGTH: 330
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 131

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```

<210> SEQ ID NO 132
<211> LENGTH: 40
<212> TYPE: DNA
<213> ORGANISM: Artificial Sequence
<220> FEATURE:
<223> OTHER INFORMATION: Description of Artificial Sequence: Synthetic primer
<210> SEQ ID NO 133
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
aactggatcc atgtagaaaa gaggagaagc cccggggtc catgtagt                48

<210> SEQ ID NO 134
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
gatccacttc accttgaaga aggtgacggt ggcactgtag cacacgc                47

<210> SEQ ID NO 135
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
caccttcttc aaggtgaagt ggatcttctc ctcggtggtg gacctgaag              49

<210> SEQ ID NO 136
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
ctccagcagc agctgccctg ggctgggcca cga                               33

<210> SEQ ID NO 137
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
cagggatccc ccgaggtgca gctggaccag cctcctcctg accgtgtttt             50

<210> SEQ ID NO 138
<211> LENGTH: 68
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138

```
ctaccccaga cctccgctgc ttggtgcctg cagggcactg ggggccaggt gtcccctcag    60
caggacgt                                                            68

<210> SEQ ID NO 139
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
cctgctgagg ggacacctgg cccccagtgc cctgcaggca ccaagcagcg aggtctggg     60 gt                                                                  62

<210> SEQ ID NO 140
<211> LENGTH: 6949
<212> TYPE: DNA
<213> ORGANISM: Homo sapiens

<400> SEQUENCE: 140
cctccaccaa gggcccatcg gtcttcccc  tggcaccctc ctccaagagc acctctgggg    60
gcacagcggc cctgggctgc ctggtcaagg actacttccc cgaaccggtg acggtgtcgt   120
ggaactcagg cgccctgacc agcggcgtgc acaccttccc ggctgtccta cagtcctcag   180
gactctactc cctcagcagc gtggtgaccg tgccctccag cagcttgggc acccagacct   240
acatctgcaa cgtgaatcac aagcccagca acaccaaggt ggacaagaaa gttggtgaga   300
ggccagcaca gggagggagg gtgtctgctg gaagccaggc tcagcgctcc tgcctggacg   360
catcccggct atgcagcccc agtccagggc agcaaggcag gccccgtctg cctcttcacc   420
cggaggcctc tgcccgcccc actcatgctc agggagaggg tcttctggct ttttccccgg   480
ctctgggcag gcacaggcta ggtgccccta acccaggccc tgcacacaaa ggggcaggtg   540
ctgggctcag acctgccaag agccatatcc ggaggaccc  tgcccctgac ctaagcccac   600
cccaaaggcc aaactctcca ctccctcagc tcggacacct tctctcctcc cagattccag   660
taactcccaa tcttctctct gcagagccca atcttgtgac aaaactcac  acatgcccac   720 cgtgcccagg taagccagcc caggcctcgc cctccagctc aaggcgggac aggtgcccta   780
gagtagcctg catccaggga caggccccag ccgggtgctg acacgtccac ctccatctct   840
tcctcagcac ctgaactcct gggggaccg  tcagtcttcc tcttcccccc aaaacccaag   900
gacaccctca tgatctcccg gacccctgag gtcacatgcg tggtggtgga cgtgagccac   960
gaagaccctg aggtcaagtt caactggtac gtggacggcg tggaggtgca taatgccaag  1020
acaaagccgc gggaggagca gtacaacagc acgtaccgtg tggtcagcgt cctcaccgtc  1080
ctgcaccagg actggctgaa tggcaaggag tacaagtgca aggtctccaa caaagccctc  1140
ccagccccca tcgagaaaac catctccaaa gccaaaggtg ggacccgtgg ggtgcgaggg  1200
ccacatggac agaggccggc tcggcccacc ctctgccctg agagtgaccg ctgtaccaac  1260
ctctgtccct acagggcagc cccgagaacc acaggtgtac accctgcccc catcccggga  1320
tgagctgacc aagaaccagg tcagcctgac ctgcctggtc aaaggcttct atcccagcga  1380
catcgccgtg gagtgggaga gcaatgggca gccggagaac aactacaaga ccacgcctcc  1440
cgtgctggac tccgacggct ccttcttcct ctacagcaag ctcaccgtgg acaagagcag  1500
gtggcagcag gggaacgtct tctcatgctc cgtgatgcat gaggctctgc acaaccacta  1560
```

```
cacgcagaag agcctctccc tgtctccggg taaatgagtg cgacggccgg caagcccccg    1620
ctccccgggc tctcgcggtc gcacgaggat gcttggcacg tacccctgt acatacttcc     1680 cgggcgccca gcatggaaat aaagcaccca gcgctgccct ggcccctgc gagactgtga     1740 tggttctttc cacgggtcag gccgagtctg aggcctgagt ggcatgaggg aggcagagcg    1800
ggtcccactg tccccacact ggcccaggct gtgcaggtgt gcctgggccg cctagggtgg    1860
ggctcagcca ggggctgccc tcggcagggt gggggatttg ccagcgtggc cctccctcca    1920
gcagcacctg ccctgggctg ggcacgggga agccctagga gcccctgggg acagacacac    1980
agcccctgcc tctgtaggag actgtcctgt tctgtgagcg ccctgtcctc cgacctccat    2040
gcccactcgg gggcatgcct agtccatgcg cgtagggaca ggccctccct cacccatcta    2100
cccccacggc actaacccct ggcagccctg cccagcctcg cacccgcatg gggacacaac    2160
cgactccggg gacatgcact ctcgggccct gtggagggac tggtgcagat gcccacacac    2220
acactcagcc cagacccgtt caacaaaccc cgcactgagg ttggccggcc acacggccac    2280
cacacacaca cgtgcacgcc tcacacacgg agcctcaccc gggcgaaccg cacagcaccc    2340
agaccagagc aaggtcctcg cacacgtgaa cactcctcgg acacaggccc ccacgagccc    2400
cacgcggcac ctcaaggccc acgagccgct cggcagcttc tccacatgct gacctgctca    2460
gacaaaccca gccctcctct cacaaggtgc cctgcagcc gccacacaca cacaggcccc     2520
cacacgcagg ggaacacacg ccacgtcgcg tccctggcac tggcccactt cccaatacag    2580
cccttccctg cagctggggt cacatgaggt gtgggcttca ccatcctcct gccctctggg    2640
cctcagggag ggacacggga gacggggagc gggtcctgct gagggccagg tcgctatcta    2700
gggccgggtg tctggctgag tcccggggcc aaagctggtg cccagggcgg gcagctgtgg    2760
ggagctgacc tcaggacatt gttggcccat cccggccggg ccctacatcc tgggccccgc    2820
cacagaggga atcaccccca gaggcccaag cccaggggga cacagcactg accacccccct   2880 tcctgtccag agctgcaact ggaggagagc tgtgcggagg cgcaggacgg ggagctggac    2940
gggctgtgga cgaccatcac catcttcatc acactcttcc tgttaagcgt gtgctacagt    3000
gccaccgtca ccttcttcaa ggtcggccgc acgttgtccc cagctgtcct tgacattgtc    3060
ccccatgctg tcacaaactg tctctgacac tgtcccacag gctgtcccca cctgtccctg    3120
acgctgtccc ccatgctctc acaaactgtc cctgacattg tccccaatgc tgcccccacc    3180
tgtccaacag tgtccccag gctctcccca catgtccccg acactgtccc ccatgctgtc     3240
cccatctgtc cccaacactg tccccccaccc tgtcccccctt tgtccccaac actgtccccc   3300
acagtttcca cctgtccctg acactgtccc ccatgctttc cccacctgtc cctgacacca    3360 tccccccactc tgtcccctat agttcctggc cctgtccccc acgctgtccc ctacagtacc    3420
tggcactgtc cccatgctg tccctcctg tatgaaaccc tgtcccacat gctgtcccca      3480
cctgtccgtg acaatatccc ccacactgtc cccacctgtc cccgacactc tcctccacgt    3540
tgttcttacc taaacccgac actttcctcc atgctgtccc cacccatctc cgacactgta    3600
ccccacgttg tccccacctg tcctcaacac tgtcccccat gctgtcccca cctgtcccca    3660
acactctcct ccatgctgtc cccacctgtc cctgatattg tccccatgc agtctccacc     3720 tgtccccaat gctgtccccc aggctgtacc taccagtaca acactgtccc ccatgctgtc    3780
cccacctgtc cctgacactg tcccccacgc tgtcccctcc tgtcccgac actgtccccc     3840 acactgtccc cacctgtccc caacactatc ctccatgctg tccctcctg tccccacctg     3900 tccctacac tgtcccccat gctgtcccca ccagtcccca aaactttcct ccacactgtc     3960
```

```
cccacctgtc cccaacactg tcccccacgc tatccccctt gtcccgacaa atgtccccac    4020
tgtttcctcc tgttccctcc tatccctgac actgtccgcc atgctgtccc cacctgtccc    4080
tgacactgtc tcccactctg tccctataa tccctgacac tgtccccac gccgtccct    4140 cccgtatgca ccactgtccc ccaagctgtc cccacctgtc ctcaacacag tcccccatgc    4200
tgtccccacc tgtccccaac actctcctcc atgtcccac ctgtccctga tattgtcccc    4260
catgcagtcc ccacctgtcc ccgatgctgt ccccgggct gtacctacca gtccaacact    4320
gtcccccaca ctctccccac ctgtccctga tactgtcccc catgctgtcc ccacctgtcc    4380
cggacactgt tctccacgat ctcccctcct gtccctgaca ctgtccccca cactgtcccc    4440
acctgtcccc aacactatcc tccatcctgt cccaacctgt ctcctacact gtccccatg    4500 ctgtccccac cagtcccaa cactgtcctc catgctgtcc cccatgtccc caacactgtc    4560
ccccatgcta cctcccctgc cctgacaat gtcccactg tttcctgtcc cctcctatcc    4620
ctgacactgt ccccatgct gtccccacct gtccccaca tggtctccac cggtccctga    4680
cactgtctcc cactctgtcc cctataatcc ctgacactgt ccccacacc gtcccctcct    4740 gtatgcacca cggtcccca tgctgtcccc acctgtccct gatgctgtcc tccacacagt    4800
ccccacctct ccctgacact gtcccatct ctccccaaca ctctcctcca tgctgtcctc    4860
aactgtcccc aacactcttc cacactgtgt ctccacctgt ccctgacact gtccccaca    4920 ctgtcctcac ctgtgtctga cactgtcccc cacgctgtcc ccacctgtcc ctgacgctgt    4980
cttctgtgct gtccacatgc tgttggtgcc ctggctctgc tctctatcac caagcctcag    5040
agcaggcagt ggtgaggcca tggcacctgg gtggcatgag gggccggatg ggcctcaggg    5100
gcagggctgt ggcctgcgtg gactgacagg tgggtgggcc ttggggcag agagtggcc    5160 tcagtgccct gaggggtggg tggggctcgg ggcagggct gtggcctcgc tcacccctgt    5220
gctgtgcctt gcctacaggt gaagtggatc ttctcctcgg tggtggacct gaagcagacc    5280 atcatcccg actacaggaa catgatcgga caggggcct agggcaccc tctgcggggt    5340 gtccaggccc gcccagaccc cacacaccag ccatgggcca tgctcagcca ccacccaggc    5400
cacacctgcc cccgacctca ccgccctcaa ccccatggct ctctggcctc gcagttgccc    5460
tctgaccctg acacctga cacgcccccc ttccagaccc tgtgcatagc aggtctaccc    5520
cagacctccg ctgcttggtg cctgcaggc actgggggcc agtgtccc tcagcaggac    5580 gtccttgccc tccggaccac aaggtgctca cacaaagga ggcagtgacc ggtatcccag    5640 gcccccacccc aggcaggagc tggccctgga gccaacccg tccacgccag cctcctgaac    5700
acaggcgtgg tttccagatg gtgagtggga gcatcagccg ccaaggtagg gaagccacag    5760
caccatcagg ccctgttggg gaggcttccg agagctgcga aggctcactc agacggcctt    5820
cctcccagcc cgcagccagc cagcctccat tccgggcact cccgtgaact cctgacatga    5880
ggaatgacgt tgttctgatt tcaagcaaag aacgctgctc tctggctcct gggaacagtc    5940
tcggtgccag caccaccct tggctgcctg cccacactgc tggattctcg ggtggaactc    6000
gacccgcagg acagccagc cccagagtcc gcactgggga gagaagggc caggcccagg    6060 acactgccac ctcccaccca ctccagtcca ccgagatcac tcggagaaga gtctgggcca    6120
tgtggccgct gcaggagccc cacagtgcaa gggtgaggat agcccaagga agggctgggc    6180
atctgcccag acaggcctcc cacagaaggc tggtgaccag gtcccaggcg gcaagactc    6240 agccttggtg gggcctgagg acagaggagg cccaggagca tcggggagag aggtggaggg    6300
acaccgggag agccaggggc gtggacacag ccagaactca tcacagaggc tggcgtccag    6360
```

```
tcccgggtca tgtgcagcag gaacaagcag ccactctggg ggcaccaggt ggagaggcaa    6420
gacgacaaag agggtgcccg tgttcttgcg aaagcgggc tgctggccac gagtgctgga    6480
cagaggcccc cacgctctgc tgccccatc acgccgttcc gtgactgtca cgcagaatct    6540
gcagacagga agggagactc gagcgggagt gcggccagag cctgcctcgg ccgtcaggga    6600
ggactcccgg gctcactcga aggaggtgcc accatttcag ctttggtagc ttttcttctt    6660
cttttaaatt ttctaaagct cattaattgt ctttgatgtt tcttttgtga tgacaataaa    6720 atatccttttt taagtcttgt acttcgtgat gggagccgcc ttcctgtgtc cacgcgcctc    6780
ctgcccccgg tgggaagcac ggtcaggagg aggctggtcc agctgcacct cgggggctcc    6840
ctgcactcgc ccccgcctc ctgcagccac acgcattgcc cgagcgaccc tccctggccc    6900
ctgtcactac atggaccccc ggggcttctc ctctttcta catggatcc                 6949
```

<210> SEQ ID NO 141
<211> LENGTH: 330
<212> TYPE: PRT
<213> ORGANISM: Homo sapiens

<400> SEQUENCE: 141

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

```
                  275                 280                 285
Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 142
<211> LENGTH: 399
<212> TYPE: PRT
<213> ORGANISM: Homo sapiens

<400> SEQUENCE: 142

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Glu Leu Gln Leu Glu Glu Ser Cys
```

```
                    325                 330                 335
Ala Glu Ala Gln Asp Gly Glu Leu Asp Gly Leu Trp Thr Thr Ile Thr
                340                 345                 350

Ile Phe Ile Thr Leu Phe Leu Leu Ser Val Cys Tyr Ser Ala Thr Val
            355                 360                 365

Thr Phe Phe Lys Val Lys Trp Ile Phe Ser Ser Val Val Asp Leu Lys
    370                 375                 380

Gln Thr Ile Ile Pro Asp Tyr Arg Asn Met Ile Gly Gln Gly Ala
385                 390                 395

<210> SEQ ID NO 143
<211> LENGTH: 4608
<212> TYPE: DNA
<213> ORGANISM: Homo sapiens

<400> SEQUENCE: 143
```

| | | | | | |
|---|---|---|---|---|---|
| cctccaccaa | gggcccatcg | gtcttccccc | tggcaccctc | ctccaagagc | acctctgggg | 60 |
| gcacagcggc | cctgggctgc | ctggtcaagg | actacttccc | cgaaccggtg | acggtgtcgt | 120 |
| ggaactcagg | cgccctgacc | agcggcgtgc | acaccttccc | ggctgtccta | cagtcctcag | 180 |
| gactctactc | cctcagcagc | gtggtgaccg | tgccctccag | cagcttgggc | acccagacct | 240 |
| acatctgcaa | cgtgaatcac | aagcccagca | acaccaaggt | ggacaagaaa | gttggtgaga | 300 |
| ggccagcaca | gggagggagg | gtgtctgctg | gaagccaggc | tcagcgctcc | tgcctggacg | 360 |
| catcccggct | atgcagcccc | agtccagggc | agcaaggcag | ccccgtctg | cctcttcacc | 420 |
| cggaggcctc | tgcccgcccc | actcatgctc | agggagaggg | tcttctggct | tttccccgg | 480 |
| ctctgggcag | gcacaggcta | ggtgccccta | acccaggccc | tgcacacaaa | ggggcaggtg | 540 |
| ctgggctcag | acctgccaag | agccatatcc | gggaggaccc | tgcccctgac | ctaagcccac | 600 |
| cccaaaggcc | aaactctcca | ctccctcagc | tcggacacct | ctctcctcc | cagattccag | 660 |
| taactcccaa | tcttctctct | gcagagccca | aatcttgtga | caaaactcac | acatgcccac | 720 |
| cgtgcccagg | taagccagcc | caggcctcgc | cctccagctc | aaggcgggac | aggtgcccta | 780 |
| gagtagcctg | catccaggga | caggccccag | ccgggtgctg | acacgtccac | ctccatctct | 840 |
| tcctcagcac | ctgaactcct | gggggaccg | tcagtcttcc | tcttcccccc | aaaacccaag | 900 |
| gacaccctca | tgatctcccg | gacccctgag | gtcacatgcg | tggtggtgga | cgtgagccac | 960 |
| gaagaccctg | aggtcaagtt | caactggtac | gtggacggcg | tggaggtgca | taatgccaag | 1020 |
| acaaagccgc | gggaggagca | gtacaacagc | acgtaccgtg | tggtcagcgt | cctcaccgtc | 1080 |
| ctgcaccagg | actggctgaa | tggcaaggag | tacaagtgca | aggtctccaa | caaagccctc | 1140 |
| ccagccccca | tcgagaaaac | catctccaaa | gccaaaggtg | ggacccgtgg | ggtgcgaggg | 1200 |
| ccacatggac | agaggccggc | tcggcccacc | ctctgccctg | agagtgaccg | ctgtaccaac | 1260 |
| ctctgtccct | acaggcagc | cccgagaacc | acaggtgtac | accctgcccc | catcccggga | 1320 |
| tgagctgacc | aagaaccagg | tcagcctgac | ctgcctggtc | aaaggcttct | atcccagcga | 1380 |
| catcgccgtg | gagtgggaga | gcaatgggca | gccggagaac | aactacaaga | ccacgcctcc | 1440 |
| cgtgctggac | tccgacggct | ccttcttcct | ctacagcaag | ctcaccgtgg | acaagagcag | 1500 |
| gtggcagcag | gggaacgtct | tctcatgctc | cgtgatgcat | gaggctctgc | acaaccacta | 1560 |
| cacgcagaag | agcctctccc | tgtctccggg | taaatgagtg | cgacggccgg | caagccccg | 1620 |
| ctccccgggc | tctcgcggtc | gcacgaggat | gcttggcacg | tacccctgt | acatacttcc | 1680 |
| cgggcgccca | gcatggaaat | aaagcaccca | gcgctgccct | gggcccctgc | gagactgtga | 1740 |

```
tggttctttc cacgggtcag gccgagtctg aggcctgagt ggcatgaggg aggcagagcg    1800
ggtcccactg tccccacact ggcccaggct gtgcaggtgt gcctgggccg cctagggtgg    1860
ggctcagcca ggggctgccc tcggcagggt gggggatttg ccagcgtggc cctccctcca    1920
gcagcacctg ccctgggctg gccacgggaa agccctagga gccctggggg acagacacac    1980
agcccctgcc tctgtaggag actgtcctgt tctgtgagcg ccctgtcctc cgacctccat    2040
gcccactcgg gggcatgcct agtccatgcg cgtagggaca ggcctccct cacccatcta    2100 cccccacggc actaacccct ggcagccctg cccagcctcg cacccacatg ggacacaac    2160 cgactcctgg ggacatgcac tctcgggccc tgtggaggga ctggtccaga tgcccacaca    2220
cacactcagc ccagacccgt tcaacaaacc ccgcactgag gttggccggc cacacggcca    2280
ccacacacac acgtgcacgc ctcacacacg gagcttcacc cgggcgaacc gcacagcacc    2340
cagaccagag caaggtcctc gcacacgtga acactcctcg gacacaggcc cccacgagcc    2400
ccacgcggca cctcaaggcc cacgagccgc tcggcagctt ctccacttgc tgaccagctc    2460
agacaaaccc agccctcctc tcacaaagtg cccctgcagc cgccacacac acacaggccc    2520
ccacacacag gggaacacac gccacgtcac gtccctggca ctggcccact tcccaataca    2580
gcccttccct gcagctgagg tcacatgagg tgtgggcttc accatcctcc tgccctctgg    2640
gcctcaggga gggacacggg agacggggag tgggtcctgc tgagggccag gcctctatct    2700
agggccgggt gtctggctga gtcccggggc caaagctggt gccagggcg gcagctgtg     2760 gggagctgac ctcaggacac tgttggccca tccggccgg ccctacatc ctgggccccg      2820 ccacagaggg aatcaccccc agaggcccaa gcccaggggg acacagcact gaccaccccc    2880
ttcctgtcca gagctgcaac tggaggagag ctgtgcggag gcgcaggacg gggagctgga    2940
cgggctgtgg acgaccatca ccatcttcat cacactcttc ctgctaagcg tgtgctacag    3000
tgccaccgtc accttcttca aggtgaagtg gatcttctcc tcggtggtgg acctgaagca    3060
gaccatcgtc cccgactaca ggaacatgat aaggcagggg gcctagggcc accctctgcg    3120
gggtgtccag ggccgcccag accccacaca cgagccgtgg gccatgctca gccaccaccc    3180
aggccacacc tgcccctga cctcaccgcc ctcaaccccca tggctctctg gcttcgcagt    3240
cgccctctga gccctgaaac gccccccttc cagaccctgt gcatagcagg tctaccccag    3300
acctccgctg cttggtgcca gggcactggg ggccaggtgt cccctcagca ggacgtccct    3360
gccctctgga ccaccaggtg ctcacacaaa aggaggtaac cggcatccca ggcccccact    3420
caggcaggac ctcgccctgg agccaacccc gtccacgcca gctcctgaa cacaggcatg     3480 gtttccagat ggtgagtggg agcatcagtc gccaaggtag ggaagccaca gcaccatcag    3540
gccctgttgg ggaggcttcc gagagctgcg aaggctcact cagacggcct tcctcccagc    3600
ccgcagccag ccagcctcca ttccgggcac tcccgtgaac tcctgacatg aggaatgagg    3660
ttgttctgat ttcaagcaaa gaacgctgct ctctggctcc tgagaacagt ctcggtgcca    3720
gcaccacccc ttggctgcct gcccacactg ctggattctc gggtggaact cgacccgcag    3780
ggacagccag cccagagtc cgcactgggg agagaagggg ccaggccag  acactgcca      3840 cctcccaccc actccagtcc accgagatca ctcagagaag agcctgggcc atgtggccgc    3900
tgcaggagcc ccagagtgca agggtgagga tagcccaagg aagggctggg catctgccca    3960
gacaggcctc ccacagaagg ctggtgacca ggtcccaggc gggcaagact cagccttggt    4020
ggggcctgag gacagaggag gcccaggagc atcggggaga gaggtggagg gacaccggga    4080
gagccaggag cgtggacaca gccagaactc accacagagg ctggcgtcca gtcccgggtc    4140
```

```
acgtgcagca ggaacaagca gccactctgg gggcaccagg tggagaggca agacgacaaa    4200
gagggtgccc gtgttcttgc gaaagcgggg ctgctggcca cgagtgctgg acagaggccc    4260
ccacgctctg ctgcccccat cacgccgttc cgtgactgtc acgcagaatc cacagacagg    4320
aagggaggct cgagcgggac tgcggccagc gcctgcctcg gccgtcaggg aggactcctg    4380
ggctcactcg aaggaggtgt caccatttca gctttggctt ttcttcttct tttaaatttt    4440
ctaaagctca ttaattgtct ttgatgtttc tttttgatg acaataaaat atccttttta    4500
agtcttgtac ttcgtgatgg gagccacctt cctgtgtcca cgcgcctcct gccccggtg    4560 gaaaacacgg tcaggaggag gctggtccag ctgcacctcg ggggatcc                 4608
```

<210> SEQ ID NO 144
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 145
<211> LENGTH: 399
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

```
Gln Lys Ser Leu Ser Leu Ser Pro Glu Leu Gln Leu Glu Ser Cys
            325                 330                 335

Ala Glu Ala Gln Asp Gly Glu Leu Asp Gly Leu Trp Thr Thr Ile Thr
        340                 345                 350

Ile Phe Ile Thr Leu Phe Leu Leu Ser Val Cys Tyr Ser Ala Thr Val
            355                 360                 365

Thr Phe Phe Lys Val Lys Trp Ile Phe Ser Ser Val Val Asp Leu Lys
    370                 375                 380

Gln Thr Ile Val Pro Asp Tyr Arg Asn Met Ile Arg Gln Gly Ala
385                 390                 395

<210> SEQ ID NO 146
<211> LENGTH: 53
<212> TYPE: PRT
<213> ORGANISM: Homo sapiens

<400> SEQUENCE: 146

Leu Trp Thr Thr Ile Thr Ile Phe Ile Thr Leu Phe Leu Leu Ser Val
1               5                   10                  15

Cys Tyr Ser Ala Thr Val Thr Phe Phe Lys Val Lys Trp Ile Phe Ser
            20                  25                  30

Ser Val Val Asp Leu Lys Gln Thr Ile Val Pro Asp Tyr Arg Asn Met
        35                  40                  45

Ile Arg Gln Gly Ala
    50

<210> SEQ ID NO 147
<211> LENGTH: 34
<212> TYPE: PRT
<213> ORGANISM: Homo sapiens

<400> SEQUENCE: 147

Ala Gly Thr Thr Asp Ala Ala His Pro Gly Arg Ser Val Val Pro Ala
1               5                   10                  15

Leu Leu Pro Leu Leu Ala Gly Thr Leu Leu Leu Leu Glu Thr Ala Thr
            20                  25                  30

Ala Pro

<210> SEQ ID NO 148
<211> LENGTH: 4551
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 148
cctccaccaa gggcccatcg gtcttccccc tggcaccctc ctccaagagc acctctgggg      60
gcacagcggc cctgggctgc ctggtcaagg actacttccc cgaaccggtg acggtgtcgt     120
ggaactcagg cgccctgacc agcggcgtgc acaccttccc ggctgtccta cagtcctcag     180
gactctactc cctcagcagc gtggtgaccg tgccctccag cagcttgggc acccagacct     240
acatctgcaa cgtgaatcac aagcccagca caccaaggt ggacaagaaa gttggtgaga     300
ggccagcaca gggaggggag gtgtctgctg gaagccaggc tcagcgctcc tgcctggacg     360
catcccggct atgcagcccc agtccagggc agcaaggcag ccccgtctgc ctcttcacc     420 cggaggcctc tgcccgcccc actcatgctc agggagaggg tcttctggct ttttccccgg     480
ctctgggcag gcacaggcta ggtgccccta acccaggccc tgcacacaaa ggggcaggtg     540
```

```
ctgggctcag acctgccaag agccatatcc gggaggaccc tgcccctgac ctaagcccac    600
cccaaaggcc aaactctcca ctccctcagc tcggacacct tctctcctcc cagattccag    660
taactcccaa tcttctctct gcagagccca atcttgtga caaaactcac acatgcccac    720
cgtgcccagg taagccagcc caggcctcgc cctccagctc aaggcgggac aggtgcccta    780
gagtagcctg catccaggga caggcccag ccgggtgctg acacgtccac ctccatctct    840
tcctcagcac ctgaactcct ggggggaccg tcagtcttcc tcttcccccc aaaacccaag    900
gacaccctca tgatctcccg gacccctgag gtcacatgcg tggtggtgga cgtgagccac    960
gaagaccctg aggtcaagtt caactggtac gtggacggcg tggaggtgca taatgccaag   1020
acaaagccgc gggaggagca gtacaacagc acgtaccgtg tggtcagcgt cctcaccgtc   1080
ctgcaccagg actggctgaa tggcaaggag tacaagtgca aggtctccaa caaagccctc   1140
ccagccccca tcgagaaaac catctccaaa gccaaaggtg ggacccgtgg ggtgcgaggg   1200
ccacatggac agaggccggc tcggcccacc ctctgccctg agagtgaccg ctgtaccaac   1260
ctctgtccct acagggcagc cccgagaacc acaggtgtac accctgcccc catcccggga   1320
tgagctgacc aagaaccagg tcagcctgac ctgcctggtc aaaggcttct atcccagcga   1380
catcgccgtg gagtgggaga gcaatgggca gccggagaac aactacaaga ccacgcctcc   1440
cgtgctggac tccgacggct ccttcttcct ctacagcaag ctcaccgtgg acaagagcag   1500
gtggcagcag gggaacgtct tctcatgctc cgtgatgcat gaggctctgc acaaccacta   1560
cacgcagaag agcctctccc tgtctccggg taaatgagtg cgacggccgg caagcccccg   1620
ctccccgggc tctcgcggtc gcacgaggat gcttggcacg tacccctgt acatacttcc   1680
cgggcgccca gcatggaaat aaagcaccca gcgctgccct gggcccctgc gagactgtga   1740
tggttctttc cacgggtcag gccgagtctg aggcctgagt ggcatgaggg aggcagagcg   1800
ggtcccactg tccccacact ggcccaggct gtgcaggtgt gcctgggccg cctagggtgg   1860
ggctcagcca ggggctgccc tcggcagggt gggggatttg ccagcgtggc cctccctcca   1920
gcagcacctg ccctgggctg gccacgggaa gccctagga gccctggg acagacacac    1980
agcccctgcc tctgtaggag actgtcctgt tctgtgagcg cccgtcctc cgacctccat   2040
gcccactcgg gggcatgcct agtccatgcg cgtagggaca ggccctccct cacccatcta   2100
cccccacggc actaacccct ggcagccctg ccagcctcg cacccacatg ggacacaac    2160
cgactcctgg ggacatgcac tctcgggccc tgtggaggga ctggtccaga tgcccacaca   2220
cacactcagc ccagacccgt tcaacaaacc ccgcactgag gttggccggc cacacggcca   2280
ccacacacac acgtgcacgc ctcacacacg gagcttcacc cgggcgaacc gcacagcacc   2340
cagaccagag caaggtcctc gcacacgtga acactcctcg gacacaggcc cccacgagcc   2400
ccacgcggca cctcaaggcc cacgagccgc tcggcagctt ctccacttgc tgaccagctc   2460
agacaaaccc agccctcctc tcacaaagtg cccctgcagc cgccacacac acacaggccc   2520
ccacacacag gggaacacac gccacgtcac gtccctggca ctggcccact tcccaataca   2580
gcccttccct gcagctgagg tcacatgagg tgtgggcttc accatcctcc tgccctctgg   2640
gcctcaggga gggacacggg agacggggag tgggtcctgc tgagggccag gcctctatct   2700
agggccgggt gtctggctga gtcccgggc caaagctggt gcccagggcg ggcagctgtg   2760
gggagctgac ctcaggacac tgttggccca tccggccgg ccctacatc ctgggccccg    2820
ccacagaggg aatcaccccc agaggcccaa gcccaggggg acacagcact gaccaccccc   2880
ttcctgtcca gagctgcaac tggaggagag ctgtgcggag gcgcaggacg gggagctgga   2940
```

```
cggggccggc accaccgacg ccgcgcaccc ggggcggtcc gtggtccccg cgttgcttcc      3000
tctgctggcc gggaccctgc tgctgctgga gacggccact gctccctagg gccaccctct      3060
gcggggtgtc cagggccgcc cagacccccac acacgagccg tgggccatgc tcagccacca     3120
cccaggccac acctgccccc tgacctcacc gccctcaacc ccatggctct ctggcttcgc      3180
agtcgccctc tgagccctga aacgcccccc ttccagaccc tgtgcatagc aggtctaccc      3240
cagacctccg ctgcttggtg ccagggcact gggggccagg tgtcccctca gcaggacgtc      3300
cctgccctct ggaccaccag gtgctcacac aaaaggaggt aaccggcatc ccaggccccc       3360
actcaggcag gacctcgccc tggagccaac cccgtccacg ccagcctcct gaacacaggc      3420
atggtttcca gatggtgagt gggagcatca gtcgccaagg tagggaagcc acagcaccat      3480
caggccctgt tggggaggct tccgagagct gcgaaggctc actcagacgg ccttcctccc      3540
agcccgcagc cagccagcct ccattccggg cactcccgtg aactcctgac atgaggaatg      3600
aggttgttct gatttcaagc aaagaacgct gctctctggc tcctgagaac agtctcggtg      3660
ccagcaccac cccttggctg cctgcccaca ctgctggatt ctcgggtgga actcgacccg       3720
cagggacagc cagccccaga gtccgcactg gggagagaag gggccaggcc caggacactg      3780
ccacctccca cccactccag tccaccgaga tcactcagag aagagcctgg gccatgtggc      3840
cgctgcagga gccccacagt gcaagggtga ggatagccca aggaagggct gggcatctgc      3900
ccagacaggc ctcccacaga aggctggtga ccaggtccca ggcgggcaag actcagcctt      3960
ggtggggcct gaggacagag gaggcccagg agcatcgggg agagaggtgg agggacaccg      4020
ggagagccag gagcgtggac acagccagaa ctcaccacag aggctggcgt ccagtcccgg      4080
gtcacgtgca gcaggaacaa gcagccactc tgggggcacc aggtggagag caagacgac       4140 aaagagggtg cccgtgttct tgcgaaagcg gggctgctgg ccacgagtgc tggacagagg      4200
cccccacgct ctgctgcccc catcacgccg ttccgtgact gtcacgcaga atccacagac      4260
aggaagggag gctcgagcgg gactgcggcc agcgcctgcc tcggccgtca gggaggactc      4320
ctgggctcac tcgaaggagg tgtcaccatt tcagctttgg cttttcttct tcttttaaat      4380
tttctaaagc tcattaattg tctttgatgt ttctttttg atgacaataa aatatccttt       4440
ttaagtcttg tacttcgtga tgggagccac cttcctgtgt ccacgcgcct cctgcccccg      4500
gtggaaaaca cggtcaggag gaggctggtc cagctgcacc tcgggggatc c               4551
```

<210> SEQ ID NO 149  
<211> LENGTH: 330  
<212> TYPE: PRT  
<213> ORGANISM: Artificial Sequence  
<220> FEATURE:  
<223> OTHER INFORMATION: Description of Artificial Sequence: Synthetic polypeptide

<400> SEQUENCE: 149

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

```
Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Pro
            100                 105                 110

Glu Leu Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
            195                 200                 205

Pro Ala Pro Ile Glu Lys Thr Ile Ser Lys Ala Lys Ala Cys Pro Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 150
<211> LENGTH: 380
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Glu Leu Gln Leu Glu Glu Ser Cys
                325                 330                 335

Ala Glu Ala Gln Asp Gly Glu Leu Asp Gly Ala Gly Thr Thr Asp Ala
            340                 345                 350

Ala His Pro Gly Arg Ser Val Val Pro Ala Leu Leu Pro Leu Leu Ala
        355                 360                 365

Gly Thr Leu Leu Leu Leu Glu Thr Ala Thr Ala Pro
    370                 375                 380

<210> SEQ ID NO 151
<211> LENGTH: 2061
<212> TYPE: DNA
<213> ORGANISM: Homo sapiens

<400> SEQUENCE: 151
gtacacactg taacttctcc tctcgatgtc ctgccctcgc cacgggcacg gggggagcat      60
gcatttccag gcttggggag acacagaggc aggagagctg gaagaatggg ctcctgcctg     120
cctggtgcca catcctgccc cagctttgag ggctgaatcc tctcagctca gagaagagct     180
tccctagttt tgcaggcgca cggaggcctc ccacccgtac acctgcctct gctctccccc     240
tggccattgc aatgcatgcc cgggatctgg gtttaccctg cagcccgact cctccagggc     300
aggctccttc cgtccttggg tccagcagcc tccccctcc gctgggtact gagcatctga     360
aaagtctcag atagggccct acacctcttc tcccttctca agtgctcagc caggggtgg      420 ggcttgctgc ttgcaaagag cagcccaccc tcctgtactg ccatcctatt gcctttgaag     480
aaggaggtca gcctggacag gtgaactgag ttgccttcag aaaggcctgt ctcaggcagc     540
cgcagcaggc ttcacgatgt ccatgtatcc tgtttgcctg ctgccgtctc tcctctccca     600

```
agagggggagg tctgcgtgtt gagccaggga ggaaggagcc tgcagcctgc tcagggtggt      660
ggctggtgac tgcggggcca gggcttgctg ctgtctctcg gaatgtcctg catgtgggtc      720
tggctgttcc tgctggcact gccctcttct ctctcccctc ctttcccact ctgccctgct      780
tgcccgtcag ggtctccgga tgccctgct ggaggcagaa aagcgttctg tttttatcat       840
cgtccctgtc ttggtcctgt ccgtgctccc catgtgctcc caatcagttg tcttcgttcc      900
tcaacatcag ggaaagaaaa aacagcaaca cttctccctg tcatcagctc tgctgtctcc      960
ttgtcaggcc ttgggacgtt ctctgggctc agtctagggt cgtgcctcat gcctcatgcc     1020
tctctgggaa ggttcccagg ggcgccgcct ccatggttgg ctggtgggtt ttaaagggga     1080
aggttgggag gaggcctgtg gaaggaggag ggccgtccac acccgtgggg caaagcgtgt     1140
tccatgaaac cagtgctgtg cgtgctggga tgaaagcctc ccagcctctc gtgctgaagg     1200
gaaaggtgga ccgaactggc ttagctgctg tggcaatggg gtgggggggtg agtcctaatc    1260 agaaggtggg agaagagaat aacaaaatgg aactccgccc cctgccgcca catttcctta    1320
agttttagga gttggggcct atgagtagaa tttgaaagaa ctaccaaaaa agcttatttt     1380
tggaaattaa gtcagctttg cctgtggttt ggctaggaat aaatatttac ctgtgtgccc     1440
ctacagagat gacacagacc caaagtggga cattgagcaa ggcacaggct ggttcccctc     1500
ctgtcctctg tcctcattct gtgagtgcca ccatcaccag gtactgtggc ctgcagaaat     1560
aaacgaggca ccaaccctgc cctcagggac cccgtgtctt cttagggaca gaggactcag     1620
aaacatctgt gtccccgcat gttaagtgca tgcacacagt gctgaggctt tgcagagaag     1680
ggccatggct ccctgaggag accaagaaag gcacatagaa gtgacttctc agctggccct     1740
tgcaggatcc ctgggtgcct gtacctctcc agtccagctg agcaaggagg ctcaggaatt     1800
aatgaagatg gggcttgtgt agcacgatgg ttctaggcca tccctttcc atggctcaag      1860 tccattgaag gcagcctcca aaatcagggg gttgcctgat cctcctagtg ccacaatccc     1920
agtcctagct agaacttgcc atggttcttc tccctaaaag ttcccagggg acaggagaca     1980
ggtgttgctt ttctaatgga gcgggacctc gcatggacgg ggccctccaa gcctgctaac     2040
accctgttcg cactgactca g                                               2061

<210> SEQ ID NO 152
<211> LENGTH: 2726
<212> TYPE: DNA
<213> ORGANISM: Mus musculus

<400> SEQUENCE: 152
tacgttcaat ggcagtggat cttaaagacc ttttggatct aagaccagaa gccatctctg       60
actcccctct caccttccag tttcttccaa atcctctggg ccagccagag gtctcagatt      120
ctgccctctt gcctgtgcc caccttgttg accactggac agcatatgtg atggctactg       180
ctagtgccag cttcacaaga ggttaacact acggactagc cattcttcct atgtatctgt      240
ttctgcaaat acagccgctt tacttaagtc tcagcacttc ttagtctcct cttttcctct     300
cagtagccca aggggtcatg tcacaaacat ggtgtgaagg gctactttgt caaatgaaaa      360
ggtctatctt gggggggcatt ttttttcttt cttttttttct tgaaacacat tgcccagcaa    420
agccaataaa tttctctcat cattttgttt ctgataaatt cttactattg attgaaatgc     480
ttccctgagg aacattaaat tatgtatgaa tttccattca aagtcatcat gcagcagtgg     540
tatcaagcag gcagcatcta gtgcagaact gagattgtct acagaatgcc tgcttgatgc     600
tcagccttat atcccagtta cggacatgtc tacaaatagc ccttctctta ccatctctcc      660
```

```
cttaacttca tgatgtggta gctgattcct tctgccatca actgaaatgg caaaataaag      720
gaaagcctga atcctgtctc ccctcttagt ttccaaggac acttgcccag aaaaatgcgc      780
cccccccccc ccgtatcccc aggcagcatc caggactttc ttaaatggtt ctctgtacaa      840 tcccacctttt aaaacagtca gtgaccattc tttgtaatca ttactttatt aatggttttc     900 tttttctaaac cacctgcctt tgctgttgta gcttctcaat acatgctctg agacaaatca    960
ttccttatat attccaatat tgctgaaaac tcattaattt ttactaatag ggggttgttt     1020
tctaaagctc aggaaatgac ttgtactccc taagtaggaa atgttgcaaa ccaccatttc     1080
atgatgtaca gttgattcaa ttaagtcagg tctgtgagga ctttggttcc ttatctatat     1140
gtaaataatg ctgataccaa atctttgcta ttcattaaca tgtaatcttg caaataataa     1200
taaatttaac agaaactcaa attgaggtag attcttaagg ataatagctt tcagcctagc     1260
cataaaagaa atgaaaaaat agtctttaaa gatcccaaat tcagaattag taatattaat     1320
tcagatagtc cttcgtaaga ttgaaaaaca tgacttctga tttctcatct ttccaaagtt     1380
agacttgacc ttggtgagat ggcaaagtta aaaaattcct ggggtttaag gatatattgg     1440
ggcaacagtc acagcaacgg tgatgctttt tatatctaaa tcctgtcagg ttttgtttcc     1500
actgagctca ttcattcacc tagggatctc attaaaagta ggggaccggg ctggtgagat     1560
ggctcagcag gtaagagcac ccgactgctc ttccgaaggg cctgagttca atcccagaa      1620 accacatggt ggctcacaac catccgtaac aagatctgac tccctcttct ggtgtgtctg     1680
aagacagcta cagtgtactt acatataata aataaataaa tcttaaaaaa aaaaaaaag     1740 taggggaccc tatcagaggt ctcaatgtgc ctggaaggtc tcccaacatg gctgtgggaa     1800
aatgcctgac aattttttttt caattgcatg tgtgttctcc gagaaaggat aagatgcaag    1860
tttatataag aagcaggatt tacttatact aaaatgcctt acacgtaagg ttcaggtagc     1920
atcgtggcag agagggtaga aagactgtaa gagccagagg accaggatgt ccgctcttag    1980
tgtcttctat atatgaaaga aagctgtacc cgtgaattct caaacagttg tctacatatc     2040
acctgcacaa tggccgttct ggaaatctaa aaaaaacaaa aaacaaacaa acaaataaat     2100
aaataaataa atatcaaaaa atcaaaaacc acccctagat gaaaagctac aagtaattaa    2160
aagctgctaa aaggggggaga atcaattttc tccagagaca agtccctgat aggtcatcca    2220
atttcgggtg atcagcccta agcacataca catataagca atactaaacg gacacagctg    2280
gtctatatac ttacaacttg gggcttgaag gaagttggtg gggaaggggg gagagtagta    2340
atgatgtatg taaatacagt actcatgtac gaaactcccc aaaaataaag aattcttaaa    2400
attattaaaa actggtattc ttgtcttgga ctattttctg aatttttatat taatattttc    2460 atcatcaaaa gactataaaa tgattataat aatgagagaa gttcagatga aacatcaact    2520
gtcttaaatg tagaaaagga aactgacttc aggcagagaa gctaaaaatg ttggcaacct   2580
tgccttggga cttagccacc agtcatttcc tctatataag tcacccatat cccaatttct    2640
gagataattt taaatgttat cactgtgtca aaggtgcagg acatgtatgg aatgcccata    2700
ttaccttctc ttgtctctca ttccag                                         2726

<210> SEQ ID NO 153
<211> LENGTH: 5686
<212> TYPE: DNA
<213> ORGANISM: Homo sapiens

<400> SEQUENCE: 153
gggtgagttg gcagcaacat ctcttggttt aagagttcca gcacagcgat agtactttct       60
```

```
agccacatct cagcaaggaa actaggctat tgccacctgc tcttaagagg cttgaacaca    120
ggtgttaact cctgattgaa atgaacaaag ataggagaag attaggggga aaatctgtat    180
ccttgctgga aaccagggca gtgcacatat aaagagtatg ctgttcactg gatgggaagg    240
aaaaaaactt agaagtgtag tagtcaaagc acacaaacaa ccctaaccca gagtagacat    300
tgctggaaga aagggaagac catgtagcag ctgtgtgaga gaatgaatct taatgataac    360
agcatgatcc cttgctaggg ctgccatcaa aaagtacagg ccttcctcgt tttattgtac    420
ttcgcagatg ttatgctttt tacaaattga acgcttgtgg gaacgctgtg taagcatgtt    480
cgtcggcatc atttatccaa cagcgtgtgt tgacttcgtg tctctgtgta gcattttgat    540
tattctcaca gtatcccaga tgttttcatt attatcatgt ctgtgatagt gatctgtcat    600
cagtgatctt tgatgttact attgtcattg tttggggtcc ctacgaactg cacccatata    660
agacagaaaa cttaatcaat aaatgtgcgt gctttgactg ctccatggac tagacattcc    720
ccttctgtct ccctctcttc aggactccct aatccctgag acacaataat actaaaatga    780
ctccaattaa taaccctaca atagccttta agtgttgaca tgaagggaag agtcatgcat    840
ctcttacttt aaatcaaaag ctagagatga ttaagcttac tgaggaagat acgttgaaaa    900
ccaagatagg ccaaaagcca ttcctcatgt gccaaacagc tagaaagttg taaaggcaaa    960
gtaaaaatac ttgaaggaaa tttaaaatgc tcttccagtg aacacatgta tgataagaag   1020
gtaaaacagc cttattgctg atatggaaga agttttagtg gtctagacat aagatcaaac   1080
tagaaacatt tcctgaagcc aaagcgtaat cctgagcaag gccgtaactc tcttcaattc   1140
tgtgaaggct gacagaagct ggaagctagc agaatttggt tcctgaggtt taaggaaaga   1200
agccctctcc ataacataaa ggtccaaggt gaagcagcca gtgctcatat agaagttgca   1260
gcaagttatc tagaaaatct agctaagatc actgacgaag gtgttacact aaataacaga   1320
ttttccatgt agacaaaaca gccatctatt ggactttcat agctagagag gagaagccaa   1380
tacctgggtt caaagcttca agaacaggc tgactttta ggagctaatg ccgctggtga   1440
ctttgagttg aagccaatgt tcaccgacca ttctaaaaat cctagggccc ttaagcatta   1500
agttaaatat accttgcctg tgtctataaa tggaagaaca aagcctgatg acagaggtat   1560
gtttgcggca tagtttactg aatattttaa gcccactgtt gagatctagt gctcagaaaa   1620
acagattcct ttcaaaatat tactgctcat tgacattgca cctaagcagc caagagctct   1680
aatggagaag gacatggaga tgaatggagt tttcctgcct gctaacaaca gcagccattc   1740
tgcagcccat ggctgaagga gtaattttga ctttcaagtt tcactattta agaaatacat   1800
tttgtaaggt gagtccccac agacagtaat tcctctgatg gatctgaaca aaataagttg   1860
aaaactgctg gaaagaattc atcattctac ataccattaa gaacattcgt gattcatggg   1920
aagagcttaa aatatcaaca ttaataggag tttggtagaa gttaattcca accctcatgg   1980
ctgactttga gaggttcaag acttcagcgg aggaaataac tgaagatgtg gtgaaaatcg   2040
caagagaact acaattagaa gtggagcctg aagacgtgac tgaattgcga caaattcatg   2100
atcaaacttg aacagatgag gagttgcttc tcatgaatca gcagagaaag tggtttttt   2160 gaggtggagt gtcttcctgg tgatgatgac atgagcattg tgaaaatgac cacaaaggat   2220
acagaatatt acaaaaactt aggtgataaa gcagcagcag tatcgggagg attaactcca   2280
attttgaaag cagttcagag ggtaaaatgt tatcaaacag cattgcatgc tagaaaaatc   2340
ttttgtgaaa ggaagagtcc atcaatacag caatttatt gctgtctcag cttaagaaat   2400
tgccacagcc accccagcct tcagcaacca ccaccctgat cagtcagcag ccatcaacct   2460
```

```
tgaggcaaga ccctccacca acaaaaagat tacaaattat tgaaggtcag ataatcttta      2520
gtattttctt atcaataaac cttttttaa agtatgactt tgtttagaca taatgctatt       2580
tcacacttaa tagactaccg tatagtataa acacaacttt tagactcact gagaaatcaa      2640
aaaattcatc tgactcattt gttgtgtat gtgttttatt gtggtggtct ggaactgaac       2700
ctgcaatata tttgaggaat gtctgtaaca cgaagtgggc ggcttaatac aacagaagtt      2760
tttggagttc cattctagag actggaaatc caaaatcaag gttttgggag gccacgctc       2820 cctctgaatc ctgtagggaa ggatccttca ttgcatcttc cagcttctgg agccacaggc     2880
cttccttggc atgtggcagc agaactccaa tttctgtctc tgtcctcata tggccatctt      2940
ccctctgggt ctgtgtcctc atatgctgtt ctctctgtgc atgtctgttt ccaaagtttt      3000
cccttttaat aaggacacca gtcacactgg attagggcct accttcatga cctcaccttta   3060 acttgattgc gtctgcaaag atcgtatttc caaataaggt cacatccaca gggactggag    3120
gttaagactt cagcatactc aggggagaca caattcaacc tataacagag cccctttgaa     3180
aatgtcaggc atcaggtgct cacagcacac ggtccagctg ttggtgctca cccttgctca     3240
gcacacggtg gaggctctgc ctcaatctca ttcttcatgg gaacagctaa gccaggtagc    3300
gaatacgagt tacgtttgtg tcaccacagc agacactgaa aggaagtttg tggtgtccag     3360
cacatttgcc agcataggcc tcacagacca caacacctag aatctgacaa aaattagaat    3420
aaatccgatg tctccttttc tctcttttt taagcatttt taaatacaat tggtaaattt       3480
cctgactgta ccctactcat cttgcattgc tgaataagtg aggaacctct ctatggcatg     3540
aagcagaaaa ccattgagct tatgagaaga aacaggaaat acatgtaaaa gagaccagtc   3600
tgaaaaatca ggagaaattt tacaaaagag atttactgcc aagaaaccag ggaaactttc    3660
agaacactct cctttcata tttgtaacaa gattcaattg tacaaatact tctgtgaaac     3720
tagccatgaa gtgtgtacat gaatgaatat atgtattcag tgtgtttata tatttcattt     3780
catacatgtg atctatatca tatatatata tatatatata tatatatatc acaatgaata     3840
ttgcagaaaa ttaaagcaaa gagtaagaag agttaaccaa atgttccctg aatgcagtgg    3900
gaaaagatga aaaggagaag acaggcaagc acagtggctc acacatgtaa tcccaacata   3960
ttgagaggcc ggggcaagag gatcacttga gcccaggagc tcaagaccag cctggacaac    4020
atggcaaaaa cccatctcta caaaaagta taaaaattag ctgggcatgg cagcatgtga     4080
ctgtagtcac agctaggcag gagaatgaag tgggaggatc acctgagccc aggaggctga    4140
ggcttcagtg agccttgatg gcaaccctgc actccagcct ggatgacaga atgagaccct    4200
gtctcaaaaa aggaaaaaga gaagacatat gtaacacagt gtcaggattc aaaatacatg    4260
tagcaaaaat tccagaaggg taagcaaata agcccatacc tagccatcac tagggaaact   4320
tctgtgtttc agggatagag aaaaaaactc tgattccaga ataaaatgt gaaaatataa     4380 tacccgcaaa agaaataaat ttattgacac cacattgatt ctatattgta taagatatat   4440
tgtataacac taaattgtag aagatagcac ttctcttgag ccaagctaat atgcacacct   4500
agaggctcca ggtacacatt aaaggataag caaagacaca aaaattgtac catttaagta    4560
tgtttcccag gcaattcata agcaaatttt taaaaggag aatgatgaat tccaaaggaa    4620
atctcaatga gataggatgt aggtaaaaag aaaaacaac aataaaaaaa acatacacac    4680
aaaatcttgg caatgtaata ataatttatt aataatctct ctaaactcat agaatatatc    4740
aataaaacta gaaatgtgaa gacagcaaga aagataggc tagacttaca ttacagaaaa    4800
gatgagtaga ctgactatat agagtttgac tctaaaattg agaaagagg tttaaatatg     4860
```

```
tgtcacgtgt atatgtataa tatacatgca cacatataaa atgaaattcc tcactggaaa    4920
aaatattaag tttaatttcc aaattattag aatgactaaa acagttgaat ctatctgttc    4980
catatagtaa ttgagggggga aggaaaagga atagcaagga atccattttt ctcttccacc    5040
agaaataagc tccctcatgt ttgggtcagg tcactttatt cattgctttc tccacatcct    5100
catcattagg catcatgaaa tcaatgaaaa ggcagtgaaa gaatgatgat gaaagctaat    5160
caaatgtatc atttacctca atcgttttgg tttaatcttc ttgttgaaag acaaattctc    5220
ctagacagga tcaaaagcaa catatcttgt atttataaaa aacatgtctc aagtaaaatg    5280
acatagtatt atacacacac acacacatac acacacacac acacattaag ggaaaatgca    5340
gacaaaaaat ggcagaaata atatttagag aaagatagaa tttaagaaaa aaaattgtca    5400
aacaggtctg caaaataatt gttttatttt ggtgccagtt acagtccgca atgaagcgaa    5460
gatattaaga agcaaagtgg gccaggagaa attagagcag aaatatctct ttcaatagtg    5520
agagaatagg aaaagaagt agaaaagctg ggaacaatag gtaaagttta ggctaggcct    5580
tagacttctc ctgcattgta atccctctgg tttgccacat atgcatgctg tcaggaagtt    5640
gatgaggtat gtacagcaca atttattttc catttttttgc ctttag                 5686

<210> SEQ ID NO 154
<211> LENGTH: 1260
<212> TYPE: DNA
<213> ORGANISM: Mus musculus

<400> SEQUENCE: 154
gtgagtatca gggtcgtagg ctgtgaggat ctctacagcc gtgtatattc tctgttcaga      60
aattccctct ggctgaccgt ggcgttttcc gttctaggat gcctctaact atacatccct     120
gtggctgtgg tgtggtgatc cgagggctgc actaacacac agatttctgt ggttgtcact     180
gttcagggcc acagaatgac tgagtcttct ttctatacag tatgcagtag ctggatagtc     240
aggactgggg aaggttgtgt gaggttgact cggtggtacc gctgaggagg aaaagggctt     300
gtccagagca ggcgtgatgt acagcgcaca ttgtttttttt cagcaagtaa tgaaaatctg     360
tgactgagtg accttggggg ctgcggtggt gaggagagct cacgggaatc ctggagcagt     420
gtagctggcg tgtcaaaagc agaaacgcag gagatgggtc agtgcgccga ggcccggagt     480
ttaaatcccc agagcccacg taaaagcctt gcgcagtagc acgcatgcgt aatcctgatg     540
gagcaattag gagaagccgg tggccggcta gcctgtgcag actgtgaaaa cagagcatct     600
gaagctgtgt gaaaggctag ctcgcctgtg ctcctcagat cctgacatac gccatctcga     660
gcaaaagatt aacaatcgat taaaacccac acatgaaaac aaagaaacca gttagctcca     720
gataaaagca aatgccagga aggaaaggag gcagagggca ggggtggagg agcaggtggg     780
agaggatgac gtcagagaaa tctcagtggc cgtgaacaag gaagatattc cagggcttgt     840
tctgaatgtg tgatctttta aaccatgtgg ccctcttagc ctgtgagaaa agtccatttc     900
tagccctgct gaacagagaa gcccagggga gcaaccaact ggccttcggt cactcagcaa     960
ggacctagta gaggctggct ttgaacttga gccctccagg gcacttgacc tctgagcttt    1020
gggaaaacaa gcgaggcagc ttcacgctgt tgtgatctgg acttggatca gggccagtga    1080
ggacagggac agggatgggt gtgataagga cttggtgtgt aagagggaga gttggggaga    1140
caggtgggag ggctatctgt agccaggtaa ccaagggtcc caggggaacc cccagtgtgg    1200
acgcggactg cacatgacac agggcggcct ccccattcat gactgttttt ctccttgcag    1260

<210> SEQ ID NO 155
```

<211> LENGTH: 2627
<212> TYPE: DNA
<213> ORGANISM: Homo sapiens

<400> SEQUENCE: 155

```
gtaaacccac ccatgtcaat gtgtctgttg tcatggcgga ggtggacggc acctgctact      60
gagccgcccg cctgtcccca cccctgaata aactccatgc tccccaagc agccccacgc      120
ttccatccgg cgcctgtctg tccatcctca gggtctcagc acttgggaaa gggccagggc      180
atggacaggg aagaataccc cctgccctca gcctcggggg gccctggca ccccctgag       240
cctttccacc ctggtgtgag tgtgagttgt gagtgtgaga gtgtgtggtg caggaggcct      300
cgctggtgtg agatcttagg tctgccaagg caggcacagc ccaggatggg ttctgagaga      360
tgcacatgcc ccggacagtt ctgagtgagc agtggcatgg ccgtttgtcc ctgagagagc      420
cgcctctggc tgtagctggg agggaatagg gagggtaaaa ggagcaggct agccaagaaa      480
ggcgcaggta gtggcaggag cggcgaggga gtgaggggct ggactccagg gccccactgg      540
gaggacaagc tccaggaggg ccccaccacc ctagtgggtg ggcctcagga cgtcccactg      600
acgcatgcag gaaggggcac ctccccttaa ccacactgct ctgtacgggg cacgtgggca      660
caggtgcaca ctcacactca catatacgcc tgagccctgc aggagcggaa cgttcacagc      720
ccagacccga ttcagaaaaa gccaggggag tccctccca agcccccaag ctcagcctgc      780
tccctaggc ccctctggct tccctgtgtt tccactgtgc acagatcagg caccaactcc       840
acagacccct cccaggcagc ccctgctccc tgcctggcca agtctcccat cccttcctaa      900
gcccaactag gacccaaagc atagacaggg aggggccacg tggggtggca tcagaagcag      960
gccagtgaga cagggcctgc ccagggccct ctgcatgcct ctggcttctg cctggggctc     1020
ccaggagtgt aagaacagtc ccacaaccac tgtggggaca cctggcaccc agactcccac     1080
aaggggcag tggggcccct gctcgtgcct tagacatctt ccgggcctcc ccagggcccc      1140
ccgccttctg gctgcctccc tctgctctca gggccaaggt gaggtggagg ccactgtcac     1200
ccctgagggt ccagtcacca gagggtaatt gagagcaaca ggtcactcgg ggaagccctg     1260
ccacagagaa gccctccagc ccatgggacc caggacctgg cccagggag gggctttaa       1320
agagaggggg aaagagggag aatcaacaga tgaggggctg aaccagcaga cagagatcag     1380
gcagacacat gggtagatcc taggacatat aatgaatgga tgggtggatg gaggattggt     1440
agacggagga tggatgggtg ggtaaatggc tggatggagg atggacagat ggatatatga     1500
tggatggatg aaggacgggt ggatggagga tggatgagtg gatgaatgaa ggatggaaga     1560
tggatggatg gatgggtgga tggactgatg gatgatggat ggatggatgg atggatgatg     1620
gatgatgggg taggcggatg gaggatgaa gggtggatgg aggatggaag atagatggag      1680
gggtgaatgg aggatgggtg gactgacgga ggattgagga tactggggtg ggtgggtggg     1740
tagatctatg gaggataggt gtatggaaga taattggatg gagaattgct ttatgaatgg     1800
atgaatgaag agatggaaaa tagctttata gatggatggg tgaatggatg gatggataga     1860
tggaagaagg atgaatggat ggaaaatagc tttatagata tatgggtgga tatttaagtg     1920
atagccttac attaatagat gaatggagga tgaatggttg ggtgagtggg taggagtgtt     1980
actgatggag gggtggatat acggataata gctttataga tggatggatg gatagatgga     2040
tggaaggata gaaagacagg tgaatgactg gatgtatcag catatgacaa gcaggtacag     2100
ctgtacatgg gaggtctatg ccctgagacc ctgaggaaaa tgaggatgcc cgtgctggtg     2160
gccctcacct ggccctcgct tgtaaccct cagccacatt ccctgggaag gcaacagagg       2220
```

-continued

| | |
|---|---|
| cctctggtct tgcccattca acctttggca cactgagtgt cagacccagg tctctgtctt | 2280 |
| ggacccagat ctccttgagg gtgggtgtgt ctggtcctct ctggcccgg acccagtca | 2340 |
| ctgaatacgt ggctgggact gagacggggt ggggtgggag gggcgggagg gtacctcggg | 2400 |
| ctcaagcttc ccttggagaa gcagatggtg tccactttct gccctgccaa gtctctccct | 2460 |
| gaagtgccct aagaatgtca aagacagaag gtcccagccc ctcacctggg actctgcctc | 2520 |
| ctcatcctcc ctgggggagt ctcaggcctt agatggggac ccagacccca ctgtccccag | 2580 |
| accccaagga agcatagccg ctgttcacac gagtctgggc ctggcag | 2627 |

<210> SEQ ID NO 156
<211> LENGTH: 1937
<212> TYPE: DNA
<213> ORGANISM: Homo sapiens

<400> SEQUENCE: 156

| | |
|---|---|
| gtaaatgacg tactcctgcc tccctccctc ccagggctcc atccagctgt gcagtgggga | 60 |
| ggactggcca gaccttctgt ccactgttgc aatgacccca ggaagctacc cccaataaac | 120 |
| tgtgcctgct cagagcccca ggtacaccca ttcttgggag cgggcagggc tgtgggcagg | 180 |
| tgcatcttgg cacagaggaa tgggccccc aggaggggca gtgggaggag gtgggcaggg | 240 |
| ctgagtcccc ccaggagagg cggtgggagg aggtgggcag ggctgagtg ccactcatcc | 300 |
| atctgccttc gtgtcagggt tatttgtcaa acagcatatc tgcagggact catcacagct | 360 |
| accccgggcc ctctctgccc ccactctggg tctacccct caaggagtc caaagaccca | 420 |
| ggggaggtcc tcagggaagg ggcaagggag ccccacagc cctctctctt gggggcttgg | 480 |
| cttctacccc cctggacagg agccctgca ccccaggta tagatgggca cacaggcccc | 540 |
| tccaggtgga aaacagccc taagtgaaac ccccacacag acacacacga cccgacagcc | 600 |
| ctcgcccaag tctgtgccac tggcgttcgc ctctctgccc tgtcccgcct tgccgagtcc | 660 |
| tggcccagc accggggccg gtggagccga gcccactcac accccgcagc ctccgccacc | 720 |
| ctgccctgtg ggcacaccag gcccaggtca gcagccaggc cccctctcct actgcccccc | 780 |
| accgcccctt ggtccatcct gaatcggccc cagggggatc gccagcctca cacacccagt | 840 |
| ctcgcccact cacgcctcac tcaaggcaca gctgtgcaca cactaggccc catagcaact | 900 |
| ccacagcacc ctgtaccacc accagggcgc catagacacc ccacacgtgg tcacacgtgg | 960 |
| cccacactcc gcctctcacg ctgcctccag cgaggctact gccaagccct tcctctgagc | 1020 |
| catacctggg ccgctggatc ccagagagaa atggagaggc cctcacgtgg tgtcctccag | 1080 |
| tccaaccctc cctgtcaccc tgtcagcagc agcaccccac agccaaacac aggatggatg | 1140 |
| cgtgggctcc atccccact cacccacacc ggaaccccag agcaggctac gtgcccctca | 1200 |
| cagacctcaa acccacatgt gcatctgaca ccccagatcc aaacgctccc ccggtcatg | 1260 |
| cacaccaagg gcacagcacc caccaaatcc acacggaaac acgggcaccg ggcaccccat | 1320 |
| gagcacaaag cccctccatg tctgaagaca gtccctgcac accgtcacag ccatacattc | 1380 |
| agcttcactc tcacgtccca gcccacctgc acccagctct gggcctggag cagcagaaag | 1440 |
| aggtgtgagg gcccgaggcg ggacctgcac ctgctgatga cccgggacca gcaggcagct | 1500 |
| cacggtgttg gggaagggag tggagggcac ccagggcagg agccagaggg accaggctgg | 1560 |
| tgggcgggc cgggccgggg tagggccagg aggcagctct ggacacccac aggcctgggc | 1620 |
| tcatagtcca caccaggaca gccccctcaga gcacccatgc agtgagtccc aggtcttggg | 1680 |
| agccaggccg cagagctcac gcatccttcc gagggccctg agtgaggcgg ccactgctgt | 1740 |

| | |
|---|---:|
| gccgagggt tgggtccttc tctggggagg gcgtggggtc tagagaggcg gagtggaggt | 1800 |
| aaccagaggt caggagagaa gccgtaagga acagagggaa aatggggcca gagtcggggc | 1860 |
| gcagggacga gaggtcagga gtggtcggcc tggctctggg ccgttgactg actcgggacc | 1920 |
| tgggtgccca ccctcag | 1937 |

<210> SEQ ID NO 157
<211> LENGTH: 1301
<212> TYPE: DNA
<213> ORGANISM: Homo sapiens

<400> SEQUENCE: 157

| | |
|---|---:|
| gtaaatgagt gcgacggccg gcaagccccc gctccccggg ctctcggggt cgcgcgagga | 60 |
| tgcttggcac gtaccccgtg tacatacttc ccgggcaccc agcatggaaa taaagcaccc | 120 |
| agcgctgccc tgggcccctg cgagactgtg atggttcttt ccacgggtca ggccgagtct | 180 |
| gaggcctgag tggcatgagg gaggcagagc gggtcccact gtcccacac tggcccaggc | 240 |
| tgtgcaggtg tgcctgggcc gcctagggtg gggctcagcc aggggctgcc ctcggcaggg | 300 |
| tgggggattt gccagcgtgg ccctccctcc agcagcagct gccctgggct gggccacggg | 360 |
| aagccctagg agccctggg gacagacaca cagcccctgc ctctgtagga gactgtcctg | 420 |
| tcctgtgagc gccctgtcct ccgacccgca tgcccactcg ggggcatgcc tagtccatgt | 480 |
| gcgtagggac aggccctccc tcacccatct accccacgg cactaacccc tggcagccct | 540 |
| gcccagcctc gcaccgcat ggggacacaa ccgactccgg ggacatgcac tctcgggccc | 600 |
| tgtggagaga ctggtccaga tgcccacaca cacactcagc ccagaccgt tcaacaaacc | 660 |
| ccgcactgag gttggccggc cacacggcca ccacacacac acgtgcacgc ctcacacacg | 720 |
| gagcctcacc cgggcgaacc gcacagcacc cagaccagag caaggtcctc gcacacgtga | 780 |
| acactcctcg gacacaggcc cccacgagcc ccacgcggca cctcaaggcc cacgagccgc | 840 |
| tcggcagctt ctccacatgc tgaccagctc agacaaaccc agccctcctc tcacaaggtg | 900 |
| cccctgcagc cgccacacac acacaggcc ccacacacag gggaacacac gccacgtcgc | 960 |
| gtccctggca ctgcccact tcccaataca gcccttccct gcagctgggg tcacatgagg | 1020 |
| tgtgggcttc accatcctcc tgccctctgg gcctcaggga gggacacggg agacggggag | 1080 |
| tgggtcctgc tgagggccag gtcgctatct agggccgggt gtgtggctga gtcccggggc | 1140 |
| caaagctggt gcccagggcg ggcagctgtg gggagctgac ctcaggacac tgttggccca | 1200 |
| tcccggccgg gccctacatc ctgggtcctg ccacagaggg aatcacccc agaggcccga | 1260 |
| gcccagcagg acacagcact gaccacctc ttcctgtcca g | 1301 |

<210> SEQ ID NO 158
<211> LENGTH: 1553
<212> TYPE: DNA
<213> ORGANISM: Mus musculus

<400> SEQUENCE: 158

| | |
|---|---:|
| gtaacacctc cctccatccc tcctaggcct ccatgtagct gtggtgggga aggtggatga | 60 |
| cagacatccg ctcactgttg taacaccagg aagctacccc aataaacact cagtgcctga | 120 |
| ttagagccct gggtgcctgt tcttggggaa ggcaggttat gggcagaaat atcttggcct | 180 |
| gaaagaaggg acaccccaag agaaggacag gagtgaagca tggctcaccc atctgtctat | 240 |
| gtgttggata tttgacaaat aggacatcac aggacttcag cataggtacc cctggtcctt | 300 |
| cctgctcttc actggatatc atgcacctga tctctagaga tgcagctaaa atgagccagt | 360 |

```
ctgggaaacc tcagcaccca cctctcagtc ttgcaagctc ctgctcccag acattcctgg     420
atactaaacc ccttcaggta gagaaacagc caaagtcaac atctaggacg caggactcaa     480
catggtcctg ctccttccct ctctactcaa cagccattga ggctgagccc accgcccaa     540 ccgcctgcct tgccaaatga tcacaccagg cctggtgctc ctcgtcttac tacctaaact     600
cactccaacc caaattcatc ccaaggacca gaatgggctg acagcctcat acagtcaggt     660
tcccccatct atgacatgtt ttcacatgca tgcacacaca cacacacaca cacacacaca     720
cacacacaca cacacacaca cacacaggct tcattgagct ctctggttta gcaatagccc     780
aaagcaagcc atacatccat cccagttcca gaaggataag aaaaccagaa ccaagacaca     840
cccacaccta ttccataccc aaccaacagc acatatggct tacacacctg agattagtgg     900
ctcccatcat gtacacacac atgcacacaa aggagcccat acatacccat catttccaga     960
ggtaagtatc taacctttgg atctgagata tctctgagga acaccaatgg cagagtcaac    1020
cagcacctca gcctccagac taaatcctta cattttggcc cacccaagc catgagagat    1080 ggaggagggt ggaggcctga gctgcgggaa agcagagaca ggaagatgga ctgtttggtg    1140
agagtagtaa accagacaat ggggagacta aggcaggagt agagccccta caaggcccag    1200
agtctgctct agagtccatg tgtcctgacc tgcccctcag atgccacaac caagatttct    1260
ggttccagag catgcatgca ggccctagaa atggacctat gagctcagag ccttcctaga    1320
gagccctggg tactctctga acaaaaggca attctgtgta gaggcatcct gtggccaaag    1380
accctaagac agtcatacac acacacacac acacacacac acacacacac aacacacaca    1440
acacacacaa cacaggtagg ttttatcatg ctctttggtt tagcaatagc cctgttgatg    1500
gtgggggata ctgggtcact gtgggcactg gagtagaaag agggaatgaa cag           1553

<210> SEQ ID NO 159
<211> LENGTH: 1354
<212> TYPE: DNA
<213> ORGANISM: Mus musculus

<400> SEQUENCE: 159
gtaaatgagc tcagcacaca caatgctcct gggtcctaat ggacactggc acccatatcc      60
atgcatccct tgtataaata aagcacccag caaagcctgg gaccatgtaa aactgtcctg     120
gttctttcca aggtatagag catagctcac gggctgatag ttctagccag ggttggagga     180
cagccttgtc tttaggtttc tgcactgcag gactcagagc tcatgagtca tcttggcctg     240
aagagtggaa cttagcttta ggcagtatct ttcctttact tcccacaaac cagcagctgc     300
cagacataga gataatccta ggaagcctca aatggagaag cacacaaacc cacctccctc     360
aggctgttcc tctccccagg ccccacttct ttacctaagg gttttctctga gtctattgta    420 gaggcacaca tggccaggga tattccggag acccttagca tccatacact caactcaggc    480
agcttttcac aggtgaggtc tgcacatcca tacagacggc tcactcctgc ctgtgccacg    540
tggggctgag gcacatggct cttgctgccc caagggaggg actattagat agccacagtc    600
atgctgaatc ctgacccatt caaattagcc tgctgaacac catccagtcc atatagcaca    660
tgtatccaca tgcacgtgtg cacacacaca tttaacacac tgggacaact cctctgtgcc    720
ctgcacagca cctacatcca gcaatgtatc accatacaca cggccaaaaa ttcaatgccc    780
acgtttctgc catcacaaac agacacacct ttcctctctg tggccactgc attatatgct    840
caacacaaga cctctgaagc cagatccatc tctggtacct cagggtcatg cttcaacccc    900
acatgaatta tgcaaaccat agccataatg gtctgaatca cttcacattg gaatggtccc    960
```

```
aagatcaggc aagaaaagcc acaggctctg ttgatgactg aaggacagca aagggtcagt    1020
ccagctgtat aaccactgtt gacctgggtc acagaccctg ctgaccctcc atattctctt    1080
gtactgaatg aatgaaaaat gagacaagca tagagggccc ttgcacaatc taggtcagta    1140
tgaggtctac ccgaggcatc attggagtca gctggaggaa gctgagactg atgtcccaga    1200
gggaaaggaa aagaaagaag ctccaggaa gggtctgctg taccagtcag ctggagctc    1260 tctcctctac ttcatgcaaa catgtctgca tcacagggaa tctctcccag caccaaccat    1320
gttgggacaa acactgactg tcctctctgt tcag                                 1354

<210> SEQ ID NO 160
<211> LENGTH: 81
<212> TYPE: DNA
<213> ORGANISM: Homo sapiens

<400> SEQUENCE: 160
tcgcccctgt acctggagat catcatctat tgcacagggg ccttcctcat ctcctgcatg    60
gtggggtcgg tcatcgtcta c                                               81

<210> SEQ ID NO 161
<211> LENGTH: 90
<212> TYPE: DNA
<213> ORGANISM: Mus musculus

<400> SEQUENCE: 161
aagataccat ctattgccac tgggattgtg ggtggcctcc tcttcatagt ggtggtggcc    60
cttgggattg gcctattcat gcgaagacgt                                      90

<210> SEQ ID NO 162
<211> LENGTH: 29
<212> TYPE: PRT
<213> ORGANISM: Homo sapiens

<400> SEQUENCE: 162

Thr His Asp Ala Leu Ile Val Gly Thr Leu Ser Gly Thr Ile Phe Phe
1               5                   10                  15

Ile Leu Leu Ile Ile Phe Leu Ser Trp Ile Ile Leu Lys
            20                  25

<210> SEQ ID NO 163
<211> LENGTH: 81
<212> TYPE: DNA
<213> ORGANISM: Mus musculus

<400> SEQUENCE: 163
cgccttccac tgggggtcac catctcctgc ctctgcatcc cgttgttttg cctgttctgt    60
tacttcagca ttaccaagat t                                               81

<210> SEQ ID NO 164
<211> LENGTH: 63
<212> TYPE: DNA
<213> ORGANISM: Homo sapiens

<400> SEQUENCE: 164
accatcacct tcctcaccct cttcctgctg agcctgttct atagcacagc actgaccgtg    60
acc                                                                   63

<210> SEQ ID NO 165
<211> LENGTH: 87
<212> TYPE: DNA
```

<213> ORGANISM: Homo sapiens

<400> SEQUENCE: 165

```
tggacgtgga ccggcctctg catcttcgcc gcactcttcc tgctcagcgt gagctacagc    60
gccgccatca cgctcctcat ggtgcag                                         87
```

<210> SEQ ID NO 166
<211> LENGTH: 78
<212> TYPE: DNA
<213> ORGANISM: Homo sapiens

<400> SEQUENCE: 166

```
gggctgtgga cgaccatcac catcttcatc acactcttcc tgttaagcgt gtgctacagt    60
gccaccgtca ccttcttc                                                   78
```

<210> SEQ ID NO 167
<211> LENGTH: 78
<212> TYPE: DNA
<213> ORGANISM: Mus musculus

<400> SEQUENCE: 167

```
gagctgtgga ccagtatttg tgtcttcatc accctgttcc tgctcagtgt gagctatggg    60
gccactgtca ccgtcctc                                                   78
```

<210> SEQ ID NO 168
<211> LENGTH: 78
<212> TYPE: DNA
<213> ORGANISM: Mus musculus

<400> SEQUENCE: 168

```
gggctctgga caaccatcac catcttcatc agcctcttcc tgctcagcgt gtgttacagc    60
gcctctgtca cactcttc                                                   78
```

<210> SEQ ID NO 169
<211> LENGTH: 3111
<212> TYPE: DNA
<213> ORGANISM: Homo sapiens

<400> SEQUENCE: 169

```
gtgagtatca agaggcctaa gcaatggtaa tctccactct ccattcttcc cctgtggcca    60
gacacttccc ctggctgagt ctctgggctt ttatatcata ggatgcctct aatggcaatc   120
ctgccattag atacacctgc cgtggtgtat ctgccaggta ggcaggctag ctgcagtaa    180
caaacaagcc cacaatttcc atggcttaac actatgggaa tatatttctt gctcacgtaa   240
caagctaacg tgaatgttgc tggtttgtag gtggtttccc tccctgtaga atctggggga   300
gtgaggttct ttccatcttg tggtgccgtc attctccagg acaaagattc ttacctactt   360
ttgtgtcctg gtttcctttg gcagcctggt gaagcctatg gacctcattt cagaatattt   420
ttaaatacat aaaatcccag cctgggcaat atagtgaaac ccccatctgt acaaaaatta   480
gccaggcatg gtggcatgca cctgtagtcc caggtactgg gaaggctgag gtgggaggat   540
cacttgagcc caggagtttg aggctgcagt gagccgtgat cgtaccactt tactcccacc   600
tgggtgacag agcaagagcc catctctaaa aataaataaa tacaatgaaa taaaataaaa   660
taaatagaac tacagaggaa actaattgta ttgaaatgca gttataaaac atttaaacac   720
attttttaatc tagagatata tgtgcttctt tattaagatc tataaataat aagttctagg   780
ggtagctcgc ataaatactg taatttcaaa gtagataagc ataaataata ctttatgata   840
```

-continued

```
ctgaaattgt gatgtgatat gagaatagct gtgagttttg ttttgctggg gacaggatca    900
gtgatgctgt cattactggg gtctcttccc tccattcttt ttttaaaatt gtattttatt    960
ttatttttaa aattttaaaa taaatagaga cagggtatca ctatgttgcc caggctgctt   1020
ttgacctcct gggctccagt gatcttccca tcttggcttc ccaaagtgct gggattacaa   1080
gtgggagcca gtgttcctgg cccccttcctc cattcttaat ggaaggagat gctaggtgtg   1140
agaggttagg gaaagtaaag atgtaatttc tttcccatcc aagttctcag acccctgaat   1200
tctacctgca gccatgttgg tccatcaacc ccaagtgaag aatccctgct ctagggcccc   1260
accattgtct gtatccagcc agcagaagag gcgtgattat ggagatcaca tctgcttctt   1320
gaaagcagac agcccggaag tgggccgcat cacttcctct caaattctat tggtgaaaat   1380
ggtcacatga ctacacatag ccacaaagga ggctgggaac tttctcactt ggaacctaca   1440
tcccagaaac aactcttttc agtgaggtat cccacaggtc tttcgcagta gaaatattga   1500
ttatctcaca taaaatgaag tcttacaaat ggacctactg gttttgtac agcagccaag    1560
tgatatctct tcccttctgc tgtcttccct tctgccatcc ttcacatggt ggcattgtat   1620
ccttagactt gccacccatg ccctcaggtt ggccgttgca cactgtctta cataaagcag   1680
gaaggaaagg aaaggctgct acgagagagt gtaccttgtg catctctttt ttaatcagga   1740
agcaaacatc tttctagaag cttccctagc aaaattcccc ttacatctca ttggccaaga   1800
ctgttacatg ttacatggtt actgttatta cttgctcatt gcaaggaaga ctgggaactc   1860
aaatgcctgg aaaaggaac aggataatcg tgattggctc aagccttagg gtgggcatgg    1920
ctccctgaca agggagagag gaaaaagctg ttgagtgaag aagactgctt cagtttcccc   1980
atctgtataa tgggaggagt aagggctgtc gtaaaaactc aatgaaagaa gattcttcaa   2040
cgtggtaggt gcagtggcag ctggcagtac cctgaccctg ccaccgcaca gccctctcag   2100
cattgctcat cctgcactgt ggatatcagt tgagccacgt gtctcctgcc ctgggctgtg   2160
agctccatag gcagggtctc catggctgta tctccagaac ccagcacaga accaggtgct   2220
tgggaaagtt ttgaattgat tctcatctgc cattggcatg gggaagggaa ctagcttgta   2280
tgaaacagat aacaatgtat gggaccctca ttcattattt cagcaaatat ttgctgagtt   2340
cctcctacat ggctagccct gtgctagaca ctggggaatc ggcgatgaac aaagcagata   2400
gaaatcccca ctcttgtgga gctgacattc tggagggaga gacaaaaagc aaacatataa   2460
agaaagaaag aaatcacatg gatctggatg acagtgagtg ctgggaagaa aataaaagca   2520
gaggaagggg atggagcgat gggcagggg caacggtagg gagggtgtcg gggaaaactt    2580
tttggagaat gtgacgatga aagtgaacaa ggagaagtca accgtgttga gatgatggca   2640
gctaatgatg tggacaggcc actctgttct gagtgcatta tctattgatt catcatgtca   2700
tcctcgcaac agccctgcac gatcaattct gtcattaacc ccatagtaca gatgaggatg   2760
cggaggcaca gagaagataa gggacttgtc ctgtgtcaca cagcaaggag ccatccggct   2820
cctaagttgg tgcatttgac ttctgtgctt ccggaaagaa agagcagcaa gtttaagatc   2880
tggaggtggc actgagcttt ggaggagcag ggggcaatga ggtggccggt gtgacgagga   2940
ctcaatgtgc aagagggaga gtggtgggga gatgaggtgg aggggtggtc ggcggtcaga   3000
tcgtggaggg tctcggacga gggtcctgac cctgggtctc cagtcctggg aagtggagcc   3060
caggctgtac catggctgac ctcagctcat ggcttcccct cccacttcca g           3111
```

<210> SEQ ID NO 170
<211> LENGTH: 2093
<212> TYPE: DNA

<213> ORGANISM: Homo sapiens

<400> SEQUENCE: 170

```
gtaaatgacg tactcctgcc tccctccctc ccagggctcc atccagctgt gcagtgggga      60
ggactggcca gaccttctgt ccactgttgc aatgacccca ggaagctacc cccaataaac     120
tgtgcctgct cagagcccca ggtacaccca ttcttgggag cgggcagggc tgtgggcagg     180
tgcatcttgg cacagaggaa tgggccccca aggaggggca gtgggaggag gtgggcaggg     240
ctgagtcccc ccaggagagg cggtgggagg aggtgggcag ggctgaggtg ccactcatcc     300
atctgccttc gtgtcaggt tatttgtcaa acagcatatc tgcagggact catcacagct      360
accccgggcc ctctctgccc ccactctggg tctaccccct ccaaggagtc caaagaccca     420
ggggaggtcc tcagggaagg ggcaagggag ccccacagc cctctctctt ggggcttgg      480
cttctacccc cctggacagg agccctgca cccccaggta tagatgggca cacaggcccc     540
tccaggtgga aaacagccc taagtgaaac ccccacacag acacacacga cccgacagcc     600
ctcgcccaag tctgtgccac tggcgttcgc ctctctgccc tgtcccgcct tgccgagtcc     660
tggcccagc accggggccg gtggagccga gcccactcac accccgcagc ctccgccacc     720
ctgccctgtg ggcacaccag gcccaggtca gcagccaggc cccctctcct actgcccccc     780
accgccctt ggtccatcct gaatcggcc ccagggatc gccagcctca cacacccagt       840
ctcgcccact cacgcctcac tcaaggcaca gctgtgcaca cactaggccc catagcaact     900
ccacagcacc ctgtaccacc accagggcgc catagacacc ccacacgtgg tcacacgtgg     960
cccacactcc gcctctcacg ctgcctccag cgaggctact gccaagccct tcctctgagc    1020
catacctggg ccgctggatc ccagagagaa atggagaggc cctcacgtgg tgtcctccag    1080
tccaaccctc cctgtcaccc tgtcagcagc agcacccccac agccaaacac aggatggatg   1140
cgtgggctcc atcccccact cacccacacc ggaaccccag agcaggctac gtgcccctca    1200
cagacctcaa acccacatgt gcatctgaca ccccagatcc aaacgctccc cccggtcatg    1260
cacaccaagg gcacagcacc caccaaatcc acacggaaac acgggcaccg gcacccccat    1320
gagcacaaag cccctccatg tctgaagaca gtccctgcac accgtcacag ccatacattc    1380
agcttcactc tcacgtccca gcccacctgc acccagctct gggcctggag cagcagaaag    1440
aggtgtgagg gccgaggcg ggacctgcac ctgctgatga cccgggacca gcaggcagct    1500
cacggtgttg gggaagggag tggagggcac ccagggcagg agccagaggg accaggctgg    1560
tgggcggggc cgggccgggg tagggccagg aggcagctct ggacacccac aggcctgggc    1620
tcatagtcca caccaggaca gccctcaga gcacccatgc agtgagtccc aggtcttggg     1680
agccaggccg cagagctcac gcatccttcc gagggccctg agtgaggcgg ccactgctgt    1740
gccgaggggt tgggtccttc tctggggagg gcgtggggtc tagagaggcg gagtggaggt    1800
aaccagaggt caggagagaa gccgtaagga acagagggaa aatggggcca gagtcggggc    1860
gcagggacga gaggtcagga gtggtcggcc tggctctggg ccgttgactg actcgggacc    1920
tgggtgccca ccctcaggc tggctggcgg ctccgcgcag tcccagaggg ccccggatag     1980
ggtgctctgc cactccggac agcagcaggg actgccgaga gcagcaggag gctctgtccc    2040
ccaccccgc tgccactgtg gagccgggag ggctgactgg ccaggtcccc cag           2093
```

<210> SEQ ID NO 171
<211> LENGTH: 1285
<212> TYPE: DNA
<213> ORGANISM: Homo sapiens

<400> SEQUENCE: 171

```
gtaaatgagt gccagggccg gcaagccccc gctccccggg ctctcggggt cgcgcgagga      60
tgcttggcac gtaccccgtg tacatacttc ccgggcgccc agcatggaaa taaagcaccc     120
agcgctgccc tgggcccctg cgagactgtg atggttcttt ccacgggtca ggccgagtct     180
gaggcctgag tggcatgagg gaggcagagc gggtcccact gtccccacac tggcccaggc     240
tgtgcaggtg tgcctgggcc gcctagggtg gggctcagcc aggggctgcc ctcggcaggg     300
tgggggattt gccagcgtgg ccctccctcc agcagcacct gccctgggct gggccacgag     360
aagccctagg agccctggg gacagacaca cagcccctgc ctctgtagga gactgtcctg       420
ttctgtgagc gccctgtcct ccgacccgca tgcccactcg ggggcatgcc tagtccatgt     480
gcgtagggac aggccctccc tcacccatct accccacgg cactaacccc tggcagccct      540
gcccagcctc gaacccacat ggggacacaa ccgactccgg ggacatgcac tctcgggccc     600
tgtggaggga ctggtccaga tgcccacaca cacactcagc ccagacccgt caacaaacc      660
ccgcactgag gttggccggc cacacggcca ccacacacac acgtgcacgc ctcacacacg     720
gagcctcacc cggcgaacc gcacagcacc cagaccagag caaggtcctc gcacacgtga      780
acactcctca gacacaggcc cccacgagcc ccacgcggca cctcaaggcc cacgagccgc     840
tcggcagctt ctccacatgc tgaccagctc agacaaaccc agccctcctc tcacaaggtg     900
cccctgcagc cgccacacac acaggggaac acacgccacg tcgcgtccct ggcactggcc     960
cacgtcccaa tacagccctt ccctgcagct ggggtcacat gaggggtggg tttcaccatc    1020
ctcctgccct ctgggctca gggagggaca cgggagacgg ggagtgggtc ctgctgaggg     1080
ccaggtcgct atctagggcc gggtgtctgg ctgagcccca gggccaaagc tggtgcccag    1140
ggtggacagc ttccgggagc tgacctcagg acattgttgg cccatcccgg ccgggcccta    1200
catcctgggc cccgccacag agggaatcac ccccagaggc ccaagcccag ggggacacag    1260
cactgaccac ccccttcctg tccag                                          1285
```

<210> SEQ ID NO 172
<211> LENGTH: 6350
<212> TYPE: DNA
<213> ORGANISM: Mus musculus

<400> SEQUENCE: 172

```
gtaagtcaca actgggtaag agtgtcaagc aaggacagca cttggtacct atgatagaca      60
aatactcctg tttgggaaga ggaggtctgc attgtctaga taagaggaac actgtgctta     120
tctgtttcag tttaaaagac agaactacat aacacttcac cctttctaca acacttagat     180
ttttcagccc tctcctctat ggtgtttcct gaaccctgaa gaaagtgata tagatgttta     240
tttattttct agggccactg ttccaaagaa acaatcacgt attattagca gcttgaccag     300
gtgtgaattt cccccagtat ccacttctgc tccctgtggg atgaagtccc tccataagta     360
aagttgaagg ctgtgggcat aaatgcaaat gcctgtaatc caattttaca agtccatgac     420
atacatttaa caaacaatag cagttacttc tctactggag cctatgaact ccccagctat     480
aggttttttcc cttctgcaga gcagagctta aatccaatag ggaagaagtt ggttgtaccc    540
ataactgcca taccactatt acaccaataa gcacatctta catagcaaga caattagtgt     600
agcactcaaa gtccatgttc aagagagaat gttggcaaca gcctatataa catctcccag     660
cacagaaaag aaaaggaaag gaaaggaaag gaaaggaaag gaaaggaaag gaaaggaaag     720
gaaaggaaag gaaaggaaag gaaaggaaag gaaagaaaag aaaagaaaag aaaagaaaag     780
```

```
aaaagaaaag aaaagaaaag aaaagaaaag aaaagaaaag aaaagaaaag aaaagaaagg    840
aaaagaaagg aaaagaaagg aagacagcca gaaggcagct tccacttcag tcctagccca    900
tgttttctat gtcttacagc caaggttagt gaagtctcta gcagtaggaa tttatcatct    960
acttctggca tgcaagtaaa atcaatggtg ataacttttg tggtttgtgg ctccttggga   1020
gcctccctga caataattt atgcagaggt agcccagctt tgccactggg gcttccatta    1080
aacaaacttt ggattgaggg agtgtctttt tctacctgca cacagtgatt cctatgtttt   1140
aactcttaat gagtcactgt tgtttgttgt tgttgttatt gttgttgtta ttgttgttgt   1200
tgttgttgtt tctatcaacc cagacactat agggctataa gcaggtgga agcatcactg    1260 gctccagctg ttctcagtca tgctcttcct atcaatgttt gtgtaatgac tgccccttt    1320 actgtcggtt ttctatgggt gcctatggat aacgctgggt tgggcgaaac ccttgatggc   1380
agcttttccc actgcttgct tatccatgta ggtgagagca cattcactct cacttgagag   1440
gcttaggcct ttatgaagtc tgcctgacat atgggatagg taggcttata tgcttaccca   1500
tcatgcaccc atgtgctggt accataagca agatcagacc tcacctgttc atgtagcatg   1560
cagaggatca gaatatttca caagaatgcc agaagctctc attactctct ggccttctct   1620
taaagatcac atcctctaac aaagcttacc aaagccacta acatctgagt tagtcctact   1680
caggtacaca tttcttaatg ctccagcaaa agcatctcta cccacttcat tgggcactaa   1740
acaccacttc tcacatgttt agagtttttt gttaagactt taaattatct ttcagtcatg   1800
tctgatgttc atgggcacct cagccagtaa taactgagtg tttctggtgt gtgcaggttt   1860
ttgtctgttt tgtgttgttt atatgccagg aaaaagctgt ttagtacaga tctaattggc   1920
attccccttc cttcatggtg tggatatttc ttttgagtta aaacatcccc tcttgtggca   1980
gggggagggc tagaggtcaa tggaatgatt tcccgagttt ccttggataa atgaaacctt   2040
tgtctcaggg aaggaagaat ggttctactt ctgtttctcc acttcatgat gctgactcta   2100
gcctcttcca tgcccgtgt ctccaggcta tgaaggaatc cagcatgctt ttctctcttc     2160
cttccttatc ttcttcatgg gttccaagtg ggttcctgtg gttccacag gaaaggcttt     2220 ttagcacaaa tctgatctgt actgtctttc ctttatcccc tgccagctct gagacagaaa   2280
gccagcatct ctatcagaat ctctcttttg ccttcagaat cagagaccac tgtgaaaggc   2340
agcatccgtg catcttttt tccattgtac tccttcatta cgtgagcaag attttctaa    2400 gcagatagct tagccttcat cgcacatctt agcacacact gcaaatgtca cacagacagc   2460
ttgctatgcc atcccatgta tactattttc aaggattgca ataccttctc tgatctgaaa   2520
tccattcaag taaaacaaca tgttgcaggt ccaattcaag aggcatgcca cctcatacca   2580
tataaaagaa gatggtcagc aaaaattcct gctctctcag acaactcaga cttgggagca   2640
gaaattccta tcacctctag cagggagtaa acaactacta ctacagctgg aagcatacta   2700
tctcctacca taaagatgc tagcttctct gacaccttag acctgaggca aggaatcctc    2760
tgcctcattt ctttcgtctg ctggaaagcc tacaggacta agggctgctg taagcttgac   2820
acaagcttga ggttgaaagg tgtcagacag gcttcacctg aggggcccta tatatgagtg   2880
tagtgaggat ggaacaggct acgtggggca tcctccggca tcttgtcctc agagtggcct   2940
tcagagccca ggctcaagtc agccatactt ccccacttag actctggaaa tgccacagta   3000
tgtccacaac ctccacaccc agctacacaa aattgagaga gggacctagt gggactgcag   3060
caatcacatg aggccatacc tggaccagcc aagctgccag tataacagtc gtggctctga   3120
gattttgaaa gcttggtctg ttgtctatgc ctcgggatct ttgggatgcc ttaggatcca   3180
```

```
tcgagaaagt tctagagatc atgcctgttt ctggctgcac tgtactgact gagaacaggg   3240
gctacagcac cactgtttct catggcctac ttcctgccag gtggtgcctc attagtactg   3300
aaaggagcct gacctacact tgccccaaat tggccttttc ttttcccctg tggcattggt   3360
tcctcaaagg acactaaggt tttctcttac ttgactccct caggatctct ctacagattt   3420
tcacaggtca ctcctcagag ctagagtcat accagcatga ctatcctctg cccacattca   3480
cacagcatgc ttaggaagtc tgggcatgct ctgtagtcat cttcattagg ttgttcccac   3540
ctgcctctct atctgcccct gccccacttc cccttgttct gcctgttggt ctctccctac   3600
tctgtgcttc acatgtcttg aggtagatac atctgcctga gtcccacata acacttcttc   3660
atcacaccaa cccctgagaa caataatgtt cttagttctg tcgactagca cctcctgact   3720
tgtctctatg atgccattct tcccctccta cccatccatc accctgttgc caaggcactc   3780
tctgagacat cttgtttcta catagataca gaagaacatt tgattaggca tgtaggccat   3840
ggtgaaagaa aaacaccaag taaacttta acatcacaat tttatttaaa actactagag    3900
aggactcagc aatgctcaaa gagactaaat tcccaggtga aaggagatgg gatgttgtat   3960
tctaggcaca gacagacaga gcagtgggac atatgtaatc accaagaaat cagccaaatt   4020
tttaataaac accttagctg ccgagaggga tgagaacaca gaagaatccc aaattctgag   4080
ccaatcacca ctcacttaac ctcccaccca ggacactgct aagcaagaaa cccttcgag   4140 cacagtgtgg gcagaatatc catcttgtac cagctccaag gcctgctgaa tataagggtt   4200
atcccaaagc acctagagcc agaagtcaac tatgataccc cagctccagc acagctcagt   4260
tcccagttcc aaaaaacagg tcttccatgc ctggtggata agatgatatg cacttgtatc   4320 tcaccccag actctacaat ccatgtatat acaatgccta gcatgcaatc agtaattaca    4380
agatacaaat gattgataac caagacagag acagtacatg ggattagacc tgaggtacgg   4440
gaaaggttgg gaaagcattc atagtgtccc ttgctacaag aagtcccaga gctttgcagg   4500
gtgtgagcag attctaacct cccccattgg caagtcttct caaagctgct tctgctacta   4560
gagaaccctc tttcccagcc acctgccact atttatcact tatctgagtt ttccccatga   4620
ttctaggatg ctaccacctc ctgcctgagt cagacggtcc ttccaggaga cctgatggtc   4680
ctgcccttgc ctgagacctt tctaggctga atggtcatca tgtccactgt ctggttagct   4740
tggttgcctc tgtgttaagt tgcttcatac tacatgtagc aaggaaagtt acctttccac   4800
ttctcaggac actgtaaaga agcacttctg taaattatag tgagaaacga tcaataataa   4860
atgaaatgaa caaacataaa cctctcttat ctctatggga cctgccctaa ggcctcttgt   4920
ggatgcctga aaccttgagt gttcttaagc catgtgtcac ttcagtcatt aacctgtggc   4980
tgaggtggat cctgactgac aaacagacag gcatgtagac agcttgaagc ctggacaaag   5040
agaaggttga cgttccaggc aaagcaagag cctatcacat tgttccaaag tgtgtgattt   5100
agaatcagaa gatttcttgt ttaaaatata ctcaaaaagt tataaatat cagccaggac    5160 tagtcataaa gcttaaatct gagagagaga gagagagaga gagagagaga gagaggtgtt   5220
catgtatata catatgtgtg tgtgtgtata tatatgtatg tatatgtatg tatatgtgta   5280
tattggtgtt tgggtgtcag attccctgga attaaagtta taaacagtta tgagctgcaa   5340
agtaggcttt ccaatgtctt gttctccaac cataggtaat tgaaactgga aactacaggt   5400
aaaggaggct gccaagtgtt tcttattatg ctaagattca gtgttctaca atattcacat   5460
gatttcactt tgatatggtg aaatgccttt aggccaacgc atccacagac ttcacagtga   5520
ccccagctga gcttacatat aatgtcaaac agcacttgtt gaatagatac ccaggcagcc   5580
```

```
ctgtgaccca tggtgttttc cttaattctt cccatctgcc ttggactttc acaccttgag      5640
ttgagatgtg ctttctgtag aaatgtattt ccctaggtct gtacatcagc caccacccctt     5700 tctgatcttg gaccatactt cagtctccag ctgggatatt catatgcatg cttagatatg      5760
gcataaccat cgttaacgtc ttctgttacc tttaggatta agttaccgta gctaggatgc      5820
tttccaatct ctccctccat ttgcaaaggc tcagggttcc ttctgactct ggagtagtac      5880
tctttcccaa tgagtgcacc atgaccacta ttcttcctta gaatgttact cccctttctc     5940 tgccttttc atggcacatc tttctgagaa aacctacctg gtctagctgc tctttctggg       6000
tcttcttaag tagtaaccta actcctgcac catccgtgtg gcagtgacat agatccacat      6060
caggtttgga ttcagatatt ccaatcccat gcagaccaat ctatgtgtga gattccagga     6120
tccagcaggc tggggcatgg gttgaggggt aggattcttt ggggcaaagt ggttagtagg     6180
cacttgggac tggaagtgat aagtattagc gggaggaggg catatgatca aaacattgct    6240
gctggatgtg aaagctgtac cttcaggttc agtgttcagg agaccaggtt aataagaaat    6300
gatctttctg tagggtggag accttctcat gagcactagt tcttccctag                6350

<210> SEQ ID NO 173
<211> LENGTH: 1739
<212> TYPE: DNA
<213> ORGANISM: Mus musculus

<400> SEQUENCE: 173 gtaaccctc cctccatccc tcctaggcct ccatgtagct gtggtgggga aggtggatga       60
cagacatccg ctcactgttg taacaccagg aagctacccc aataaacact cagtgcctga     120
ttagagccct gggtgcctgt tcttggggaa ggcaggttat gggcagaaat atcttggcct     180
gaaagaaggg acaccccaag agaaggacag gagtgaagca tggctcaccc atctgtctat    240
gtgttggata tttgacaaat aggacatcac aggacttcag cataggtacc cctggtcctt    300
cctgctcttc actggatatc atgcacctga tctctagaga tgcagctaaa atgagccagt     360
ctggaaaacc tcagcaccca cctctcagtc ttgcaagctc ctgctcccag acattcctgg     420
atactaaacc ccttcaggta gagaaacagc caaagtcaac atctaggacg caggactcaa    480
catggtcctg ctccttccct ctctactcaa cagccattga ggctgagccc accgccccaa     540
ccgcctgcct tgccaaatga tcacaccagg cctggtgctc ctcgtcttac tacctaaact    600
cactccaacc caaattcatc ccaaggacca gaatgggctg acagcctcat acagtcaggt    660
tcccccatct atgacatgtt ttcacatgca tgcacacaca cacacacaca cacacacaca    720
cacacacaca cacacacaca cacacaggct tcattgagct ctctggttta gcaatagccc    780
aaagcaagcc atacatccat cccagttcca gaaggataag aaaaccagaa ccaagacaca    840
cccacaccta ttccataccc aaccaacagc acatatggct tacacacctg agattagtgg     900
ctcccatcat gtacacacac atgcacacaa aggagcccat acatacccat catttccaga    960
ggtaagtatc taacctttgg atctgagata tctctgagga acaccaatgg cagagtcaac   1020
cagcacctca gcctccagac taaatcctta cattttggcc caccccaagc catgagagat    1080
ggaggagggt ggaggcctga gctgcgggaa agcagagaca ggaagatgga ctgtttggtg    1140
agagtagtaa accagacaat ggggagacta aggcaggagt agagccccta caaggcccag    1200
agtctgcttt agagtccatg tgtcctgacc tgccctcag atgccacaac caagatttct    1260
ggttccagag catgcatgca ggccctgaaa atggacctat gagctcagag ccttcctaga    1320
gagccctggg tactctctga acaaaaggca attctgtgta gaggcatcct gtggccaaag    1380
```

-continued

```
accctaagac agtcatacac acacacacac acacacacac aacacacaca    1440
acacacacaa cacaggtagg ttttatcatg ctctttggtt tagcaatagc cctgttgatg    1500
gtgggggata ctgggtcact gtgggcactg gagtagaaag agggaatgaa cagtcagtgg    1560
ggaaaggaca tctgcctcta gggctgaaca gagactggag cagtctcaga gcaggtggga    1620
tggggacctc tgccactcta gcttcatcag aactgcatga gacaagtatg gggtctaccc    1680
cctccccact gtcacctgga gtctgtgggaa gctaactggc tggtcccacc ccatcccag    1739

<210> SEQ ID NO 174
<211> LENGTH: 93
<212> TYPE: DNA
<213> ORGANISM: Homo sapiens

<400> SEQUENCE: 174
ttcgagcagc acctcctgct gggcgtcagc gtttcctgca ttgtcatcct ggccgtctgc    60
ctgttgtgct atgtcagcat caccaagatt aag    93

<210> SEQ ID NO 175
<211> LENGTH: 78
<212> TYPE: DNA
<213> ORGANISM: Homo sapiens

<400> SEQUENCE: 175
gggctgtgga cgaccatcac catcttcatc acactcttcc tgctaagcgt gtgctacagt    60
gccaccgtca ccttcttc    78

<210> SEQ ID NO 176
<211> LENGTH: 84
<212> TYPE: DNA
<213> ORGANISM: Mus musculus

<400> SEQUENCE: 176
ggcctgtggc ccacaatgtg caccttcgtg gccctcttcc tgctcacact gctctacagt    60
ggcttcgtca ccttcatcaa ggta    84
```

POLYPEPTIDE PRODUCING CELLS

This application is the National Stage of International Application No. PCT/EP2007/004313 filed May 15, 2007, which claims the benefit of EP 06010146.6, filed May 17, 2006, which is hereby incorporated by reference in its entirety.

The current invention is in the field of polypeptide production. It describes a nucleic acid comprising an alternatively spliceable nucleic acid, cells comprising this nucleic acid, a method for the isolation of cells expressing a heterologous polypeptide, which utilizes a nucleic acid comprising a first nucleic acid encoding a heterologous polypeptide, a second nucleic acid comprising an alternatively spliceable nucleic acid, and a third nucleic acid encoding at least a fragment of a transmembrane domain or a signal peptide for a GPI-anchor, and also a method for the production of heterologous polypeptides.

BACKGROUND OF THE INVENTION

Expression systems for the production of recombinant polypeptides are well-known in the state of the art and are described by, e.g., Marino, M. H., Biopharm. 2 (1989) 18-33; Goeddel, D. V., et al., Methods Enzymol. 185 (1990) 3-7; Wurm, F., and Bernard, A., Curr. Opin. Biotechnol. 10 (1999) 156-160. For the production of polypeptides and proteins used in pharmaceutical applications preferably mammalian host cells such as CHO cells, BHK cells, NS0 cells, Sp2/0 cells, COS cells, HEK cells, PER.C6® cells and the like are employed. The nucleic acid encoding the polypeptide is preferably introduced into the host cell comprised in a nucleic acid, such as, for example, an expression vector. The essential elements of an expression vector are a prokaryotic plasmid propagation unit, e.g. for *Escherichia coli* comprising an origin of replication and a selection marker, a eukaryotic selection marker, and one or more expression cassettes for the expression of the structural gene(s) of interest each of them comprising a promoter, a structural gene, and a transcription terminator including a polyadenylation signal. For transient expression in mammalian cells a mammalian origin of replication, such as the SV40 Ori or OriP from EBV, may be included. As a promoter a constitutive or inducible promoter can be selected. For optimized transcription a Kozak sequence may be included in the 5' untranslated region. For mRNA processing, in particular transcription termination and pre-mRNA splicing, mRNA splicing signals, depending on the organization of the structural gene (exon-intron-organization), may be included as well as a polyadenylation signal.

Expression of a gene is performed either as transient or permanent expression. The polypeptide(s) of interest may be a secreted polypeptide, containing an N-terminal extension (also known as the signal sequence), which is necessary for the transport/secretion of the polypeptide through the cell and into the extracellular medium, or may be a cytosolic polypeptide.

For the large scale production of a polypeptide a high producer cell line has to be established. After the transfection of a host cell line, such as CHO cells, NS0 cells, Sp2/0 cells, BHK cells, COS cells, PER.C6® cells, or HEK cells, in general a plurality of clones with different characteristics are obtained due to, for example, the broad difference of polypeptide expressed from transiently transfected or stably integrated plasmids. For selection purposes the nucleic acid introduced into cells possesses additionally a selectable marker, e.g. a gene conferring resistance against an otherwise fatal substance.

After transfection and by growth in an appropriate selective medium a high producer clone has to be isolated. This is time consuming and consequently expensive. Several methods have been developed to handle this problem.

One of these methods is gene amplification. Therein cells deficient of the enzyme dihydrofolate reductase (DHFR) are transfected with a vector/plasmid which contains a first expression cassette for the expression of the DHFR protein and a second expression cassette for the expression of a heterologous polypeptide of interest. By using a culture medium depleted of glycine, hypoxanthine, and thymidine selective growth conditions are established. For amplification a DHFR inhibitor, methotrexate (MTX), is added (Kaufman, R. J., et al., J Mol. Biol. 159 (1982) 601-621; U.S. Pat. No. 4,656,134).

Alternatively reporter molecules, such as chloramphenicol-acetyl-transferase, luciferase, green fluorescent protein, or beta-galactosidase, can be fused to the heterologous polypeptide for which a high producer cell line is desired and used as an indirect selectrion marker. The selection takes place in the presence of an added exogenous substrate or cofactor.

A further method for the identification of a high producer clone is a linked transcription of a selectable marker gene and a structural gene encoding a heterologous polypeptide via an internal ribosome entry site (IRES). With this design the expression of the heterologous polypeptide can be correlated with the expression of the selectable marker.

Human immunoglobulins are produced by specialized lymphocytes, the B cells. These cells do not only secrete immunoglobulins (sIg) they also present immunoglobulins on their outer cell membrane as plasma-membrane-bound immunoglobulins (mIg). These mIg's play an important role in the beginning of an immunological response. The presented plasma-membrane-bound immunoglobulins have the function of cellular receptors of their corresponding antigen.

Beginning in 1980 articles dealing with the origin of secreted and plasma-membrane-bound forms of immunoglobulins were published. Early et al. (Early, P., et al., Cell 20 (1980) 313-319) reported that in mice two species of mRNA which encode the heavy chain of immunoglobulins originate from the same primary transcript of a single immunoglobulin μ-gene. The formation of the secreted (sIg) and the plasma-membrane-bound (mIg) forms results from alternative splicing of the heavy chain pre-mRNA. For the sIg isoform all exons coding for the domains of the immunoglobulin and the intron following the exon encoding the C-terminal domain are retained in the mRNA and the polyadenylation signal locates downstream of the stop codon in the intron is used for cleavage and polyadenylation of the primary transcript. For the mIg isoform an alternative 5' splice donor site after the exon encoding the C-terminal domain of the secreted form (i.e. CH3 or CH4, respectively) links the constant region with the downstream exons M1 and M2 encoding a transmembrane domain. In this case the sequence encoding the terminal amino acids and the stop codon of the secreted form, as well as the adjacent intronic polyadenylation signal for the sIg form are removed by the splicing along with the intron.

For example, the ratio between the mRNA encoding the secreted immunoglobulin heavy chain form and the mRNA encoding the plasma-membrane-bound immunoglobulin heavy chain form is of from 10:1 to 100:1. This ratio is established mainly during pre-mRNA splicing. Translational and post-translational control mechanisms contribute only to a minor part (see e.g. Xiang, S. D., et al., Immun. Cell Biol. 79 (2001) 472-481).

The immunoglobulin bound to the cell's plasma-membrane has the same amino acid sequence and secondary structure as its secreted analogue. The difference is a C-terminal extension of the sIg's heavy chain comprising a transmembrane domain. This transmembrane domain has in general a length of between approx. 40 and approx. 75 amino acid residues. For murine and human immunoglobulins the transmembrane domain can be subdivided into three distinct structural regions: an N-terminal extracellular region of 13-67 amino acid residues, a central conserved transmembrane stretch of 25 amino acid residues, and a C-terminal cytoplasmatic region of 3-28 amino acid residues (Major, J. G., et al., Mol. Immunol. 33 (1996) 179-187).

Expression vectors comprising an amplifiable selectable gene, a fluorescent protein gene, and a gene encoding a desired product in a manner that optimizes transcriptional and translational linkage is reported in WO 01/04306. In WO 01/38557 a method for screening multiply transformed/transfected cells to identify cells expressing at least two peptides or proteins of interest is reported. These two peptides/proteins are linked via an IRES (internal ribosome entry site) to a fluorescent marker gene.

Transgenic animals and cells that comprise an imaging marker transgene are reported in US patent application 2003/0033616. US patent application 2005/0032127 reports a method for the non-invasive selection of single living cells under gentle conditions from mixtures of cells or cell cultures with respect to a specific production performance by fluorescence-microscopic detection methods. A method for identifying and isolating cells which produce secreted proteins is reported in US patent application 2002/0168702.

An expression vector consisting of a gene coding for a protein of interest which is functionally linked to a hamster promoter, a gene which codes for a fluorescent protein, and preferably an amplifiable selection marker gene is reported in US patent application 2004/0148647.

SUMMARY OF THE INVENTION

The current invention comprises a nucleic acid comprising in 5' to 3' direction
 a) a first nucleic acid encoding a heterologous polypeptide without an in frame translational stop codon,
 b) a second nucleic acid beginning with a 5' splice donor site and terminated by a 3' splice acceptor site comprising an in frame translational stop codon and a polyadenylation signal, and
 c) a third nucleic acid encoding
  i) at least a fragment of a transmembrane domain, or
  ii) a signal peptide for a GPI-anchor.

Further aspects of the current invention are a vector suitable for eukaryotic cells comprising the nucleic acid of the invention and a eukaryotic cell comprising at least one nucleic acid according to the invention.

The current invention also comprises a method for selecting a eukaryotic cell expressing a heterologous polypeptide, whereby the method comprises
 a) transfecting a eukaryotic cell with a nucleic acid comprising in 5' to 3' direction
  i) a first nucleic acid encoding a heterologous polypeptide without an in frame translational stop codon,
  ii) a second nucleic acid beginning with a splice donor site and terminated by a splice acceptor site comprising an in frame translational stop codon and a polyadenylation signal,
  iii) a third nucleic acid encoding
   iiia) at least a fragment of a transmembrane domain, or
   iiib) a signal peptide for a GPI-anchor,
 b) culturing of said transfected cell under conditions suitable for the production of pre-mRNA from said nucleic acid, processing of said pre-mRNA, and translation of said processed mRNA into a polypeptide, wherein said transfected cell produces soluble heterologous polypeptide and plasma-membrane-bound heterologous polypeptide by alternative splicing of said pre-mRNA, and
 c) selecting a cell with plasma-membrane-bound heterologous polypeptide to be said cell expressing a heterologous polypeptide.

In one embodiment the method of the invention is for selecting a eukaryotic cell expressing an immunoglobulin, whereby the method comprises
 a) transfecting a eukaryotic cell with a nucleic acid comprising in 5' to 3' direction
  i) a first nucleic acid encoding at least a fragment of an immunoglobulin heavy chain without an in frame translational stop codon,
  ii) a second nucleic acid beginning with a splice donor site and terminated by a splice acceptor site comprising an in frame translational stop codon and a polyadenylation signal,
  iii) a third nucleic acid encoding
   iiia) at least a fragment of a transmembrane domain, or
   iiib) a signal peptide for a GPI-anchor,
 b) culturing of said transfected cell under conditions suitable for the production of pre-mRNA from said nucleic acid, processing of said pre-mRNA, and translation of said processed mRNA into an immunoglobulin heavy chain, wherein said transfected cell produces soluble immunoglobulin heavy chain and plasma-membrane-bound immunoglobulin heavy chain by alternative splicing of said pre-mRNA, and
 c) selecting a cell with plasma-membrane-bound immunoglobulin heavy chain to be said cell expressing an immunoglobulin.

The current invention further comprises a method for the production of a polypeptide encoded by a nucleic acid according to the invention, by
 a) providing a eukaryotic cell,
 b) transfecting said eukaryotic cell with a nucleic acid according to the invention,
 c) culturing said transfected cell under conditions suitable for the expression of said nucleic acid,
 d) recovering said polypeptide from the culture medium or the cytoplasm of said cell.

The present invention further comprises a nucleic acid comprising in 5' to 3' direction
 a) a first multiple cloning site,
 b) a nucleic acid beginning with a 5' splice donor site and terminated by a 3' splice acceptor site, wherein
  i) said nucleic acid comprises a translational stop codon and a polyadenylation signal, and
  ii) said nucleic acid is not constitutively removed during pre-mRNA processing,
 c) a second multiple cloning site.

The invention further comprises a vector comprising the not constitutively removed nucleic acid according to the invention.

DETAILED DESCRIPTION OF THE INVENTION

The current invention comprises a method for selecting a eukaryotic cell expressing a heterologous polypeptide or protein, whereby the method comprises a) transfecting a eukaryotic cell with a nucleic acid comprising in 5' to 3' direction
   i) a first nucleic acid encoding a heterologous polypeptide or protein without a translational stop codon,
   ii) a second nucleic acid beginning with a 5' splice donor site and terminated by a 3' splice acceptor site comprising an in frame translational stop codon and a polyadenylation signal,
   iii) a third nucleic acid encoding
      iiia) at least a fragment of a transmembrane domain, or
      iiib) a signal peptide for a GPI-anchor,
b) culturing of said transfected cell under conditions suitable for the production of pre-mRNA from said nucleic acid, processing of said pre-mRNA, and translation of said processed mRNA into a polypeptide or protein, wherein said transfected cell produces soluble heterologous polypeptide or protein and plasma-membrane-bound heterologous polypeptide or protein by alternative splicing of said pre-mRNA,
c) selecting a cell with plasma-membrane-bound heterologous polypeptide or protein to be said cell expressing a heterologous polypeptide or protein.

Useful methods and techniques for carrying out the current invention are described in e.g. Ausubel, F. M. (ed.), Current Protocols in Molecular Biology, Volumes I to III (1997); Glover, N. D., and Hames, B. D., ed., DNA Cloning: A Practical Approach, Volumes I and II (1985), Oxford University Press; Freshney, R. I. (ed.), Animal Cell Culture—a practical approach, IRL Press Limited (1986); Watson, J. D., et al., Recombinant DNA, Second Edition, CHSL Press (1992); Winnacker, E. L., From Genes to Clones; N. Y., VCH Publishers (1987); Celis, J., ed., Cell Biology, Second Edition, Academic Press (1998); Freshney, R. I., Culture of Animal Cells: A Manual of Basic Technique, second edition, Alan R. Liss, Inc., N.Y. (1987).

The use of recombinant DNA technology enables the production of numerous derivatives of a polypeptide. Such derivatives can, for example, be modified in individual or several amino acid positions by substitution, alteration, exchange, deletion or insertion. The modification or derivatisation can, for example, be carried out by means of site directed mutagenesis. Such modifications can easily be carried out by a person skilled in the art (see e.g. Sambrook, J., et al., Molecular Cloning: A laboratory manual (1999) Cold Spring Harbor Laboratory Press, New York, USA; Hames, B. D., and Higgins, S. G., Nucleic acid hybridization—a practical approach (1985) IRL Press, Oxford, England).

Within the scope of the present invention some of the terms used are defined as follows:

A "nucleic acid" as used herein, refers to a polynucleotide molecule, for example to types of DNA and/or RNA. This polynucleotide molecule can be a naturally occurring polynucleotide molecule or a synthetic polynucleotide molecule or a combination of one or more naturally occurring polynucleotide molecules or fragments thereof with one or more synthetic polynucleotide molecules. Also encompassed by this definition are naturally occurring polynucleotide molecules in which one or more nucleotides have been changed, e.g. by mutagenesis, deleted or added. The nucleic acid can either be isolated, or integrated in another nucleic acid, e.g. in an expression vector or the chromosome of a eukaryotic host cell. A nucleic acid is likewise characterized by its nucleic acid sequence consisting of individual nucleotides. It is known in the art to deduce an amino acid sequence from the corresponding encoding nucleic acid and likewise to derive a corresponding nucleic acid from the encoded amino acid sequence. Thus an amino acid sequence is likewise characterized by its nucleic acid. Likewise is a nucleic acid given by a corresponding amino acid sequence.

The expression "plasmid" or "vector" which is used interchangeably within this application include e.g. shuttle and expression plasmids as well as transfection plasmids. Typically, the plasmid will also comprise an origin of replication (e.g. the ColE1 and oriP origin of replication) and a selectable marker (e.g. an ampicillin or tetracycline resistance gene) for replication and selection, respectively, of the plasmid in bacteria.

An "expression cassette" refers to a construct that contains the necessary regulatory elements for expression of at least the contained structural gene in a cell. Optionally additional elements are contained which enable the secretion of the expressed polypeptide or protein.

A "gene" denotes a segment e.g. on a chromosome or on a plasmid, which is necessary for the expression of a polypeptide or protein. Beside the coding region the gene comprises other functional elements including a promoter, one or more introns and/or exons, and one or more terminators.

The term "structural gene" as used within this application denotes the coding region of a gene, i.e. the exons, without a signal sequence, but with intervening introns.

A "selectable marker" denotes a gene that allows cells carrying the gene to be specifically selected for or against, in the presence or absence of a corresponding selection agent. A useful positive selectable marker is an antibiotic resistance gene. This selectable marker allows the host cell transformed with the gene to be positively selected for in the presence of the corresponding antibiotic; a non-transformed host cell would not be capable to grow or survive under the selective culture conditions, i.e. in the presence of the selection agent, in a selective medium. Selectable markers can be positive, negative or bifunctional. Positive selectable markers allow selection for cells carrying the marker, whereas negative selectable markers allow cells carrying the marker to be selectively eliminated. Typically, a selectable marker will confer resistance to a drug or compensate for a metabolic or catabolic defect in the host cell. Selectable markers useful with eukaryotic cells include, e.g., the genes for aminoglycoside phosphotransferase (APH), such as the hygromycin phosphotransferase (hyg), neomycin and G418 APH, dihydrofolate reductase (DHFR), thymidine kinase (tk), glutamine synthetase (GS), asparagine synthetase, tryptophan synthetase (selective agent indole), histidinol dehydrogenase (selective agent histidinol D), and genes encoding resistance to puromycin, bleomycin, phleomycin, chloramphenicol, Zeocin, and mycophenolic acid. Further marker genes are described in WO 92/08796 and WO 94/28143.

"Regulatory elements" as used herein, refer to nucleotide sequences present in cis or/and trans, necessary for transcription and/or translation of the gene comprising the structural gene of interest. The transcriptional regulatory elements normally comprise a promoter upstream of the gene sequence to be expressed, transcriptional initiation and termination sites, and a polyadenylation signal sequence. The term "transcriptional initiation site" refers to the nucleotide in the gene corresponding to the first nucleic acid to be incorporated into the primary transcript, i.e. the pre-mRNA; the transcriptional initiation site may overlap with the promoter sequence. The term "transcriptional termination site" refers to a nucleotide sequence normally present at the 3' end of a gene of interest to be transcribed, that causes RNA polymerase to terminate transcription. The polyadenylation signal sequence, or poly-A addition signal provides the signal for the cleavage at a specific site at the 3' end of a eukaryotic mRNA and the post-transcriptional addition of a sequence of about 100-200 adenine nucleotides (polyA tail) to the cleaved 3' end in the nucleus. The polyadenylation signal sequence may include the consensus sequence AATAAA located at about 10-30 nucleotides upstream from the site of cleavage.

Translational regulatory elements include a translational initiation (AUG) and stop codon (TAA, TAG or TGA). An internal ribosome entry site (IRES) can be included in some constructs.

A "promoter" refers to a polynucleotide sequence that controls transcription of a gene or nucleic acid sequence to which it is operably linked. A promoter includes signals for RNA polymerase binding and transcription initiation. The promoter used will be functional in the cell type of the host cell in which expression of the selected/operably linked sequence is contemplated. A large number of promoters including constitutive, inducible and repressible promoters from a variety of different sources, are well known in the art (and identified in databases such as GenBank) and are available as or within cloned polynucleotides (from, e.g., depositories such as ATCC as well as other commercial or individual sources). A "promoter" comprises a nucleotide sequence that directs the transcription of a structural gene. Typically, a promoter is located in the 5' non-coding or untranslated region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee, R. E. Jr., et al., Mol. Endocrinol. 7 (1993) 551-60), cyclic AMP response elements (CREs), serum response elements (SREs; Treisman, R., Seminars in Cancer Biol. 1 (1990) 47-58), glucocorticoid response elements (GREs), and binding sites for other transcription factors, such as CRE/ATF (O'Reilly, M. A., et al., J. Biol. Chem. 267 (1992) 19938-43), AP2 (Ye, J., et al., J. Biol. Chem. 269 (1994) 25728-34), SPI, cAMP response element binding protein (CREB; Loeken, M. R., Gene Expr. 3 (1993) 253-64) and octamer factors (see, in general, Watson et al., eds., Molecular Biology of the Gene, 4th ed., The Benjamin/Cummings Publishing Company, Inc. (1987), and Lemaigre, F. P. and Rousseau, G. G., Biochem. J. 303 (1994) 1-14). If a promoter is an inducible promoter, then the rate of transcription increases in response to an inducing agent. In contrast, the rate of transcription is not regulated by an inducing agent if the promoter is a constitutive promoter. Repressible promoters are also known. For example, the c-fos promoter is specifically activated upon binding of growth hormone to its receptor on the cell surface. Tetracycline (Tet) regulated expression can be achieved by artificial hybrid promoters that consist e.g. of a CMV promoter followed by two Tet-operator sites. The Tet-repressor binds to the two Tet-operator sites and blocks transcription. Upon addition of the inducer tetracycline, the Tet-repressor is released from the Tet-operator sites and transcription proceeds (Gossen, M. and Bujard, H. PNAS 89 (1992) 5547-5551). For other inducible promoters including metallothionein and heat shock promoters, see, e.g., Sambrook et al. (supra) and Gossen et al., Curr. Opin. Biotech. 5 (1994) 516-520. Among the eukaryotic promoters that have been identified as strong promoters for high-level expression are the SV40 early promoter, adenovirus major late promoter, mouse metallothionein-I promoter, Rous sarcoma virus long terminal repeat, Chinese hamster elongation factor 1 alpha (CHEF-1, see e.g. U.S. Pat. No. 5,888,809), human EF-1 alpha, ubiquitin, and human cytomegalovirus immediate early promoter (CMV IE).

The "promoter" can be constitutive or inducible. An enhancer (i.e. a cis- acting DNA element that acts on a promoter to increase transcription) may be necessary to function in conjunction with the promoter to increase the level of expression obtained with the promoter alone, and may be included as a transcriptional regulatory element. Often, the polynucleotide segment containing the promoter will include enhancer sequences as well (e.g. CMV or SV40).

"Operably linked" refers to a juxtaposition of two or more components, wherein the components so described are in a relationship permitting them to function in their intended manner. For example, a promoter and/or enhancer are operably linked to a coding sequence, if it acts in cis to control or modulate the transcription of the linked coding sequence. Generally, but not necessarily, the DNA sequences that are "operably linked" are contiguous and, where necessary to join two protein encoding regions such as a secretory leader and a polypeptide, or a polypeptide and a transmembrane domain, or a polypeptide and a signal peptide for a GPI-anchor, or a polypeptide and a translational stop codon, contiguous and in reading frame. However, although an operably linked promoter is generally located upstream of the coding sequence, it is not necessarily contiguous with it. Enhancers do not have to be contiguous. An enhancer is operably linked to a coding sequence if the enhancer increases transcription of the coding sequence. Operably linked enhancers can be located upstream, within or downstream of coding sequences and at considerable distance from the promoter. A polyadenylation site is operably linked to a coding sequence if it is located at the downstream end of the coding sequence such that transcription proceeds through the coding sequence into the polyadenylation sequence. Linking is accomplished by recombinant methods known in the art, e.g., using PCR methodology and/or by ligation at convenient restriction sites. If convenient restriction sites do not exist, then synthetic oligonucleotide adaptors or linkers are used in accord with conventional practice.

The term "production of pre-mRNA" as used herein denotes a process of transcription of DNA into its complementary pre-mRNA. Eukaryotic DNA is composed of coding and non-coding regions, which are referred to as exons (coding) and introns (non-coding). In the transcription process of DNA into its complementary pre-mRNA the genomic organization of exons and introns is maintained.

The term "processing of pre-mRNA" as used herein denotes a post-transcriptional modification process. In this step, the introns of the pre-mRNA are spliced out, i.e. removed from the pre-mRNA, the 5' end of the processed mRNA is capped and 3' polyadenylation is performed. The final nuclear, i.e. mature, mRNA is obtained in this step.

The term "transmembrane domain" as used within this application denotes a polypeptide or protein which is encoded on the DNA level by at least one exon and which comprises an extracellular, a transmembrane, and an intracellular region. A transmembrane domain generally comprises three distinct structural regions: an N-terminal extracellular region, a central conserved transmembrane stretch, and a C-terminal cytoplasmatic region. In one embodiment the transmembrane domain comprises in N- to C-terminal direction an extracellular region and a transmembrane region. The transmembrane domain may additionally comprise an intracellular or cytoplasmatic region.

The term "a fragment of a transmembrane domain" as used within this application denotes the part of a transmembrane domain that spans the cell membrane, i.e. which is located within the cell membrane, i.e. the transmembrane stretch.

The term "alternatively spliceable nucleic acid" denotes a nucleic acid beginning with a 5' splice donor site and terminated by a 3' splice acceptor site. This nucleic acid contains a translational stop codon and a polyadenylation signal. This alternatively spliceable nucleic acid comprises a non coding region which is not constitutively spliced out of the corresponding pre-mRNA, such as, for example, the intron after the exon encoding an immunoglobulin heavy chain $C_H3$ or $C_H4$ domain. The "alternative splicing event" taking place at the 5' splice donor site of the alternatively spliceable nucleic acid is a decision event whether the alternatively spliceable nucleic acid is spliced out of the pre-mRNA or if it is at least partially maintained and comprised in the mature (processed) mRNA.

The term "alternative splicing" and grammatical equivalents thereof as used herein refers to a process in eukaryotic cells in which from a single pre-mRNA due to different processing of one or more introns different mature mRNAs can be obtained and accordingly different isoforms of a polypeptide can be expressed. In one embodiment of the invention a single, i.e. only one, intron of the produced pre-mRNA can be spliced alternatively. In another embodiment the second nucleic acid can be spliced alternatively. In a further embodiment comprises the second nucleic acid an alternatively spliceable intron. The different processing is a "yes/no" decision, i.e. in the alternative splicing process the intron to be processed, i.e. the "alternatively spliceable nucleic acid", is either at least partially retained or spliced out. This has not to be understood as a branching point mechanism resulting in different exons to follow. It is in fact a mechanism in which an alternatively spliceable nucleic acid is either spliced out or at least partially maintained in the mature mRNA. With this mechanism the alternatively spliceable nucleic acid and, thus, the therein comprised in frame translational stop codon are either retained or removed.

Alternative splicing is an important regulatory mechanism in eukaryotic cells. With alternative splicing different combinations of exons in a mature mRNA can be obtained from the same pre-mRNA giving rise to a plurality of different proteins encoded by the same DNA.

The term "expression" as used herein refers to transcription and/or translation processes occurring within a cell. The level of transcription of a desired product in a cell can be determined on the basis of the amount of corresponding mRNA that is present in the cell. For example, mRNA transcribed from a selected sequence can be quantitated by PCR or by Northern hybridization (see Sambrook et al., Molecular Cloning: A Laboratory Manual, Cold Spring Harbor Laboratory Press (1989)). Polypeptides can be quantitated by various methods, e.g. by ELISA, by assaying for the biological activity of the polypeptide, or by employing assays that are independent of such activity, such as Western blotting, SDS polyacrylamide gel electrophoresis, NMR or radioimmunoassay, e.g. by using antibodies that recognize and bind to the polypeptide (see Sambrook et al., 1989, supra).

A "host cell" refers to a cell into which a heterologous nucleic acid encoding a polypeptide or protein is introduced. Host cell includes both prokaryotic cells, which are used for propagation of plasmids, and eukaryotic cells, which are used for the expression of the heterologous nucleic acid. Preferably, the eukaryotic cells are mammalian cells. Preferably the mammalian cells are CHO cells, BHK cells, NS0 cells, Sp2/0 cells, COS cells, HEK cells, PER.C6® cells.

A "polypeptide" is a polymer consisting of amino acids joined by peptide bonds, whether produced naturally or synthetically. Polypeptides of less than about 20 amino acid residues may be referred to as "peptides", whereas polypeptides consisting of more than 100 amino acid residues or consisting of two or more polypeptide chains may be referred to as "proteins".

A "protein" is a macromolecule comprising at least one polypeptide chain of a length of 100 amino acids or more or comprising two or more polypeptide chains.

Polypeptides and protein may also comprise non-peptidic components, such as carbohydrate groups, metal ions, lipids, carboxylic acid esters, or combinations thereof. The non-peptidic substituents may be added by the cell, in which the polypeptide or protein is produced, and may vary with the type of cell. Polypeptides and proteins are defined herein in terms of their amino acid backbone structures; additions such as carbohydrate groups are generally not specified, but may be present nonetheless.

"Heterologous DNA" or "heterologous nucleic acid" refers to a DNA molecule or a nucleic acid, or a population of DNA molecules or a population of nucleic acids, that do not exist naturally within a given host cell. DNA molecules heterologous to a particular host cell may contain DNA derived from the host cell species (i.e. endogenous DNA) so long as that host DNA is combined with non-host DNA (i.e. exogenous DNA). For example, a DNA molecule containing a non-host DNA segment encoding a polypeptide operably linked to a host DNA segment comprising a promoter is considered to be a heterologous DNA molecule. Conversely, heterologous DNA can comprise an endogenous structural gene operably linked with an exogenous promoter.

A peptide or polypeptide encoded by a non-host, i.e. heterologous, nucleic acid is a "heterologous" peptide or polypeptide.

The term "biologically active polypeptide" as used herein refers to an organic molecule, e.g. a biological macromolecule such as a peptide, protein, glycoprotein, nucleoprotein, mucoprotein, lipoprotein, synthetic polypeptide or protein, that causes a biological effect when administered in or to artificial biological systems, such as bioassays using cell lines and viruses, or in vivo to an animal, including but not limited to birds and mammals, including humans. This biological effect can be but is not limited to enzyme inhibition or activation, binding to a receptor or a ligand, either at the binding site or circumferential, signal triggering or signal modulation. In one embodiment said biologically active polypeptide is selected from the group of polypeptides comprising immunoglobulins, immunoglobulin fragments, immunoglobulin conjugates, and antifusogenic peptides.

Biologically active molecules are without limitation for example hormones; cytokines; interleukins; immunoglobulins; antifusogenic peptides; growth factors; receptor ligands, agonists or antagonists; cytotoxic agents; antiviral agents; imaging agents; enzyme inhibitors; enzyme activators or enzyme activity modulators such as allosteric substances, and conjugates of these.

The term "amino acid" as used within this application denotes a group of carboxy α-amino acids, which either directly or as precursor can be encoded by nucleic acids, comprising alanine (three letter code: Ala, one letter code: A), arginine (Arg, R), asparagine (Asn, N), aspartic acid (Asp, D), cysteine (Cys, C), glutamine (Gln, Q), glutamic acid (Glu, E), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V).

A "cloning vector" is a nucleic acid, such as a plasmid, cosmid, phagemid or bacterial artificial chromosome (BAC), which has the capability of replicating autonomously in a host cell. Cloning vectors typically contain one or a small number of restriction endonuclease recognition sites that allow insertion of a nucleic acid in a determinable fashion without loss of an essential biological function of the vector, as well as nucleotide sequences encoding a selectable marker, that is suitable for use in the identification and selection of cells transformed with the cloning vector. Selectable markers typically include genes that provide tetracycline, neomycin, G418, or ampicillin resistance.

An "expression vector" is a nucleic acid encoding a heterologous polypeptide or protein to be expressed in a host cell. Typically, an expression vector comprises a prokaryotic plasmid propagation unit, e.g. for *E. coli*, comprising a prokaryotic origin of replication and a prokaryotic selection marker, a eukaryotic selection marker, and one or more expression cassettes for the expression of a nucleic acid of interest, each comprising a promoter, a nucleic acid, and a transcription terminator including a polyadenylation signal. Gene expression is usually placed under the control of a promoter, and such a structural gene is said to be "operably linked" to the promoter. Similarly, a regulatory element and a core promoter are operably linked if the regulatory element modulates the activity of the core promoter.

A "polycistronic transcription unit" is a transcription unit in which more than one structural gene is under the control of the same promoter.

An "isolated polypeptide" or an "isolated protein" is a polypeptide or protein that is essentially free from contaminating cellular components, such as not covalently bound carbohydrate, lipid, or other proteinaceous impurities as well as non-proteinaceous impurities associated with the polypeptide or protein in nature. Typically, a preparation of isolated polypeptide/protein contains the polypeptide/protein in a highly purified form, i.e. at least about 80% pure, at least about 90% pure, at least about 95% pure, greater than 95% pure, or greater than 99% pure. One way to show that a particular preparation contains an isolated polypeptide or protein is by the appearance of a single band following sodium dodecyl sulfate (SDS)-polyacrylamide gel electrophoresis of the preparation and Coomassie Brilliant Blue staining of the gel. However, the term "isolated" does not exclude the presence of the same polypeptide or protein in alternative physical forms, such as dimers or alternatively glycosylated or derivatized forms.

As used herein, the term "immunoglobulin" denotes a protein consisting of one or more polypeptides substantially encoded by immunoglobulin genes. This definition includes variants such as mutated forms, i.e. forms with substitutions, deletions, and insertions of one or more amino acids, truncated forms, as well as fused forms. The recognized immunoglobulin genes include the different constant region genes as well as the myriad immunoglobulin variable region genes. Immunoglobulins may exist in a variety of formats, including, for example, Fv, Fab, and F(ab)2 as well as single chains (scFv) (e.g. Huston, J. S., et al., PNAS USA 85 (1988) 5879-5883; Bird, R. E., et al., Science 242 (1988) 423-426; and, in general, Hood et al., Immunology, Benjamin N. Y., 2nd edition (1984) and Hunkapiller, T., and Hood, L., Nature 323 (1986) 15-16).

Each of the heavy and light polypeptide chains of an immunoglobulin, if present at all, may comprise a constant region (generally the carboxyl terminal portion). The constant region of the heavy chain mediates the binding of the antibody i) to cells bearing a Fc receptor, such as phagocytic cells, or ii) to cells bearing the neonatal Fc receptor (FcRn) also known as Brambell receptor. It also mediates the binding to some factors including factors of the classical complement system such as component C1q. Furthermore a transmembrane domain may follow the C-terminal constant domain of an immunoglobulin heavy chain, i.e. the $C_H3$ or $C_H4$ domain. This transmembrane domain allows for the formation of plasma-membrane-bound immunoglobulins or immunoglobulin fragments or immunoglobulin-fusion polypeptides.

Each of the heavy and light polypeptide chains of an immunoglobulin, if present at all, may comprise a variable domain (generally the amino terminal portion). The variable domain of an immunoglobulin's light or heavy chain comprises different segments, i.e. four framework regions (FR) and three hypervariable regions (CDR).

The term "at least a fragment of" denotes a fraction of a complete nucleic acid or a complete polypeptide, i.e. at least 20%, at least 40%, at least 60%, or at least 80% of the complete nucleic acid, polypeptide, or domain. For example, "a nucleic acid encoding at least a fragment of an immunoglobulin $C_H3$ or $C_H4$ domain" denotes a fraction of the nucleic acid encoding the complete immunoglobulin $C_H3$ or $C_H4$ domain, i.e. at least 20%, at least 40%, at least 60%, or at least 80% of the nucleic acid encoding the complete immunoglobulin $C_H3$ or $C_H4$ domain. In one embodiment a fragment of an immunoglobulin heavy chain is a C-terminal fragment of an immunoglobulin heavy chain.

The term "an in frame translational stop codon" denotes a translational stop codon (TAA, TAG, or TGA) which is succeeding a coding region of a nucleic acid without a frameshift of the reading frame with respect to the preceding coding region of the nucleic acid, i.e. which terminates the coding region during translation. An in frame translational stop codon is operably linked to the preceding coding region of a nucleic acid.

The term "without an in frame translational stop codon" denotes the absence of a translational stop codon (TAA, TAG, or TGA) in the designated nucleic acid and/or the presence of a translational stop codon, which can be found within or at the end of a coding region of a nucleic acid, but that is due to one or two basepair shifts not recognized during the translation of the processed mRNA (i.e. out-of-frame, not operably linked) and thus does not terminate the coding region in the translation process.

"Transcription terminator" as denoted within this application is a DNA sequence of 50-750 base pairs in length which gives the RNA polymerase the signal for termination of the mRNA synthesis. Very efficient (strong) terminators at the 3' end of an expression cassette are advisable to prevent the RNA polymerase from reading through, particularly when using strong promoters. Inefficient transcription terminators can lead to the formation of an operon-like mRNA which can be the reason for an undesired, e.g. plasmid-coded, gene expression.

The terms "not constitutively removed during pre-mRNA processing" and "not constitutively spliced out of the (corresponding) pre-mRNA" as used within this application denote a splicing process that does not unexceptionally take place during pre-mRNA processing, i.e. the nucleic acid of a specific intron is only sometimes removed during pre-mRNA processing. As a result two different mature mRNAs are obtained, one with at least a part the intron and one without the intron.

The term "GPI-anchor" as used within this application denotes a posttranslational modification attached to a C-terminus of a polypeptide or protein. A "GPI-anchor" has a core structure comprising at least one ethanolamine phosphate residue, a trimannoside, a glucosamine residue, and an inositol phospholipid. Notwithstanding this core structure a GPI-anchor normally possesses a certain microheterogenieaty and therefore a protein having a GPI-anchor normally is a mixture of proteins with homologous GPI-anchors of the same core structure having different side chain modifications.

The term "signal peptide for a GPI-anchor" denotes a C-terminal amino acid sequence of a polypeptide or protein which consists of one amino acid to which the GPI-anchor will be attached, an optional spacer peptide, and a hydrophobic peptide. Almost all of this signal peptide, i.e. the optional spacer peptide and the hydrophobic peptide, is removed post-translationally by the enzyme GPI-transaminase and a bond between the amino group of the core ethanolamine phosphate of the GPI-anchor and the amino acid to which the GPI-anchor is attached is formed.

After transfection with a heterologous nucleic acid, cells expressing a heterologous polypeptide encoded by the heterologous nucleic acid have to be selected. For selection a marker is used. The marker indicates cells in a population that have been successfully transformed and facilitates the selection and isolation of these cells. Different markers can be used, such as, e.g., selectable markers, or detectable labels like Green Fluorescent Protein (GFP).

Selection of cells can be performed in a single step or in multiple steps. In a single/multiple step procedure the first selection can be performed based e.g. on a threshold level of a selectable marker, such as a detectable label. For example, for selection by flow cytometry (e.g. by FACS—Fluorescence Activated Cell Sorting) a fluorescence threshold level is set and cells with a fluorescence above this threshold level are selected. Alternatively cells within the top 1-15% (i.e. the 15% of the cells with the most intense detectable label), or top 1-10%, or top 1-5%, or top 5-10%, or top 5-6% of fluorescence intensity of the sample population can be collected. An alternative method for the selection of a cells is immunological binding, e.g. to magnetic beads coated with Protein A or specific immunoglobulins. The selected panel of cells may be taken as basic population for a further selection step, e.g. by single cell seeding, cultivation and ELISA analysis (Enzyme-linked Immunosorbent Assay), or by limited dilution cloning, or by expanding by cultivation under selective culture conditions in selection medium for several days and a further FACS selection, or by a further FACS selection with a higher threshold level, which can for example be based on the fluorescence intensities detected in a preceding FACS selection, or by an immunoprecipitation method (see e.g. also WO 2005/020924). Selecting a cell according to the invention can be performed by a method selected from the group of flow cytometry, ELISA, immunoprecipitation, immunoaffinity column chromatography, magnetic bead immunoaffinity sorting, microscopy-based isolation methods, or immunological binding. In one embodiment selecting a cell according to the invention can be performed by a method selected from the group of flow cytometry, ELISA, immunoprecipitation, immunoaffinity column chromatography, magnetic bead immunoaffinity sorting, microscopy-based isolation methods, or immunological binding, followed by a method selected from the group of single cell seeding and cultivation, limited dilution, or expanding by cultivation, followed by a method selected from the group of FACS, immunoprecipitation, immunoaffinity column chromatography, magnetic bead immunoaffinity sorting, microscopy-based isolation methods, or ELISA As the efficacy of transfection methods and vectors known in the art is very high and thus a plurality of transfected cells is obtained, marker are preferred that also allow for the correlation of the expression yield of a transfected cell with the detected "intensity" of the marker. Therefore it is functional to link the expression of the heterologous polypeptide of interest with the expression of the marker.

The current invention uses splicing methodology, i.e. alternative splicing, to express a heterologous polypeptide and a marker from the same nucleic acid, i.e. from the same expression cassette whereby e.g. no IRES is employed. The marker in the current invention is a plasma-membrane-bound form of the expressed heterologous polypeptide. In the current invention the selectable marker comprises as N-terminal part the heterologous polypeptide and as C-terminal part either at least a fragment of a transmembrane domain or a GPI-anchor. Thus, the produced heterologous polypeptide and the extracellular part of the selectable marker, i.e. the part of the selectable marker which is detected, are identical.

The current invention comprises a method for selecting a eukaryotic cell expressing a heterologous polypeptide, whereby the method comprises
 a) transfecting a eukaryotic cell with a nucleic acid comprising in 5' to 3' direction
  i) a first nucleic acid encoding a heterologous polypeptide without an in frame translational stop codon,
  ii) a second nucleic acid beginning with a splice donor site and terminated by a splice acceptor site comprising an in frame translational stop codon and a polyadenylation signal,
  iii) a third nucleic acid encoding
   iiia) at least a fragment of a transmembrane domain, or
   iiib) a signal peptide for a GPI-anchor,
 b) culturing of said transfected cell under conditions suitable for the production of pre-mRNA from said nucleic acid, processing of said pre-mRNA, and translation of said processed mRNA into a heterologous polypeptide, wherein said transfected cell produces soluble heterologous polypeptide and plasma-membrane-bound heterologous polypeptide by alternative splicing of said pre-mRNA, and
 c) selecting a cell with plasma-membrane-bound heterologous polypeptide to be said cell expressing a heterologous polypeptide.

During transcription of DNA a copy of the DNA is obtained, the so called pre-messenger RNA (pre-mRNA). This pre-mRNA has the same organization as the template DNA, i.e. it has a genomic intron-exon-organization. Only the exons contain the information of the amino acid sequence of the encoded polypeptide.

Thus, the introns have to be removed from the pre-mRNA prior to translation. This process is called RNA-splicing.

A "spliceable nucleic acid" is characterized by at least a 5' splice donor site, a 3' splice acceptor site, and a so called branch site, which is normally located 20-50 bases upstream of the acceptor site. This architecture effects the recognition and the excision of the nucleic acid from the 5' splice donor site to the 3' splice acceptor site from the pre-mRNA during RNA splicing. During the splicing step the mature mRNA from which a polypeptide or protein is translated is generated. In one embodiment of the present invention at least one nucleic acid, preferably the second nucleic acid, is a spliceable nucleic acid containing additional regulatory elements, such as an in frame stop codon and a polyadenylation signal.

But the splicing process is not exclusive. It is, e.g., possible that an intron is not removed during pre-mRNA processing from the pre-mRNA and is thus at least partially embedded into the mature mRNA. If an in frame stop codon is present in this "optionally" included intron the translation stops at this stop codon and a variant of the encoded polypeptide is produced.

The recognition and excision of an intron is often regulated by additional cis-acting elements in the pre-mRNA. Due to their function and position these elements are referred to as exonic splice enhancer (ESE), exonic splice silencer (ESS), intronic splice enhancer (ISE), or intronic splice silencer (ISS), respectively (Black, D. L., Annu Rev Biochem 72 (2003) 291-336).

The genomic DNA of most eukaryotic genes has an intron-exon-organization. For example, within the exon encoding the C-terminal domain of the secreted form of an immunoglobulin heavy chain (i.e. $C_H3$ or $C_H4$, respectively) is a 5' splice donor site.

If this splice donor site is not effective in the processing of the heavy chain pre-mRNA, the intron following this exon, which contains a stop codon and a polyadenylation signal, is at least partially retained in the mature mRNA. The mRNA is then translated into an immunoglobulin heavy chain that ends with a $C_H3$ or $C_H4$ domain and represents a soluble immunoglobulin. This is the major processing pathway for immunoglobulin heavy chain genes in immunoglobulin secreting cells.

If this splice donor site is effective in the processing of the immunoglobulin heavy chain pre-mRNA, the consecutive intron, and thus the stop codon is removed. Hence the translation does not stop after the C-terminal domain of an immunoglobulin heavy chain. Furthermore, translation is continued with the succeeding spliced to exons encoding a transmembrane domain. This minor processing pathway for immunoglobulin heavy chain genes results in a plasma-membrane-bound immunoglobulin form presented on the cell surface of an immunoglobulin producing cell.

This process is referred to as "alternative splicing" and the nucleic acid (i.e the intron) optionally removed in this process is referred to as "alternatively spliceable nucleic acid".

If a nucleic acid encoding a heterologous polypeptide or a protein is linked to a nucleic acid encoding at least a fragment of a transmembrane domain or to a nucleic acid encoding a signal peptide for a GPI-anchor by/via an alternatively spliceable nucleic acid, i.e. an alternatively spliceable nucleic acid is located in between these two nucleic acids, and whereby these three nucleic acids are operably linked, two variants of the heterologous polypeptide or protein are expressed: a soluble variant, i.e. a variant only comprising the polypeptide or protein, and a plasma-membrane-bound variant, i.e. a variant comprising both, the polypeptide or protein and the transmembrane domain or the GPI-anchor.

In one embodiment the transfected nucleic acid is comprised in an expression cassette. In one embodiment the first nucleic acid is without an in frame translational stop codon at its 3' terminus. In another embodiment the first, second and third nucleic acids are operably linked. In one embodiment the third nucleic acid encodes at least a fragment of a transmembrane domain. In another embodiment the fragment of a transmembrane domain is a transmembrane region. In one embodiment the third nucleic acid encodes a signal peptide for a GPI-anchor. In one embodiment of the invention the polypeptide encoded by the first nucleic acid is selected from the group comprising immunoglobulin heavy chains, immunoglobulin light chains, biologically active polypeptides, fragments thereof, and fusion polypeptides thereof. In one embodiment of the invention the polypeptide encoded by the first nucleic acid is selected from the group comprising immunoglobulin heavy chains, immunoglobulin light chains, fragments thereof, and fusions thereof. In one embodiment the third nucleic acid encodes at least a fragment of an immunoglobulin transmembrane domain.

In more detail, the current invention comprises a method for selecting a eukaryotic cell expressing an immunoglobulin heavy chain, whereby the method comprises
  a) transfecting a eukaryotic cell with a nucleic acid comprising in 5' to 3' direction
    i) a first nucleic acid encoding an immunoglobulin heavy chain without an in frame translational stop codon,
    ii) a second nucleic acid beginning with a splice donor site and terminated by a splice acceptor site comprising an in frame translational stop codon and a polyadenylation signal,
    iii) a third nucleic acid encoding
      iiia) at least a fragment of a transmembrane domain, or
      iiib) a signal peptide for a GPI-anchor,
  b) culturing of said transfected cell under conditions suitable for the production of pre-mRNA from said nucleic acid, processing of said pre-mRNA, and translation of said processed mRNA into an immunoglobulin heavy chain, wherein said transfected cell produces soluble immunoglobulin heavy chain and plasma-membrane-bound immunoglobulin heavy chain by alternative splicing of said pre-mRNA, and
  c) selecting a cell with plasma-membrane-bound immunoglobulin heavy chain to be said cell expressing an immunoglobulin heavy chain.

In one embodiment the current invention comprises a method for selecting a eukaryotic cell expressing an immunoglobulin, whereby the method comprises
  a) transfecting a eukaryotic cell with a nucleic acid comprising a first expression cassette for an immunoglobulin light chain and a second expression cassette comprising in 5' to 3' direction
    i) a first nucleic acid encoding an immunoglobulin heavy chain without an in frame translational stop codon,
    ii) a second nucleic acid beginning with a splice donor site and terminated by a splice acceptor site comprising an in frame translational stop codon and a polyadenylation signal,
    iii) a third nucleic acid encoding
      iiia) at least a fragment of a transmembrane domain, or
      iiib) a signal peptide for a GPI-anchor,
  b) culturing of said transfected cell under conditions suitable for the production of pre-mRNA from said nucleic acid, processing of said pre-mRNA, and translation of said processed mRNA into an immunoglobulin heavy chain, wherein said transfected cell produces soluble immunoglobulin and plasma-membrane-bound immunoglobulin by alternative splicing of said pre-mRNA, and
  c) selecting a cell with plasma-membrane-bound immunoglobulin to be said cell expressing an immunoglobulin.

In one embodiment comprises the current invention a method for selecting a eukaryotic cell expressing an immunoglobulin, whereby the method comprises
  a) transfecting a eukaryotic cell with two nucleic acids either simultaneously or sequentially whereby one nucleic acid comprises an expression cassette for an immunoglobulin light chain and the other nucleic acid comprises an expression cassette comprising in 5' to 3' direction
    i) a first nucleic acid encoding an immunoglobulin heavy chain without an in frame translational stop codon, ii) a second nucleic acid beginning with a splice donor site and terminated by a splice acceptor site comprising an in frame translational stop codon and a polyadenylation signal,
iii) a third nucleic acid encoding
iiia) at least a fragment of a transmembrane domain, or
iiib) a signal peptide for an GPI-anchor,
b) culturing of said transfected cell under conditions suitable for the production of pre-mRNA from said nucleic acid, processing of said pre-mRNA, and translation of said processed mRNA into an immunoglobulin heavy chain, wherein said transfected cell produces soluble immunoglobulin and plasma-membrane-bound immunoglobulin by alternative splicing of said pre-mRNA, and
c) selecting a cell with plasma-membrane-bound immunoglobulin to be said cell expressing an immunoglobulin.

In one embodiment the transmembrane domain encoded by the third nucleic acid is an immunoglobulin transmembrane domain. In one embodiment of the invention the second nucleic acid comprises only one 5' splice donor site and only one 3' splice acceptor site. In another embodiment of the current invention is the second nucleic acid a naturally occurring immunoglobulin heavy chain intron, which is following the exon encoding an immunoglobulin heavy chain $C_H3$ or $C_H4$ domain, wherein in said intron at least 50 consecutive nucleotides are deleted.

For example, for the recombinant expression of immunoglobulin heavy chains in eukaryotic cells a nucleic acid either with genomic intron-exon-organization or only containing the coding regions, i.e. cDNA, is employed. In both cases the nucleic acid ends with the stop codon after the exon encoding the C-terminal domain of the immunoglobulin heavy chain. The thereafter in the genomic organization succeeding introns and exons, comprising an alternatively spliceable nucleic acid and a transmembrane domain, are omitted. Therefore with such a nucleic acid only a soluble immunoglobulin heavy chain is obtained.

If for recombinant expression of immunoglobulins or fragments thereof the genomic organization of the immunoglobulin heavy chain gene is retained at least partially, i.e. if the intron after the exon encoding the C-terminal domain (i.e. the alternatively spliceable nucleic acid) and the succeeding exon(s) encoding a transmembrane domain are retained, alternative splicing is possible. In the alternative splicing event the 3' terminal codons and the stop codon of the CH3- or CH4-domain encoding exon, respectively, are removed as/with the intronic sequence and a different, mature mRNA is generated instead, in which the coding region, i.e. the reading frame, is elongated at its 3' end by the additionally maintained exon(s). This mRNA is translated into a C-terminally extended immunoglobulin heavy chain which contains an additional transmembrane domain, or a fragment thereof, encoded by the additional 3' exon(s). This elongated immunoglobulin heavy chain is incorporated during the assembly of immunoglobulins resulting in plasma-membrane-bound immunoglobulins. It has now surprisingly been found that with such a nucleic acid according to the invention transfected cells producing a heterologous polypeptide can be selected. This methodology is generally applicable and is not restricted to immunoglobulins. To practice this methodology the nucleic acid for recombinant expression of a heterologous polypeptide without an in frame stop codon has to be operably linked to and in frame with the alternatively spliceable nucleic acid derived from an immunoglobulin comprising an in frame translational stop codon and a polyadenylation site.

The succeeding third nucleic acid is variable as well and can be selected from any nucleic acid encoding a transmembrane domain or a fragment thereof as well as from any nucleic acid encoding a signal peptide for a GPI-anchor. These elements, i.e. the nucleic acid encoding the polypeptide, the alternatively spliceable nucleic acid, and the nucleic acid encoding the transmembrane domain or the signal peptide for a GPI-anchor, can be selected and combined from different genes as well as different organisms. The only prerequisite is that the three nucleic acids are combined in such a way that the translational stop codon in the alternatively spliceable nucleic acid is in frame with the reading frame of the nucleic acid encoding the polypeptide, i.e. it can be recognized by the ribosome and translation is terminated.

Generally speaking, with the alternative splicing optionally a fraction of the C-terminus of the soluble form of the heterologous polypeptide is/may be removed from the pre-mRNA as part of an intron. This fraction encompasses optionally the 3' terminal codons, the 3' untranslated region, the stop codon, and the polyadenylation signal of the secreted form. Therefore, the nucleic acid beginning with a 5' splice donor site and terminated by a 3' splice acceptor site that is removed optionally overlaps/may overlap with the C-terminus of the not alternatively processed variant.

Hence, by using a nucleic acid according to the invention with an at least partially retained genomic organization of an immunoglobulin heavy chain gene, two variants of a heterologous polypeptide can be obtained, a short, soluble variant and a long, plasma-membrane-bound variant.

In one embodiment wherein the first nucleic acid encodes an immunoglobulin heavy chain comprises the first nucleic acid all exons and all but one intron of the genomically organized immunoglobulin heavy chain gene. In one embodiment encodes the third nucleic acid either a fragment of a transmembrane domain or a signal peptide for a GPI-anchor, whereby the fragment of the transmembrane domain is encoded by a single exon. In another embodiment is the transmembrane domain an immunoglobulin transmembrane domain encoded by an M1-M2-exon-fusion, i.e. by a single exon without the genomically intervening intron. In one embodiment the immunoglobulin transmembrane domain is encoded by a cDNA.

By introducing a nucleic acid with an at least partially retained overall genomic organization of an immunoglobulin heavy chain gene into a host cell, a cell is obtained, that expresses on the one hand soluble heterologous polypeptide and on the other hand plasma-membrane-bound heterologous polypeptide. For example, to obtain the two immunoglobulin variants, i.e. to enable alternative splicing, it is not necessary to maintain the entire genomic organization of the immunoglobulin heavy chain gene, i.e. all introns and exons. It is only required to maintain the alternative splice site in a functionable from. A "functionable splice site" is a nucleic acid sequence comprising a 5' splice donor site and a 3' splice acceptor site, thereby allowing for the excision of the interjacent nucleic acid sequence from the pre-mRNA. The recognition and excision of an intron is often regulated by additional cis-acting elements on the pre-mRNA. Due to their function and position these elements are referred to as exonic splice enhancer (ESE), exonic splice silencer (ESS), intronic splice enhancer (ISE), or intronic splice silencer (ISS), respectively (Black, D. L., Annu Rev Biochem 72 (2003) 291-336, which is incorporated by reference herein).

For the selection of transfected cells expressing a heterologous polypeptide different methods can be used, such as, without limitation, spectroscopic methods, e.g. fluorescence, ELISA and variants thereof, by assaying for the biological activity, or by employing assays that are independent of such activity, such as Western blotting, SDS polyacrylamide gel electrophoresis, or radioimmunoassay, using antibodies that recognize and bind to the heterologous polypeptide. Since the plasma-membrane-bound heterologous polypeptide has the same amino acid sequence and secondary structure as the soluble heterologous polypeptide except for its C-terminus, it can be determined with, e.g., the same antibodies as the soluble variant.

The plasma-membrane-bound variant of a polypeptide is firmly connected to the cell expressing it. Therefore the plasma-membrane-bound variant can be used as a marker to isolate cells that have been successfully transfected with a nucleic acid for the expression of a heterologous polypeptide or protein, e.g. an immunoglobulin. In one embodiment the polypeptide is an immunoglobulin. In one embodiment the immunoglobulin is selected from the group of IgG, IgE, and IgA.

The molecular ratio of the soluble variant of the heterologous polypeptide to the plasma-membrane-bound variant of the heterologous polypeptide is of from more than 50:50 to less than 100:0, preferably of from more than 75:25 to less than 100:0. For example, if a eukaryotic cell is transfected with a nucleic acid according to the invention encoding an immunoglobulin, successfully transfected cells can be selected by the appearance of plasma-membrane-bound immunoglobulin.

A nucleic acid according to the invention is a nucleic acid containing in 5' to 3' direction a coding region for a heterologous polypeptide, an alternatively spliceable nucleic acid, and a coding region for a transmembrane domain or a fragment thereof or a coding region for a signal peptide for a GPI-anchor. In more detail, the current invention comprises a nucleic acid, comprising a) a first nucleic acid encoding a heterologous polypeptide without an in frame translational stop codon,
b) a second nucleic acid beginning with a 5' splice donor site and terminated by a 3' splice acceptor site comprising an in frame translational stop codon and a polyadenylation signal, and
c) a third nucleic acid encoding
  i) at least a fragment of a transmembrane domain, or
  ii) a signal peptide for a GPI-anchor.

In other embodiments i) the 5' splice site of the alternatively spliced intron is located 5' to the normal stop-codon of the nucleic acid encoding the heterologous polypeptide, ii) the second nucleic acid is an alternatively spliceable nucleic acid, and iii) the 5' splice site is used only sometimes and not constitutively, resulting in a molecular ratio of normally processed heterologous polypeptide, i.e. soluble polypeptide, to alternatively processed heterologous polypeptide, i.e. plasma-membrane-bound polypeptide, of from more than 50:50 to less than 100:0. In one embodiment the first nucleic acid and the second nucleic acid are operably linked, i.e. the translational stop codon of the second nucleic acid is in frame to the reading frame of the first nucleic acid encoding a polypeptide or a fragment thereof.

The nucleic acid that can be removed by alternative splicing follows the nucleic acid encoding at least a fragment of a polypeptide and precedes the nucleic acid encoding at least a fragment of a transmembrane domain or encoding a signal peptide for a GPI-anchor. In one embodiment the heterologous polypeptide is a fusion polypeptide comprising N-terminally a polypeptide of interest and C-terminally at least a fragment of an immunoglobulin heavy chain $C_H3$ or $C_H4$ domain or a variant thereof. In one embodiment the nucleic acid comprises a fourth nucleic acid between the first nucleic acid and the second nucleic acid and/or the second nucleic acid and the third nucleic acid. That is the fourth nucleic acid is located e.g. after the second nucleic acid (i.e. after the 3' splice acceptor site) and before the 5' end of the third nucleic acid.

With an alternatively spliceable nucleic acid located between the nucleic acid encoding a heterologous polypeptide, and the nucleic acid encoding a transmembrane domain or encoding a signal peptide for a GPI-anchor, two variants of the heterologous polypeptide can be expressed: a heterologous polypeptide without transmembrane domain or GPI-anchor and a heterologous polypeptide with transmembrane domain or GPI-anchor. The heterologous polypeptide can be selected from, without limitation, for example, hormones; cytokines; growth factors; receptor ligands, agonists or antagonists; cytotoxic agents; antiviral agents; imaging agents; enzyme inhibitors; enzyme activators or enzyme activity modulators such as allosteric substances; immunoglobulins; or fusions or fragments thereof. In one embodiment the polypeptide is an immunoglobulin, an immunoglobulin heavy chain polypeptide, or an immunoglobulin fusion.

The invention can be practiced with any polypeptide, any transmembrane domain and any signal peptide for a GPI-anchor as long as an alternatively spliceable nucleic acid is embedded thereby. In more detail the nucleic acid fragment beginning with the 5' splice donor site and terminated by the 3' splice acceptor site has to be chosen properly. The preceding polypeptide and the succeeding transmembrane domain or GPI-anchor can be chosen freely.

The present invention further comprises a nucleic acid comprising a) a first multiple cloning site,
b) a spliceable nucleic acid beginning with a 5' splice donor site and terminated by a 3' splice acceptor site, wherein
  i) the spliceable nucleic acid comprises a stop codon and a polyadenylation signal, and
  ii) the spliceable nucleic acid is not constitutively removed during pre-mRNA processing,
c) a second multiple cloning site.

The present invention can be practiced, for example, without limitation, with the second nucleic acid, i.e. the alternatively spliceable nucleic acid, derived from the group of nucleic acids encoding the C3b/C4b receptor (complement receptor type 1) (Hourcade, D., et al., J. Exp. Med. 168 (1988) 1255-1270), human, chicken, and rat EGFR (Callaghan, T., et al., Oncogene 8 (1993) 2939-2948; Reiter, J. L., and Maihle, N. J., Nuc. Acids Res. 24 (1996) 4050-4056; Petch, L., et al., Mol. Cell Biol. 10 (1990) 2973-2982), immunoglobulin (Ig) α, ε, γ, μ heavy chain (Zhang, K., et al., J. Exp. Med. 176 (1992) 233-243; Rogers, J. E., et al., Cell 20 (1980) 303-312; Milcarek, C., and Hall, B., Mol. Cell Biol. 5 (1985) 2514-2520; Kobrin, B. J., et al., Mol. Cell Biol. 6 (1986) 1687-1697; Cushley, W., et al., Nature 298 (1982) 77; Alt, F. W., et al., Cell 20 (1980) 293-301; Peterson, M. L., Gene Exp. 2 (1992) 319-327), human $PLA_2$ receptor (Ancian, P., et al., J. Biol. Chem. 270 (1995) 8963-8970), chicken Cek5 (Connor, R. J., and Pasquale, E. B., Oncogene 11 (1995) 2429-2438), human FGFR (Johnson, D. E., et al., Mol. Cell Biol. 11 (1991) 4627-4634.

In one embodiment the second nucleic acid is an intron of an immunoglobulin located between the exon encoding the $C_H3/C_H4$ domain and the exon encoding at least a fragment of the transmembrane domain. In one embodiment the second nucleic acid is derived from the group of nucleic acids encoding human (hu) immunoglobulin (Ig) α (alpha) heavy chain, hu Ig δ (delta) heavy chain, hu Ig ε (epsilon) heavy chain, hu Ig γ1, γ2, γ3, and γ4 (gamma) heavy chain, hu Ig μ (miu) heavy chain, murine Ig heavy chain type α (alpha), murine Ig heavy chain type δ (delta), murine Ig heavy chain type ε (epsilon), murine Ig heavy chain type γ1 (gammal), murine Ig heavy chain type γ2A (gamma2A), murine Ig heavy chain type γ2B (gamma2B), murine Ig heavy chain type γ3 (gamma3), and murine Ig heavy chain type μ (miu).

In one embodiment the second nucleic acid is selected from the group of nucleic acids encoding human immunoglobulin γ1 heavy chain, human immunoglobulin γ2 heavy chain, human immunoglobulin γ3 heavy chain, human immunoglobulin γ4 heavy chain, human immunoglobulin ε heavy chain (1), and human immunoglobulin ε heavy chain (2). In one embodiment the second nucleic acid is derived/selected from the group of nucleic acids encoding human immunoglobulin δ heavy chain, human immunoglobulin γ1 heavy chain, human immunoglobulin γ2 heavy chain, human immunoglobulin p heavy chain, murine heavy chain type α, murine heavy chain type γ1, murine heavy chain type γ2B, murine heavy chain type γ3, and murine heavy chain type μ.

The present invention can be practiced, for example, without limitation, with the third nucleic acid, in case of the nucleic acid encoding at least a fragment of a transmembrane domain, selected from the group of nucleic acids encoding the C3b/C4b receptor (complement receptor type 1) (Hourcade, D., et al., J. Exp. Med. 168 (1988) 1255-1270), human, chicken, and rat EGFR (Callaghan, T., et al., Oncogene 8 (1993) 2939-2948; Reiter, J. L., and Maihle, N. J., Nuc. Acids Res. 24 (1996) 4050-4056; Petch, L., et al., Mol. Cell Biol. 10 (1990) 2973-2982), Ig α, ε, γ, μ heavy chain (Zhang, K., et al., J. Exp. Med. 176 (1992) 233-243; Rogers, J. E., et al., Cell 20 (1980) 303-312; Milcarek, C., and Hall, B., Mol. Cell Biol. 5 (1985) 2514-2520; Kobrin, B. J., et al., Mol. Cell Biol. 6 (1986) 1687-1697; Cushley, W., et al., Nature 298 (1982) 77; Alt, F. W., et al., Cell 20 (1980) 293-301; Peterson, M. L., Gene Exp. 2 (1992) 319-327), human $PLA_2$ receptor (Ancian, P., et al., J. Biol. Chem. 270 (1995) 8963-8970), chicken Cek5 (Connor, R. J., and Pasquale, E. B., Oncogene 11 (1995) 2429-2438), human FGFR (Johnson, D. E., et al., Mol. Cell Biol. 11 (1991) 4627-4634. In one embodiment the third nucleic acid is selected from the group of nucleic acids encoding human (hu) immunoglobulin (Ig) α (alpha) heavy chain, hu Ig δ (delta) heavy chain, hu Ig ε (epsilon) heavy chain, hu Ig γ1, γ2, γ3, and γ4 (gamma) heavy chain, hu Ig μ (miu) heavy chain, murine Ig heavy chain type α (alpha), murine Ig heavy chain type δ (delta), murine Ig heavy chain type ε (epsilon), murine Ig heavy chain type γ1 (gammal), murine Ig heavy chain type γ2A (gamma2A), murine Ig heavy chain type γ2B (gamma2B), murine Ig heavy chain type γ3 (gamma3), and murine Ig heavy chain type μ (miu). In one embodiment the third nucleic acid is selected from the group of nucleic acids encoding human immunoglobulin γ1 heavy chain, human immunoglobulin γ2 heavy chain, human immunoglobulin γ3 heavy chain, human immunoglobulin γ4 heavy chain, human immunoglobulin ε heavy chain (1), and human immunoglobulin ε heavy chain (2). In one embodiment the third nucleic acid is selected from the group of nucleic acids encoding human immunoglobulin δ heavy chain, human immunoglobulin γ1 heavy chain, human immunoglobulin γ2 heavy chain, human immunoglobulin μ heavy chain, murine heavy chain type α, murine heavy chain type γ1, murine heavy chain type γ2B, murine heavy chain type γ3, and murine heavy chain type μ.

In addition to the group of nucleic acids encoding at least a fragment of a transmembrane domain, can the third nucleic acid be selected from the group of nucleic acids encoding a signal peptide for a GPI-anchor. The group of nucleic acids encoding a signal peptide for a GPI-anchor comprises the group of nucleic acids encoding a signal peptide for a GPI-anchor derived from human alkaline diesterase, acetylcholine esterase, alkaline phosphatase (intestinal, liver, and placenta), CAMPATH-1 antigen, carcinoembryonic antigen, CD55, CD59, CD90, contactin-1, E48 antigen, folate receptor A and B, GPI-anchored protein p137, lymphocyte function-associated antigen-3, mDIA interacting protein, 5'-nucleotidase, urokinase plasminogen activator factor; from murine LY-6C antigen, LY-6 antigen, 5'-nucleotidase, OX45 antigen, stem cell antigen-2, vascular cell adhesion molecule-1, Qa lymphocyte antigen 2 (Qa2); from rabbit trehalase; from rat brevican protein, CD90, glypican protein, heparin sulfate proteoglycan, MRC OX-45 antigen, 5'-nucleotidase, pancreatic secretory granule membrane major glycoprotein, T-cell surface protein RT6.2; from yeast DNA repair protein PHR1, glycophospholipid-anchored surface protein 1; from porcine amyloid precursor protein, dipeptidase; from *Trypanosoma brucei* diverse variant surface proteins, polycyclic acidic repetitive protein; from *Trypanosoma congolense* variant surface protein YNat 1.1; from chicken melanotransferrin, neutral cell adhesion molecule; from *Torpedo marmorata* acetylcholine esterase; from hamster prion protein; from bovine 5'-nucleotidase; from slime mold membrane protein Gp64, pre-spore specific antigen; and from squid Sgp1, Sgp2.

In Table 1 examples of the nucleic acid sequences of the second nucleic acid, according to the invention are given. In Table 2 examples of nucleic acid sequences of the third nucleic acid according to the invention and of amino acid sequences corresponding to third nucleic acid sequences according to the invention are given. In Table 3 examples of nucleic acid sequences of the optional fourth nucleic acid and of amino acid sequences corresponding to fourth optional nucleic acids according to the invention are listed.

Table 1 lists the 5' splice donor site, the second (alternatively spliceable) nucleic acid, and the 3' splice acceptor site. As the sequence of the second nucleic acid generally exceeds 1 kb the listed sequences in Table 1 are shortened and show approximately the first and last 100 nucleotides of the second nucleic acid separated by a number referring to the total size of the complete second nucleic acid. The complete sequence of the second nucleic acid is contained in the given SEQ ID NO of the sequence listing. The stop codon is underlined.

The splice donor site is given in a format comprising the preceding consensus sequence of the splice donor site and the first six nucleotides of the second nucleic acid separated by a vertical line (see also e.g. Zhang, M. Q., Human Mol. Gen. 7 (1998) 919-932). Likewise is the splice acceptor site given by listing the last 6 nucleotides of the second nucleic acid and the succeeding splice acceptor site consensus sequence which are separated by a vertical line. The nucleotides directly after (5' splice donor site) and directly before (3' splice acceptor site) the vertical line are the first and last nucleotides of the second (spliceable) nucleic acid. The stop codon in the second nucleic acid is underlined in Table 1.

The second nucleic acid can either be directly linked to the nucleic acid encoding the heterologous polypeptide, i.e. the first nucleic acid, or with an optional small (9 to 21 bases) intervening nucleic acid sequence. In one embodiment the optional intervening (fifth) nucleic acid is derived from the nucleic acid preceding the second nucleic acid in the genome from which said second nucleic acid is obtained.

In Table 2 examples of third nucleic acid sequences encoding fragments of transmembrane domains and amino acid sequences of signal peptides for GPI-anchors are listed. This sequence can follow either directly or with an optional intervening sequence, i.e. a fourth nucleic acid, the 3' splice acceptor site. In Table 3 examples of fourth nucleic acid sequences and of amino acid sequences corresponding to fourth nucleic acids are listed.

In one embodiment the nucleic acid according to the invention comprises a fourth nucleic acid between said second nucleic acid and said third nucleic acid. In one embodiment the nucleic acid according to the invention comprises a fifth nucleic acid between said first nucleic acid and said second nucleic acid. One embodiment of the current invention is that said third nucleic acid is obtained from i) the same, or ii) a different gene or organism as said second nucleic acid, i.e. said third nucleic acid is not necessarily organized with said second nucleic acid in a genome.

The sequences are derived from publicly available genomes or databases (e.g. human genome project, mouse genome database, SwissProt. Where no annotation was accessible, the sequences have been predicted or completed by the software ALOM (see e.g. Klein, P., et al, Biochim. Biophys. Acta 787 (1984) 221-226). In case of complete of transmembrane domains the sequence in brackets is predicted by ALOM in addition to the given SwissProt sequence.

In one embedment the second nucleic acid is selected from the group of nucleic acids comprising SEQ ID NO: 001, 002, 003, 004, 005, 006, 007, 008, 009, 151, 152, 153, 154, 155, 156, 157, 158, 159, 169, 170, 171, 172,173. In one embodiment the second nucleic acid of the nucleic acid according to the invention is selected from the group of nucleic acid sequences of SEQ ID NO: 001 to SEQ ID NO: 009. In one embodiment the second nucleic acid is selected from the group of nucleic acids comprising SEQ ID NO: 002, 003, 156, 157, 170, and 171. In one embodiment the third nucleic acid of the nucleic acid according to the invention is selected from or is a fragment of a nucleic acid selected from the group of nucleic acid sequences of SEQ ID NO: 010 to SEQ ID NO: 018 and of nucleic acid sequences encoding the amino acid sequences of SEQ ID NO: 019 to SEQ ID NO: 069. In one embodiment the third nucleic acid of the nucleic acid according to the invention is selected from or is a fragment of a nucleic acid selected from the group of nucleic acid sequences of SEQ ID NO: 010, 011, 012, 013, 014, 015, 016, 017, 018, 160, 161, 163, 164, 165, 166, 167, 168, 174, 175, 176, and of nucleic acid sequences encoding the amino acid sequences of SEQ ID NO: 019 to SEQ ID NO: 069 and 162. In one embodiment the third nucleic acid of the nucleic acid according to the invention is selected from or is a fragment of a nucleic acid selected from the group of nucleic acid sequences of SEQ ID NO: 011, 012, 165, 166, 175 and of nucleic acid sequences encoding the amino acid sequences of SEQ ID NO: 019 to SEQ ID NO: 036. In another embodiment the third nucleic acid of the nucleic acid according to the invention is selected from or is a fragment of a nucleic acid selected from the group of nucleic acid sequences of SEQ ID NO: 011, 012, 165, 166, and 175. In one embodiment the fourth nucleic acid of the nucleic acid according to the invention is selected from or comprises a nucleic acid selected from the group of nucleic acid sequences of SEQ ID NO: 070 to SEQ ID NO: 078 and of nucleic acid sequences encoding the amino acid sequences of SEQ ID NO: 079 to SEQ ID NO: 129.

TABLE 1

Examples of second nucleic acids.

| protein | 5' splice donor site | second nucleic acid (spliceable nucleic acid) | 3' splice acceptor site |
|---|---|---|---|
| human immunoglobulin δ heavy chain | GCT\|GTGAGT | GTGAGTCACCCCCAGGCCCAGGGTTGGGACGGGGACTCTGAGGGGGGCCATAAG GAGCTGGAATCCATACTAGGCAGGGGTGGGCACTGGGCAGGGGCGGG . . . (2.77 kb total) . . . GACTCGCCGTCATTTCAGCTCCACGCTGTGCGGGGGTGGGTGGAGGGGTAGCCT GGCCCTCATGACCAGGGAGCTTCTCACTCAGCCCCTGTTCCTCCCCAG (SEQ ID NO: 001) | CCCCAG\|A |
| human immunoglobulin γ1 heavy chain | CGG\|GTAAAT | GTAAATGAGTGCCACGGCCGGCAAGCCCCCGCTCCCCAGGCTCTCGGGGTCGCG CGAGGATGCTTGGCACGTACCCCGTGTACATACTTCCCAGGCACCC . . . (1.3 kb total) . . . CCCGGCCGGGCCCTACATCCTGGGTCCTGCCACAGAGGGAATCACCCCCAGAGG CCCAAGCCCAGGGGACACAGCACTGACCACCCCCTTCCTGTCCAG (SEQ ID NO: 002) | GTCCAG\|A |
| human immunoglobulin γ2 heavy chain | CGG\|GTAAAT | GTAAATGAGTGCCACGGCCGGCAAGCCCCCGCTCCCCAGGCTCTCGGGGTCGCG CGAGGATGCTTGGCACGTACCCCGTCTACATACTTCCCGGGCACCC . . . (1.3 kb total) . . . CCCGGCCGGGCCCTACATCCTGGGTCCTGCCACAGAGGGAATCACCCCCAGAGG CCCGAGCCCAGCAGGACACAGTATTGACCACCCACTTCCTGTCCAG (SEQ ID NO: 003) | GTCCAG\|A |
| human immunoglobulin μ heavy chain | CCG\|GTAAAC | GTAAACCCACCCTGTACAACGTGTCCCTGGTCATGTCCGACACAGCTGGCACCTG CTACTGACCCTGCTGGCCTGCCCACAGGCTCGGGGCGGCTGGCC . . . (1.9 kb total) . . . GCCTAGGGGCCAAGGGTGGGCCTAGAGGATGGGCCCCGGGGGGCTTTGCTGG GTGCCACCCCAGCCTGACCCTATTCCCCCGTGCTGTGTCTCCTGCAG (SEQ ID NO: 004) | CTGCAG\|A |
| murine Ig heavy chain type α | CGG\|GTAAAC | GTAAACCCACCAATGTCAGCGTGTCTGTGATCATGTCAGAGGGAGATGGCATCTG CTACTGAGCCACCCTGCCTGTCCCTACTCCTGAAATAAACTCTGT . . . (2.43 kb total) . . . CCACTGTCCCCAAAGCCCAAGGAGGCATAGAAGCAGAAACCTTAAGTCTGAGCCC CCATCCCCATGGGTTTGGATCTAGAAGGTCATCTATGTCTTACAG (SEQ ID NO: 005) | TTACAG\|A |

TABLE 1-continued

Examples of second nucleic acids.

| protein | 5' splice donor site | second nucleic acid (spliceable nucleic acid) | 3' splice acceptor site |
|---|---|---|---|
| murine Ig heavy chain type ε (2) | TTG\|GTAACA | GTAACACCTCCCTCCATCCCTCC<u>TAG</u>GCCTCCATGTAGCTGTGGTGGGGAAGGTG<br>GATGACAGACATCCGCTCACTGTTGTAACACCAGGAAGCTACCCCAATAAACACT<br>CAGTGCCTGATTAGAGCCCTGGGT<br>. . . (1.7 kb total) . . .<br>ACTGGCTGGTCCCACCCCATCCCAGAGCTAGACCTCCAGGACCTATGTATTGAAG<br>(SEQ ID NO: 173) | TTGAAG\|A |
| murine Ig heavy chain type γ 1 | CTG\|GTAAAT | GTAAA<u>TGA</u>TCCCAGTGTCCTTGGAGCCCTCTGGTCCTACAGGACTCTGACACCTAC<br>CTCCACCCCTCCCTGTGTAAATAAAGCACCCAGCACTGCCTTGG<br>. . . (1.4 kb total) . . .<br>CTGCAGCTTTCTCCTGGGCCTCCATACAGCCTCCTGCCACACAGGGAATGGCCCTA<br>GCCCCACCTTATTGGGACAAACACTGACCGCCCTCTCTGTCCAG<br>(SEQ ID NO: 006) | GTCCAG\|G |
| murine Ig heavy chain type γ2B | CGG\|GTAAAT | GTAAA<u>TGA</u>GCTCAGCACCCACAAAGCTCTCAGGTCCTAAGAGACACTGGCACCCAT<br>ATCCATGCATCCCTTGTATAAATAAAGCATCCAGCAAAGCCTGG<br>. . . (1.36 kb total) . . .<br>AGATCTCTCCTCTGACTTCATGCAGACATGTCTGCCTCACAGGGAATCTCTCCCAG<br>CATCAACCATGTTGGGACAAACACTGACTGTCCTCTCTGTTCAG<br>(SEQ ID NO: 007) | GTTCAG\|G |
| murine Ig heavy chain type γ3 | CTG\|GTAAAT | GTAAA<u>TGA</u>GAACAGCACCTAGCCATTCCTCGGGTCTTACAAGACACTGATACCAGC<br>CCTAACCGGTGAACCCTATAAATAAAGCACCCAGAGATGGGACC<br>. . . (total 1.47 kb) . . .<br>CTGCAGCTTTCTCCTGGGCCTCCATGCAGCCTCCTGCCACACAGGGAATGGCCCT<br>AGCTCTACCTTGTTGGGACAAACACTGACTTTCCTCTCTGTTCAG<br>(SEQ ID NO: 008) | GTTCAG\|A |
| murine Ig heavy chain type μ | CTG\|GTAAAC | GTAAACCCACACTGTACAATGTCTCCCTGATCATGTCTGACACAGGCGGCACCTGC<br>TATTGACCATGCTAGCGCTCAACCAGGCAGGCCCTGGGTGTCCA<br>. . . (total 1.86 kb) . . .<br>GTCAATACTCGCTAAGATTCTCCAGAACCATCAGGGCACCCCAACCCTTATGCAAA<br>TGCTCAGTCACCCCAAGACTTGGCTTGACCCTCCCTCTCTGTGTCCCTTCATAG<br>(SEQ ID NO: 009) | TCATAG\|A |
| human fibroblast growth factor receptor 1 | AAG\|GTACAC | GTACACACTGTAACTTCTCCTCTCGATGTCCTGCCCTCGCCACGGGCAC.GGGGGG<br>AGCATGCATTTCCAGGCTTGGGGAGACACAGAGGCAGGAGAGCTGGAAGAATGGG<br>CTCCTGCCTGCCTGGTGCCACATCCTGCCCCAGCTTTGAGGGCTGAATCCTCTCAG<br>CTCAGA<br>. . . (2 kb total) . . .<br>CATGGACGGGGCCCTCCAAGCCTGCTAACACCCTGTTCGCACTGACTCAG<br>SEQ ID NO: 151) | ACTCAG\|C |
| murine epithelial growth factor receptor | TGG\|GTACGT | GTACG TTCAATGGCAGTGGATCTTAAAGACCTTTTGGATC<u>TAA</u>GA CCAGAAGCCA<br>TCTCTGACTCCCCTCTCACC<br>. . . (2.7 kb total) . . .<br>GTATGGAATG CCCATATTAC CTTCTCTTGTCTCTCATTCCAG<br>(SEQ ID NO: 152) | TTCCAG\|G |
| human complement receptor 1 (C3b/C4b) | AGG\|GTGAGT | GGG<u>TGA</u>GTTGGCAGCAACATCTCTTGGTTTAAGAGTTCCAGCACAGCGATAGTACT<br>TTC<u>TAG</u>CCACATCTCAGCAAGGAAACTAGGCTATTGCCACCTGCTCTTAAGAGGCT<br>TGAACACA<br>. . . (5.7 kb total) . . .<br>TAGACTTCTCCTGCATTGTAATCCCTCTGGTTTGCCACATATGCATGCTGTCAGGA<br>AGTTGATGAGGTATGTACAGCACAATTTATTTTCCATTTTTTGCCTTTAG<br>(SEQIDNO: 153) | CTTTAG\|G |
| murine interleukin 4 receptor | ACC\|GTGAGT | GTGAGTATCAGGGTCGTAGGCTG<u>TGA</u>GGATCTCTACAGCCG<br>. . . (1.3 kb total) . . .<br>GGGCGGCCTCCCCATTCATGACTGTTTTTCTCCTTGCAG<br>(SEQIDNO: 154) | TTGCAG\|A |
| human immunoglobulin α heavy chain | CGG\|GTAAAC | GTAAACCCACCCATGTCAATGTGTCTGTTGTCATGGCGGAGGTGGACGGCACCTG<br>CTACTGAGCCGCCCGCCTGTCCCCACCCCTGAATAAACTCCATGCTCCCCAAGCA<br>GCCCCACGCTT<br>. . . (2.6 kb total) . . .<br>CCCAAGGAAGCATAGCCGCTGTTCACACGAGTCTGGGCCTGGCAG<br>(SEQ ID NO: 155) | TGGCAG\|G |
| human immunoglobulin ε heavy chain (1) | CCG\|GTAAAT | GTAAA<u>TGA</u>CGTACTCCTGCCTCCCTCCCTCCCAGGGCTCCATCCAGCTGTG<br>. . . (1.9 kb total)<br>CGTTGACTGACTCGGGACCTGGGTGCCCACCCTCAG<br>(SEQIDNO: 156) | CCTCAG\|G |

TABLE 1-continued

Examples of second nucleic acids.

| protein | 5' splice donor site | second nucleic acid (spliceable nucleic acid) | 3' splice acceptor site |
|---|---|---|---|
| murine immunoglobulin δ heavy chain | GTG\|<br>GTAAGT | GTAAGTCACAACTGGGTAAGAGTGTCAAGCAAGGACAGCACTTGGTACCTATGATA<br>GACAAATACTCCTGTTTGGGAAGAGGAGGTCTGCATTGTCTAGATAAGAGGAACAC<br>TGTGCTTATCTGTTTCAGTTTAAAAGACAGAACTACA<u>TAA</u>CACTTCACCCTTTCTAC<br>AACACTTAGATTTTTCAGCCCTCTCCTCTA<br>. . . (6.35 kb total) . . .<br>TTCTGTAGGGTGGAGACCTTCTCATGAGCACTAGTTCTTCCCTAG<br>(SEQ ID NO: 172) | CCCTAG\|G |
| human immunoglobulin ε heavy chain (2) | CCG\|<br>GTAAAT | GTAAA<u>TGA</u>CGT ACTCCTGCCT CCCTCCCTCC CAGGGCTCCA TCCAGCTGTG<br>. . . (2.1 kb total) . . .<br>GCCACTGTGG AGCCGGGAGG GCTGACTGGC CAGGTCCCCC AG<br>(SEQ ID NO: 170) | CCCCAG\|A |
| human immunoglobulin γ3 heavy chain | CGG\|<br>GTAAAT | GTAAA<u>TGA</u>GTGCGACGGCCGGCAAGCCCCCGCTCCCCGGGCTCTC<br>. . . (1.3 kb total) . . .<br>CCCCAGAGGCCCGAGCCCAGCAGGACACAGCACTGACCACCCTCTTCCTGTCCAG<br>(SEQ ID NO: 157) | GTCCAG\|A |
| human immunoglobulin γ4 heavy chain | TGG\|<br>GTAAAT | GTAAA<u>TGA</u>GTGCCAGGGCCGGCAAGCCCCCGCTCCCCGGGCTCTCGGGGTCGCGC<br>GAGGATGCTTGGCACGTACCCCGTGTACATACTTC<br>. . . (1.3 kb total) . . .<br>CCCCAGAGGCCCAAGCCCAGGGGGACACAGCACTGACCACCCCCTTCCTGTCCAG<br>(SEQ ID NO: 171) | GTCCAG\|A |
| murine Ig heavy chain type ε (1) | TTG\|<br>GTAACA | GTAACACCTCCCTCCATCCCTCC<u>TAGG</u>CCTCCATGTAGCTGTGGTGGGGAAGGTG<br>GATGACAGACATCCGCTCACTGTTGTAACACCAGGAAGCTACCCCAATAAACACTC<br>AGTGCCTGATTAGAGCCCTGGGT<br>. . . (1.5 kb total) . . .<br>CCACTCTAGCTTCATCAGAACTGCATGAGACAAGTATGGGGTCTACCCCCTCCCCA<br>CTGTCACCTGGAGTCTGGGGAAGCTAACTGGCTGGTCCCACCCCATCCCAGAGCT<br>AGACCTCCAGGACCTATGTATTGAAG<br>(SEQ ID NO: 158) | TTGAAG\|A |
| murine Ig heavy chain type γ2A | TGG\|<br>GTAAAT | GTAAA<u>TGA</u>GCTCAGCACACACAATGCTCCTGGGTCCTAATGGACACTGGCACCCAT<br>ATCCATGCATCCCTTGTATAAATAAAGCACCCAGCAAAGCCTGGGACCATGTAAAA<br>CTGT<br>. . . (1.35 kb total) . . .<br>GAAGGCTCCAGGAAGGGTCTGCTGTACCAGTCAGGCTGGAGCTCTCTCCTCTACT<br>TCATGCAAACATGTCTGCATCACAGGGAATCTCTCCCAGCACCAACCATGTTGGGA<br>CAAACACTGACTGTCCTCTCTGTTCAG<br>(SEQ ID NO: 159) | GTTCAG\|G |
| Human interleukin 4 receptor | ACT\|<br>GTGAGT | GTGAGTATCAAGAGGCC<u>TAAG</u>CAATGGTAATCTCCACTCTCCATTCTTCCCCTG<br>. . . (3.1 kb total) . . .<br>GGAGCCCAGGCTGTACCATGGCTGACCTCAGCTCATGGCTTCCCCTCCCACTTCCAG<br>(SEQ ID NO: 169) | TTCCAG\|C |

TABLE 2

Examples of third nucleic acids and amino acids corresponding to third nucleic acids.

| source | nucleotide or amino acid sequence | SEQ ID NO: |
|---|---|---|
| human immunoglobulin δ heavy chain/transmembrane strech | AGCCTGTGGACCACCCTGTCCACGTTTGT<br>GGCCCTCTTCATCCTCACCCTCCTCTACAG<br>CGGCATTGTCACTTTCATCAAGGTGAAG | 010 |
| human immunoglobulin γ1 heavy chain/transmembrane strech | GGGCTGTGGACGACCATCACCATCTTCAT<br>CACACTCTTCCTGTTAAGCGTGTGCTACAG<br>TGCCACCGTCACCTTCTTC | 011 |
| human immunoglobulin γ2 heavy chain/transmembrane strech | GGGCTGTGGACCACCATCACCATCTTCAT<br>CACACTCTTCCTGCTAAGCGTGTGCTACA<br>GTGCCACCATCACCTTCTTC | 012 |
| human immunoglobulin μ heavy chain/transmembrane strech | AACCTGTGGGCCACCGCCTCCACCTTCAT<br>CGTCCTCTTCCTCCTGAGCCTCTTCTACAG<br>TACCACCGTCACCTTGTTCAAG | 013 |

TABLE 2-continued

Examples of third nucleic acids and amino acids corresponding to third nucleic acids.

| source | nucleotide or amino acid sequence | SEQ ID NO: |
|---|---|---|
| murine Ig heavy chain type α/ transmembrane strech | ACTGTGACCTTCCTCACCCTCTTCCTACTG AGCTTGTTCTACAGCACAGCACTCACTGTT ACA | 014 |
| murine Ig heavy chain type γ1/ transmembrane strech | GGGCTCTGGACGACCATCACCATCTTCAT CAGCCTCTTCCTGCTCAGTGTGTGC(TACA GCGCTGCTGTCACACTCTTCAAGGTA | 015 |
| murine Ig heavy chain type γ2B/ transmembrane strech | GGGCTCTGGACGACCATCACCATCTTCAT CAGCCTCTTCCTGCTCAGCGTGTGC(TACA GCGCCTCTGTCACACTCTTC) | 016 |
| murine Ig heavy chain type γ3/ transmembrane strech | GGGCTCTGGACGACCATCACCATCTTCAT CAGCCTCTTCCTGCTCAGCGTGTGCTACA GCGCCTCTGTCACCCTCTTC | 017 |
| murine Ig heavy chain type μ/ transmembrane strech | (AACCTGTGGACCACTGCCTCCACC)TTCA TCGTCCTCTTCCTCCTGAGCCTCTTCTACA GCACCACCGTCACCCTGTTC(AAGGTG) | 018 |
| human acetylcholine esterase/GPI-anchor signal peptide without optional linker peptide | GEAARRPGLPLPLLLLHQLLLLFLSHLRRL | 019 |
| human alkaline phosphatase (intestinal)/GPI-anchor signal peptide without optional linker peptide | DAAHPVAASLPLLAGTLLLLGASAAP | 020 |
| human alkaline phosphatase (liver)/ GPI-anchor signal peptide without optional linker peptide | SSAGSLAAGPLLVALALYPLSVLF | 021 |
| human alkaline phosphatase (placenta)/GPI-anchor signal peptide without optional linker peptide | DAAHPGRSVVPALLPLLAGTLLLLETATAP | 022 |
| human CAMPATH-1 antigen/GPI-anchor signal peptide without optional linker peptide | SASSNISGGIFLFFVANAIIHLFCFS | 023 |
| human carcinoembryonic antigen/ GPI-anchor signal peptide without optional linker peptide | ASGTSPGLSAGATVGIMIGVLVGVALI | 024 |
| human CD55 (decay accelerating factor)/GPI-anchor signal peptide without optional linker peptide | SGTTRLLSGHTCFTLTGLLGTLVTMGLLT | 025 |
| human CD59/GPI-anchor signal peptide without optional linker peptide | NGGTSLSEKTVLLLVTPFLAAAWSLHP | 026 |
| human CD90 (Thy-1) antigen/GPI-anchor signal peptide without optional linker peptide | CEGISLLAQNTSWLLLLLLSLSLLQATDFMSL | 027 |
| human contactin-1 (CNTN1)/GPI-anchor signal peptide without optional linker peptide | SGAPTLSPSLLGLLLPAFGILV | 028 |
| human E48 antigen/GPI-anchor signal peptide without optional linker peptide | DLCNEKLHNAAPTRTALAHSALSLGLALSLLA VILAPSL | 029 |
| human folate receptor A/GPI-anchor signal peptide without optional linker peptide | SGAGPWAAWPFLLSLALMLLWLLS | 030 |
| human folate receptor B/GPI-anchor signal peptide without optional linker peptide | NAGEMLHGTGGLLLSLALMLQLWLLG | 031 |

TABLE 2-continued

Examples of third nucleic acids and amino acids corresponding to third nucleic acids.

| source | nucleotide or amino acid sequence | SEQ ID NO: |
| --- | --- | --- |
| human GPI-anchored protein p137/GPI-anchor signal peptide without optional linker peptide | ARGLMNGYRGPAMDSEEDMMVTALHSLTL QTVVIHSLSSVLPGITLAIN | 032 |
| human lymphocyte function-associated antigen-3/GPI-anchor signal peptide without optional linker peptide | SSGHSRHRYALIPIPLAVITTCIVLYMNVL | 033 |
| human mDIA interacting protein (DIP)/GPI-anchor signal peptide without optional linker peptide | SGASSLHRHFGLLLASLAPLVLCLSLL | 034 |
| human 5'-nucleotidase/GPI-anchor signal peptide without optional linker peptide | STGSHCHGSFSLIFLSLWAVIFVLYQ | 035 |
| human urokinase plasminogen activator factor/GPI-anchor signal peptide without optional linker peptide | GAAPQPGPAHLSLTITLLMTARLWGGTLLWT | 036 |
| murine cell surface protein LY-6C antigen/GPI-anchor signal peptide without optional linker peptide | NAAVPTGASTWTMAGVLLFSLSSVILQTLL | 037 |
| murine Ly-6 antigen ThB/GPI-anchor signal peptide without optional linker peptide | NERLVSAAPGHALLSSVTLGLATSLSLLTVMA LCL | 038 |
| murine 5'-nucleotidase/GPI-anchor signal peptide without optional linker peptide | SAASHYQGSFPLVILSLSAVIFVLYQ | 039 |
| murine OX45 antigen (BCM-1 or Blast-1)/GPI-anchor signal peptide without optional linker peptide | SSGVCWTATWLVVTTLIIHRILLT | 040 |
| murine stem cell antigen 2/GPI-anchor signal peptide without optional linker peptide | NFSAAGLGLRASIPLLGLGLLLSLLALLQLSP | 041 |
| murine vascular cell adhesion molecule 1/GPI-anchor signal peptide without optional linker peptide | AKSFYFICYLCLYLAL | 042 |
| rat brevican protein/GPI-anchor signal peptide without optional linker peptide | GNSAEGSMPAFLLFLLLQLWDT | 043 |
| rat CD90 (Thy-1) antigen/GPI-anchor signal peptide without optional linker peptide | CGGISLLVQNTSWLLLLLLSLSFLQATDFISL | 044 |
| rat glypican protein/GPI-anchor signal peptide without optional linker peptide | SAATRPEPHYFFLLFLFTLVLAAARPRWR | 045 |
| rat MRC OX-45 antigen/GPI-anchor signal peptide without optional linker peptide | SSGVHWIAAWLVVTLSIIPSILLA | 046 |
| rat 5'-nucleotidase/GPI-anchor signal peptide without optional linker peptide | SAASHYQGSFPLIILSFWAVILVLYQ | 047 |
| rat pancreatic secretory granule membrane major glycoprotein GP2/GPI-anchor signal peptide without optional linker peptide | RNTGFLLAWPTFFLPVFLAWLF | 048 |

TABLE 2-continued

Examples of third nucleic acids and amino acids corresponding to third nucleic acids.

| source | nucleotide or amino acid sequence | SEQ ID NO: |
|---|---|---|
| rat T-cell surface protein RT6.2/GPI-anchor signal peptide without optional linker peptide | SSAGARESCVSLFLVVLPSLLVQLLCLAEP | 049 |
| yeast DNA repair protein PHR1/GPI-anchor signal peptide without optional linker peptide | SSGVKATQQMSMVKLVSIITIVTAFVGGMSVVF | 050 |
| yeast glycophospholipid-anchored surface protein 1/GPI-anchor signal peptide without optional linker peptide | NAATNVKANLAQVVFTSIISLSIAAGVGFALV | 051 |
| porcine amyloid precursor protein/GPI-anchor signal peptide without optional linker peptide | ARAAPTTSLGSLMTVSALAILGWSV | 052 |
| porcine dipeptidase/GPI-anchor signal peptide without optional linker peptide | SAAPSLHLPPGSLLASLVPLLLLSLP | 053 |
| Trypanosoma brucei variant surface protein IL Tat 1.1/GPI-anchor signal peptide without optional linker peptide | SNSFVIHKAPLFLAFLLF | 054 |
| Trypanosoma brucei variant surface protein MIT 117a/GPI-anchor signal peptide without optional linker peptide | DSSILVTKKFALTVVSAAFVALLF | 055 |
| Trypanosoma brucei variant surface protein MIT 118a/GPI-anchor signal peptide without optional linker peptide | NGSFLTSKQFAFSVVSAAFVALLF | 056 |
| Trypanosoma brucei variant surface protein MIT 221/GPI-anchor signal peptide without optional linker peptide | SNSFVISKTPLWLAVLLF | 057 |
| Trypanosoma brucei variant surface protein MITat 1.1000 BC/GPI-anchor signal peptide without optional linker peptide | DGSFLVNKKFALMVYDFVSLLAF | 058 |
| Trypanosoma brucei variant surface protein MITat 1.5b/GPI-anchor signal peptide without optional linker peptide | NGSFLTSKQFALMVSAAFVTLLF | 059 |
| Trypanosoma brucei procyclic acidic repetitive protein/GPI-anchor signal peptide without optional linker peptide | GAATLKSVALPFAIAAAALVAAF | 060 |
| Trypanosoma brucei variant surface protein TxTat 1/GPI-anchor signal peptide without optional linker peptide | SNSFVINKAPLLLGFLLF | 061 |
| Trypanosoma congolense variant surface protein YNat 1.1/GPI-anchor signal peptide without optional linker peptide | SGSSHGTKAIRSILHVALLM | 062 |
| chicken melanotransferrin/GPI-anchor signal peptide without optional linker peptide | AGNKLIQQHLLVITFVPFIILGQLQGLG | 063 |
| chicken neural cell adhesion molecule/GPI-anchor signal peptide without optional linker peptide | ATLGSPSTSSSFVSLLLSAVTLLLLC | 064 |

TABLE 2-continued

Examples of third nucleic acids and amino acids corresponding to third nucleic acids.

| source | nucleotide or amino acid sequence | SEQ ID NO: |
|---|---|---|
| Torpedo marmorata acetylcholine esterase/GPI-anchor signal peptide without optional linker peptide | SSSGTSSSKGIIFYVLFSILYLIFY | 065 |
| hamster prion protein/GPI-anchor signal peptide without optional linker peptide | SSAVLFSSPPVILLISFLIFLMVG | 066 |
| bovine 5'-nucleotidase/GPI-anchor signal peptide without optional linker peptide | SAGSHCCGSFSLIFLSVLAVIIILYQ | 067 |
| slime mold membrane protein Gp64/ GPI-anchor signal peptide without optional linker peptide | SSATTIAFNAFVVFAIVLSVLLF | 068 |
| slime mold pre-spore specific antigen/ GPI-anchor signal peptide without optional linker peptide | GSASTVVASLSLIIFSMILSLC | 069 |
| human fibroblast growth factor receptor 1 | TCGCCCCTGTACCTGGAGATCATCATCTAT TGCACAGGGGCCTTCCTCATCTCCTGCAT GGTGGGGTCGGTCATCGTCTAC | 160 |
| murine epithelial growth factor receptor | AAGATACCATCTATTGCCACTGGGATTGT GGGTGGCCTCCTCTTCATAGTGGTGGTGG CCCTTGGGATTGGCCTATTCATGCGAAGA CGT | 161 |
| human complement receptor 1 (C3b/C4b) | THDALIVGTLSGTIFFILLIIFLSWIILK | 162 |
| human interleukin receptor 4 | TTCGAGCAGCACCTCCTGCTGGGCGTCAG CGTTTCCTGCATTGTCA TCCTGGCCGTCTGCCTGTTGTGCTATGTC AGCATCACCAA-GATTAAG | 174 |
| murine interleukin 4 receptor | CGCCTTCCACTGGGGGTCACCATCTCCTG CCTCTGCATCCCGTTGTTTTGCCTGTTCTG TTACTTCAGCATTACCAAGATT | 163 |
| human immunoglobulin α heavy chain/transmembrane strech | ACCATCACCTTCCTCACCCTCTTCCTGCTG AGCCTGTTCTATAGCACAGCACTGACCGT GACC | 164 |
| human immunoglobulin ε heavy chain/ transmembrane strech | TGGACGTGGACCGGCCTCTGCATCTTCGC CGCACTCTTCCTGCTCAGCGTGAGCTACA GCGCCGCCATCACGCTCCTCATGGTGCAG | 165 |
| human immunoglobulin γ3 heavy chain/transmembrane strech | GGGCTGTGGACGACCATCACCATCTTCAT CACACTCTTCCTGTTAAGCGTGTGCTACAG TGCCACCGTCACCTTCTTC | 166 |
| human immunoglobulin γ4 heavy chain/transmembrane strech | GGGCTGTGGACGACCATCACCATCTTCAT CACACTCTTCCTGCTAAGCGTGTGCTACA GTGCCACCGTCACCTTCTTC | 175 |
| murine Ig heavy chain type ε/ transmembrane strech | GAGCTGTGGACCAGTATTTGTGTCTTCATC ACCCTGTTCCTGCTCAGTGTGAGCTATGG GGCCACTGTCACCGTCCTC | 167 |
| murine Ig heavy chain type δ/ transmembrane strech | GGCCTGTGGCCCACAATGTGCACCTTCGT GGCCCTCTTCCTGCTCACACTGCTCTACA GTGGCTTCGTCACCTTCATCAAGGTA | 176 |
| murine Ig heavy chain type γ2A/ transmembrane strech | GGGCTCTGGACAACCATCACCATCTTCAT CAGCCTCTTCCTGCTCAGCGTGTGTTACA GCGCCTCTGTCACACTCTTC | 168 |

TABLE 3

Examples of fourth nucleic acids and amino acids corresponding to fourth nucleic acids.

| source | nucleotide or amino acid sequence | SEQ ID NO: |
|---|---|---|
| human immunoglobulin δ heavy chain | ACCTGGCCATGACCCCCTGATCCC | 070 |
| human immunoglobulin γ1 heavy chain | AGCTGCAACTGGAGGAGAGCTGTGCGGAG | 071 |
| human immunoglobulin γ2 heavy chain | AGCTGCAACTGGAGGAGAGCTGTGCGGAGGCGC | 072 |
| human immunoglobulin μ heavy chain | AGGGGGAGGTGAGCGCCGACGAGGA | 073 |
| murine Ig heavy chain type α | AACGTCAAGAGCCACTTTCCTATGTGCTACT | 074 |
| murine Ig heavy chain type γ1 | GGCTGCAACTGGACGAGACCTGTGCTGAGGCCCAGGACGGGGAGCTGG | 075 |
| murine Ig heavy chain type γ2B | GGCTAGACCTGGATGATATCTGTGCTG | 076 |
| murine Ig heavy chain type γ3 | AGCTGGAACTGAATGAGACCTGT | 077 |
| murine Ig heavy chain type μ | AGGGGGAGGTGAATGCTGAGGAGGAAGGCTTTG | 078 |
| human acetylcholine esterase | GFTH | 079 |
| human alkaline phosphatase (intestinal) | ACTT | 080 |
| human alkaline phosphatase (liver) | CAPA | 081 |
| human alkaline phosphatase (placenta) | AGTT | 082 |
| human CAMPATH-1 antigen | TSSP | 083 |
| human carcinoembryonic antigen | ITVS | 084 |
| human CD55 (decay accelerating factor) | SGTT | 085 |
| human CD59 | EQLE | 086 |
| human CD90 (Thy-1) antigen | KLVK | 087 |
| human contactin-1 (CNTN1) | QVKI | 088 |
| human E48 antigen | CCQE | 089 |
| human folate receptor A | AAAM | 090 |
| human folate receptor B | AMHV | 091 |
| human GPI-anchored protein p137 | GSRG | 092 |
| human lymphocyte function-associated antigen-3 | TCIP | 093 |
| human mDIA interacting protein (DIP) | YGYS | 094 |
| human 5'-nucleotidase | RIKF | 095 |
| human urokinase plasminogen activator factor | QYRS | 096 |
| murine cell surface protein LY-6C antigen | EDLC | 097 |
| murine Ly-6 antigen ThB | TDLC | 098 |
| murine 5'-nucleotidase | RIKF | 099 |
| murine OX45 antigen (BCM-1 or Blast-1) | DLAR | 100 |
| murine stem cell antigen 2 | SSFC | 101 |

TABLE 3-continued

Examples of fourth nucleic acids and amino acids corresponding to fourth nucleic acids.

| source | nucleotide or amino acid sequence | SEQ ID NO: |
|---|---|---|
| murine vascular cell adhesion molecule 1 | HLMF | 102 |
| rat brevican protein/GPI-anchor | APSS | 103 |
| rat CD90 (Thy-1) antigen | KLVK | 104 |
| rat glypican protein | GQKT | 105 |
| rat MRC OX-45 antigen | TLAR | 106 |
| rat 5'-nucleotidase | RIKF | 107 |
| rat pancreatic secretory granule membrane major glycoprotein GP2 | NGTP | 108 |
| rat T-cell surface protein RT6.2 | NCLY | 109 |
| yeast DNA repair protein PHR1 | GSSS | 110 |
| yeast glycophospholipid-anchored surface protein 1/GPI-anchor | SSKK | 111 |
| porcine amyloid precursor protein | EPLS | 112 |
| porcine dipeptidase | NYGY | 113 |
| *Trypanosoma brucei* variant surface protein IL Tat 1.1 | NTTG | 114 |
| *Trypanosoma brucei* variant surface protein MIT 117a | NACK | 115 |
| *Trypanosoma brucei* variant surface protein MIT 118a | EKCR | 116 |
| *Trypanosoma brucei* variant surface protein MIT 221 | TTGS | 117 |
| *Trypanosoma brucei* variant surface protein MITat 1.1000 BC | EKCC | 118 |
| *Trypanosoma brucei* variant surface protein MITat 1.5b | EDCR | 119 |
| *Trypanosoma brucei* procyclic acidic repetitive protein | EPEP | 120 |
| *Trypanosoma brucei* variant surface protein TxTat 1 | NTTA | 121 |
| *Trypanosoma congolense* variant surface protein YNat 1.1 | SHLP | 122 |
| chicken melanotransferrin | QCSG | 123 |
| chicken neural cell adhesion molecule | TVIP | 124 |
| *Torpedo marmorata* acetylcholine esterase | DGEL | 125 |
| hamster prion protein | DGRR | 126 |
| bovine 5'-nucleotidase | RIQF | 127 |
| slime mold membrane protein Gp64 | NNVC | 128 |
| slime mold pre-spore specific antigen | STTT | 129 |

In one embodiment is the polypeptide an immunoglobulin heavy chain and the transmembrane domain is that of an immunoglobulin heavy chain. For the expression of an immunoglobulin the nucleic acid of the current invention is introduced together with a nucleic acid encoding an immunoglobulin light chain into a eukaryotic host cell. These nucleic acids can be located on the same nucleic acid or on different nucleic acids.

The invention encompasses a vector comprising the nucleic acid of the invention as well as a eukaryotic cell comprising the vector of the invention.

The soluble variant of the heterologous polypeptide encoded by the nucleic acid according to the invention can be produced by transfecting a eukaryotic cell with the nucleic acid of the invention, culturing the cell under conditions suitable for the expression of the polypeptide encoded by said nucleic acid, and recovering the polypeptide from the cytoplasm of the cells or the culture medium.

For the manufacture of a eukaryotic cell according to the invention a kit is provided. The kit comprises a vector containing at least two multiple cloning sites and a spliceable nucleic acid beginning with a 5' splice donor site and terminated by a 3' splice acceptor site, wherein i) the nucleic acid comprises a translational stop codon and a polyadenylation signal, and ii) the nucleic acid is not constitutively removed during pre-mRNA processing.

In one embodiment the eukaryotic cell of the invention is a mammalian cell. In one embodiment the mammalian cell is a cell selected from the group comprising CHO cells, NS0 cells, Sp2/0 cells, COS cells, K652 cells, BHK cells, PER.C6® cells and HEK cells.

The following examples, sequence listing and figures are provided to aid the understanding of the present invention, the true scope of which is set forth in the appended claims. It is understood that modifications can be made in the procedures set forth without departing from the spirit of the invention.

DESCRIPTION OF THE TABLES

Figure 1:
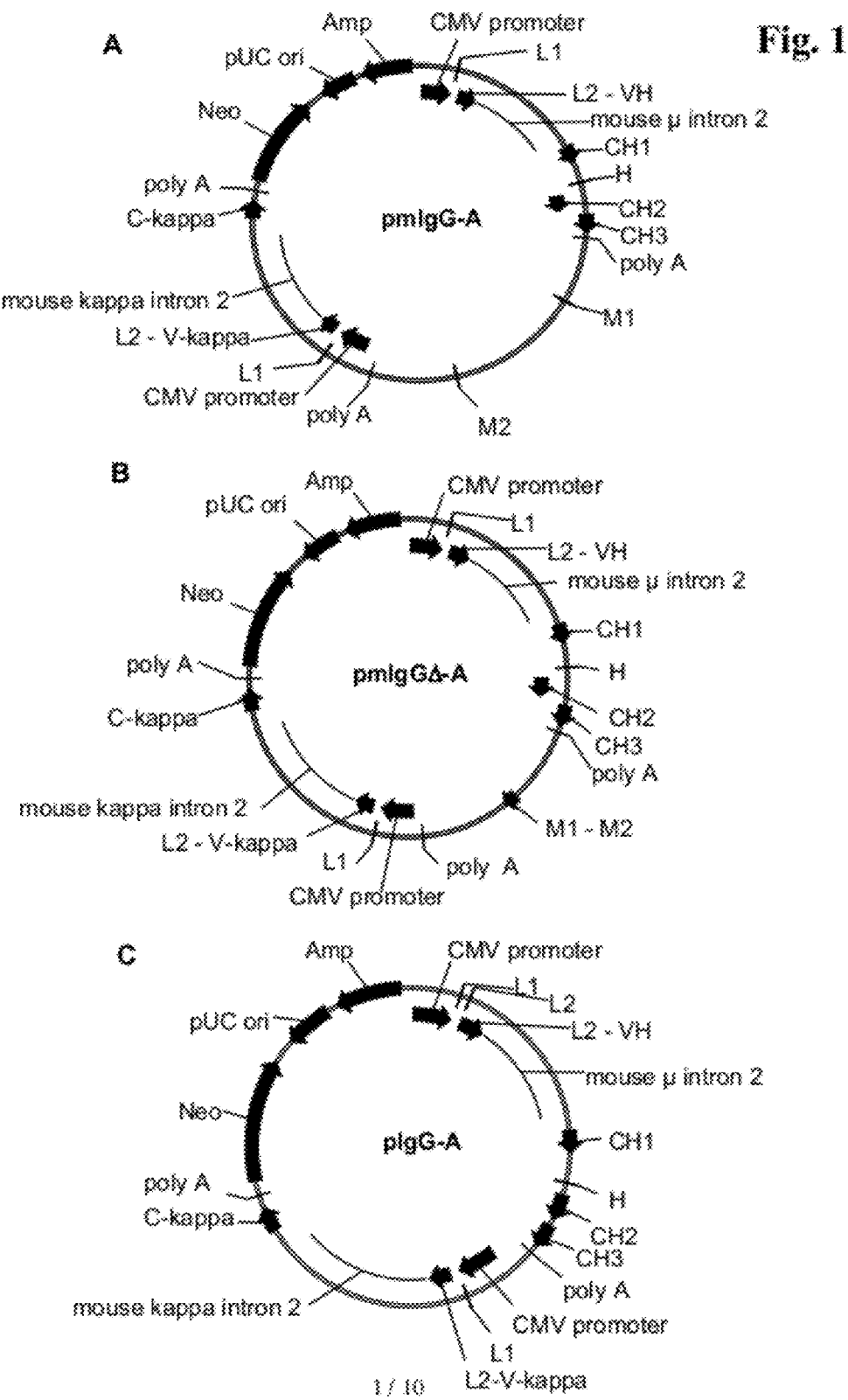
FIG. 1: Plasmid cards of the sIgG/mIgG expression vector pmIgG-A (A), the sIgG/mIgG expression vector pmIgGΔ-A (B), and the sIgG expression vector pIgG-A (C). The depicted vector elements are described in detail in the text.

Table 1 Examples of second nucleic acids.
Table 2 Examples of third nucleic acids and amino acids corresponding to third nucleic acids.
Table 3 Examples of fourth nucleic acids and amino acids corresponding to fourth nucleic acids.
Table 4 Oligonucleotide primer for cloning and mutagenesis in the construction of the sIgG/mIgG expression vector 'pmIgG-A'
Table 5 Average SPR determined for every selected clone based on four distinct SPRs calculated at several time points during the exponential growth phase.
Table 6 Table 4 shows the distribution of clones to different IgG concentration levels three weeks after single cell depositions into 96 well plates and analysis of cell culture supernatants of 515 mIgG-sorted clones, and of 550 control clones by ELISA.
Table 7 Table 5 shows the distribution of clones to different IgG concentration levels in the second selection.
Table 8 Cell count of shaker cultures on day 0, 1, 2, 3, 4, and 7 of every clone determined with a CASY® TT cell counter (Scharfe Systems).
Table 9 Productivity determination of 10 day shaker cultures by ELISA.

DESCRIPTION OF THE SEQUENCES

SEQ ID NO: 001 Second nucleic acid derived from human immunoglobulin δ heavy chain
SEQ ID NO: 002 Second nucleic acid derived from human immunoglobulin γ1 heavy chain
SEQ ID NO: 003 Second nucleic acid derived from human immunoglobulin γ2 heavy chain
SEQ ID NO: 004 Second nucleic acid derived from human immunoglobulin μ heavy chain
SEQ ID NO: 005 Second nucleic acid derived from murine immunoglobulin heavy chain type α
SEQ ID NO: 006 Second nucleic acid derived from murine immunoglobulin heavy chain type γ1
SEQ ID NO: 007 Second nucleic acid derived from murine immunoglobulin heavy chain type γ2B
SEQ ID NO: 008 Second nucleic acid derived from murine immunoglobulin heavy chain type γ3
SEQ ID NO: 009 Second nucleic acid derived from murine immunoglobulin heavy chain type μ
SEQ ID NO: 010 Third nucleic acid derived from human immunoglobulin δ heavy chain
SEQ ID NO: 011 Third nucleic acid derived from human immunoglobulin γ1 heavy chain
SEQ ID NO: 012 Third nucleic acid derived from human immunoglobulin γ2 heavy chain
SEQ ID NO: 013 Third nucleic acid derived from human immunoglobulin μ heavy chain
SEQ ID NO: 014 Third nucleic acid derived from murine immunoglobulin heavy chain type α
SEQ ID NO: 015 Third nucleic acid derived from murine immunoglobulin heavy chain type γ1
SEQ ID NO: 016 Third nucleic acid derived from murine immunoglobulin heavy chain type γ2B
SEQ ID NO: 017 Third nucleic acid derived from murine immunoglobulin heavy chain type γ3
SEQ ID NO: 018 Third nucleic acid derived from murine immunoglobulin heavy chain type μ
SEQ ID NO: 019 Third nucleic acid derived from human AChE
SEQ ID NO: 020 Third nucleic acid derived from human intestinal alkaline phosphatase
SEQ ID NO: 021 Third nucleic acid derived from human liver alkaline phosphatase
SEQ ID NO: 022 Third nucleic acid derived from human placenta alkaline phosphatase
SEQ ID NO: 023 Third nucleic acid derived from human CAMPATH-1 antigen
SEQ ID NO: 024 Third nucleic acid derived from human carcinoembryonic antigen
SEQ ID NO: 025 Third nucleic acid derived from human CD55
SEQ ID NO: 026 Third nucleic acid derived from human CD59
SEQ ID NO: 027 Third nucleic acid derived from human CD90
SEQ ID NO: 028 Third nucleic acid derived from human contactin-1
SEQ ID NO: 029 Third nucleic acid derived from human E48 antigen
SEQ ID NO: 030 Third nucleic acid derived from human folate receptor A
SEQ ID NO: 031 Third nucleic acid derived from human folate receptor B
SEQ ID NO: 032 Third nucleic acid derived from human GPI-anchored protein p137
SEQ ID NO: 033 Third nucleic acid derived from human lymphocyte function-associated antigen-3
SEQ ID NO: 034 Third nucleic acid derived from human mDIA interacting protein
SEQ ID NO: 035 Third nucleic acid derived from human 5'-nucleotidase
SEQ ID NO: 036 Third nucleic acid derived from human urokinase plasminogen activator factor
SEQ ID NO: 037 Third nucleic acid derived from murine cell surface protein LY-6C antigen
SEQ ID NO: 038 Third nucleic acid derived from murine Ly-6 antigen ThB
SEQ ID NO: 039 Third nucleic acid derived from murine 5'-nucleotidase
SEQ ID NO: 040 Third nucleic acid derived from murine OX45 antigen
SEQ ID NO: 041 Third nucleic acid derived from murine stem cell antigen 2
SEQ ID NO: 042 Third nucleic acid derived from murine vascular cell adhesion molecule 1
SEQ ID NO: 043 Third nucleic acid derived from rat brevican
SEQ ID NO: 044 Third nucleic acid derived from rat CD90 antigen
SEQ ID NO: 045 Third nucleic acid derived from rat glypican
SEQ ID NO: 046 Third nucleic acid derived from rat MRC OX45 antigen
SEQ ID NO: 047 Third nucleic acid derived from rat 5'-nucleotidase
SEQ ID NO: 048 Third nucleic acid derived from rat pancreatic secretory granule membrane major glycoprotein GP2
SEQ ID NO: 049 Third nucleic acid derived from rat T-cell surface protein RT6.2
SEQ ID NO: 050 Third nucleic acid derived from yeast DNA repair protein PHR1

SEQ ID NO: 051 Third nucleic acid derived from yeast glycophospholipid-anchored surface protein-1
SEQ ID NO: 052 Third nucleic acid derived from porcine amyloid precursor protein
SEQ ID NO: 053 Third nucleic acid derived from porcine dipeptidase
SEQ ID NO: 054 Third nucleic acid derived from *Trypanosoma brucei* variant surface protein IL Tat 1.1
SEQ ID NO: 055 Third nucleic acid derived from *Trypanosoma brucei* variant surface protein MIT 117a
SEQ ID NO: 056 Third nucleic acid derived from *Trypanosoma brucei* variant surface protein MIT 118a
SEQ ID NO: 057 Third nucleic acid derived from *Trypanosoma brucei* variant surface protein MIT 221
SEQ ID NO: 058 Third nucleic acid derived from *Trypanosoma brucei* variant surface protein MITat 1.1000 BC
SEQ ID NO: 059 Third nucleic acid derived from *Trypanosoma brucei* variant surface protein MITat 1.5b
SEQ ID NO: 060 Third nucleic acid derived from *Trypanosoma brucei* procyclic acidic repetitive protein
SEQ ID NO: 061 Third nucleic acid derived from *Trypanosoma brucei* variant surface protein TxTat 1
SEQ ID NO: 062 Third nucleic acid derived from *Trypanosoma congolense* variant surface protein YNat 1.1
SEQ ID NO: 063 Third nucleic acid derived from chicken melanotransferrin
SEQ ID NO: 064 Third nucleic acid derived from chicken neural cell adhesion molecule
SEQ ID NO: 065 Third nucleic acid derived from *Torpedo marmorata* AChE
SEQ ID NO: 066 Third nucleic acid derived from hamster prion protein
SEQ ID NO: 067 Third nucleic acid derived from bovine 5'-nucleotidase
SEQ ID NO: 068 Third nucleic acid derived from slime mold membrane protein Gp64
SEQ ID NO: 069 Third nucleic acid derived from slime mold pre-spore specific antigen
SEQ ID NO: 070 Fourth nucleic acid derived from human immunoglobulin δ heavy chain
SEQ ID NO: 071 Fourth nucleic acid derived from human immunoglobulin γ1 heavy chain
SEQ ID NO: 072 Fourth nucleic acid derived from human immunoglobulin γ2 heavy chain
SEQ ID NO: 073 Fourth nucleic acid derived from human immunoglobulin μ heavy chain
SEQ ID NO: 074 Fourth nucleic acid derived from murine immunoglobulin heavy chain type α
SEQ ID NO: 075 Fourth nucleic acid derived from murine immunoglobulin heavy chain type γ1
SEQ ID NO: 076 Fourth nucleic acid derived from murine immunoglobulin heavy chain type γ2B
SEQ ID NO: 077 Fourth nucleic acid derived from murine immunoglobulin heavy chain type γ3
SEQ ID NO: 078 Fourth nucleic acid derived from murine immunoglobulin heavy chain type μ
SEQ ID NO: 079 Fourth nucleic acid derived from human AChE
SEQ ID NO: 080 Fourth nucleic acid derived from human intestinal alkaline phosphatase
SEQ ID NO: 081 Fourth nucleic acid derived from human liver alkaline phosphatase
SEQ ID NO: 082 Fourth nucleic acid derived from human placenta alkaline phosphatase
SEQ ID NO: 083 Fourth nucleic acid derived from human CAMPATH-1 antigen
SEQ ID NO: 084 Fourth nucleic acid derived from human carcinoembryonic antigen
SEQ ID NO: 085 Fourth nucleic acid derived from human CD55
SEQ ID NO: 086 Fourth nucleic acid derived from human CD59
SEQ ID NO: 087 Fourth nucleic acid derived from human CD90
SEQ ID NO: 088 Fourth nucleic acid derived from human contactin-1
SEQ ID NO: 089 Fourth nucleic acid derived from human E48 antigen
SEQ ID NO: 090 Fourth nucleic acid derived from human folate receptor A
SEQ ID NO: 091 Fourth nucleic acid derived from human folate receptor B
SEQ ID NO: 092 Fourth nucleic acid derived from human GPI-anchored protein p137
SEQ ID NO: 093 Fourth nucleic acid derived from human lymphocyte function-associated antigen-3
SEQ ID NO: 094 Fourth nucleic acid derived from human mDIA interacting protein
SEQ ID NO: 095 Fourth nucleic acid derived from human 5'-nucleotidase
SEQ ID NO: 096 Fourth nucleic acid derived from human urokinase plasminogen activator factor
SEQ ID NO: 097 Fourth nucleic acid derived from murine cell surface protein LY-6C antigen
SEQ ID NO: 098 Fourth nucleic acid derived from murine Ly-6 antigen ThB
SEQ ID NO: 099 Fourth nucleic acid derived from murine 5'-nucleotidase
SEQ ID NO: 100 Fourth nucleic acid derived from murine OX45 antigen
SEQ ID NO: 101 Fourth nucleic acid derived from murine stem cell antigen 2
SEQ ID NO: 102 Fourth nucleic acid derived from murine vascular cell adhesion molecule 1
SEQ ID NO: 103 Fourth nucleic acid derived from rat brevican
SEQ ID NO: 104 Fourth nucleic acid derived from rat CD90 antigen
SEQ ID NO: 105 Fourth nucleic acid derived from rat glypican
SEQ ID NO: 106 Fourth nucleic acid derived from rat MRC OX45 antigen
SEQ ID NO: 107 Fourth nucleic acid derived from rat 5'-nucleotidase
SEQ ID NO: 108 Fourth nucleic acid derived from rat pancreatic secretory granule membrane major glycoprotein GP2
SEQ ID NO: 109 Fourth nucleic acid derived from rat T-cell surface protein RT6.2
SEQ ID NO: 110 Fourth nucleic acid derived from yeast DNA repair protein PHR1
SEQ ID NO: 111 Fourth nucleic acid derived from yeast glycophospholipid-anchored surface protein-1
SEQ ID NO: 112 Fourth nucleic acid derived from porcine amyloid precursor protein
SEQ ID NO: 113 Fourth nucleic acid derived from porcine dipeptidase
SEQ ID NO: 114 Fourth nucleic acid derived from *Trypanosoma brucei* variant surface protein IL Tat 1.1
SEQ ID NO: 115 Fourth nucleic acid derived from *Trypanosoma brucei* variant surface protein MIT 117a
SEQ ID NO: 116 Fourth nucleic acid derived from *Trypanosoma brucei* variant surface protein MIT 118a SEQ ID NO: 117 Fourth nucleic acid derived from *Trypanosoma brucei* variant surface protein MIT 221
SEQ ID NO: 118 Fourth nucleic acid derived from *Trypanosoma brucei* variant surface protein MITat 1.1000 BC
SEQ ID NO: 119 Fourth nucleic acid derived from *Trypanosoma brucei* variant surface protein MITat 1.5b
SEQ ID NO: 120 Fourth nucleic acid derived from *Trypanosoma brucei* procyclic acidic repetitive protein
SEQ ID NO: 121 Fourth nucleic acid derived from *Trypanosoma brucei* variant surface protein TxTat 1
SEQ ID NO: 122 Fourth nucleic acid derived from *Trypanosoma congolense* variant surface protein YNat 1.1
SEQ ID NO: 123 Fourth nucleic acid derived from chicken melanotransferrin
SEQ ID NO: 124 Fourth nucleic acid derived from chicken neural cell adhesion molecule
SEQ ID NO: 125 Fourth nucleic acid derived from *Torpedo marmorata* AChE
SEQ ID NO: 126 Fourth nucleic acid derived from hamster prion protein
SEQ ID NO: 127 Fourth nucleic acid derived from bovine 5'-nucleotidase
SEQ ID NO: 128 Fourth nucleic acid derived from slime mold membrane protein Gp64
SEQ ID NO: 129 Fourth nucleic acid derived from slime mold pre-spore specific antigen
SEQ ID NO: 130 Human immunoglobulin heavy constant gamma 1 (IGHG1) gene including the exons from CH1 to CH3 with all intervening introns, and the adjacent 3' untranslated region.
SEQ ID NO: 131 Amino acid sequence of the γ-chain constant region encoded by plasmid pIgG-A.
SEQ ID NO: 132 Oligonucleotide primer TM-fw1
SEQ ID NO: 133 Oligonucleotide primer TM-rv1
SEQ ID NO: 134 Oligonucleotide primer M1-rv
SEQ ID NO: 135 Oligonucleotide primer M2-fw
SEQ ID NO: 136 Oligonucleotide primer TM-fw2
SEQ ID NO: 137 Oligonucleotide primer TM-rv2
SEQ ID NO: 138 Oligonucleotide primer mutSphI-1
SEQ ID NO: 139 Oligonucleotide primer mut SphI-2
SEQ ID NO: 140 Human immunoglobulin heavy constant gamma 1 (IGHG1) gene including the exons from CH1 to M2 with all intervening introns, the polyadenylation site for the secreted form of IgG1 in intron 6, and the 3'UTR containing the polyadenylation site for the membrane bound form of IgG1.
SEQ ID NO: 141 The amino acid sequences of the short (sIgG) isoform encoded by plasmid pmIgG-A.
SEQ ID NO: 142 Amino acid sequences of the long (mIgG) isoform of the γ-chain constant region encoded by plasmid pmIgG-A.
SEQ ID NO: 143 Human IGHG1 gene including the exons from CH1 to CH3 with all intervening introns, and the adjacent 5' part of intron 6 including the polyadenylation site for the secreted form of the immunoglobulin.
SEQ ID NO: 144 The amino acid sequences of the short (sIgG) isoform of the γ-chain constant region encoded by plasmid pmIgGΔ-A.
SEQ ID NO: 145 Amino acid sequences of the long (mIgG) isoform of the γ-chain constant region encoded by plasmid pmIgGΔ-A.
SEQ ID NO: 146 Encoded sequence removed from plasmid pmIgGΔ-B
SEQ ID NO: 147 Encoded sequence inserted for the generation of plasmid pIgG-GPI-B (amino acid sequence of the carboxy-terminal signal peptide of the human placental alkaline phosphatase (NCBI accession: M13077; nucleotides: 1542-1643))
SEQ ID NO: 148 DNA sequence of the gamma-chain expression cassette constant region, from CH1 to 3'UTR of expression plasmid pIgG-GPI-B
SEQ ID NO: 149 Amino acid sequence of the sIgG isoform of the gamma-chain constant region encoded by plasmid pIgG-GPI-B
SEQ ID NO: 150 Amino acid sequence of the long isoform of the gamma-chain constant region including the carboxy-terminal signal peptide of the human placental alkaline phosphatase encoded by plasmid pIgG-GPI-B
SEQ ID NO: 151 Second nucleic acid derived from human fibroblast growth factor receptor 1
SEQ ID NO: 152 Second nucleic acid derived from murine epithelial growth factor receptor
SEQ ID NO: 153 Second nucleic acid derived from human complement receptor 1 (C3b/C4b)
SEQ ID NO: 154 Second nucleic acid derived from murine interleukin 4 receptor
SEQ ID NO: 155 Second nucleic acid derived from human immunoglobulin α heavy chain
SEQ ID NO: 156 Second nucleic acid derived from human immunoglobulin ε heavy chain (1)
SEQ ID NO: 157 Second nucleic acid derived from human immunoglobulin γ3 heavy chain
SEQ ID NO: 158 Second nucleic acid derived from murine Ig heavy chain type ε
SEQ ID NO: 159 Second nucleic acid derived from murine Ig heavy chain type γ2A
SEQ ID NO: 160 Third nucleic acid derived from human fibroblast growth factor receptor 1
SEQ ID NO: 161 Third nucleic acid derived from murine epithelial growth factor receptor
SEQ ID NO: 162 Third nucleic acid derived from human complement receptor 1 (C3b/C4b)
SEQ ID NO: 163 Third nucleic acid derived from murine interleukin 4 receptor
SEQ ID NO: 164 Third nucleic acid derived from human immunoglobulin α heavy chain
SEQ ID NO: 165 Third nucleic acid derived from human immunoglobulin ε heavy chain
SEQ ID NO: 166 Third nucleic acid derived from human immunoglobulin γ3 heavy chain
SEQ ID NO: 167 Third nucleic acid derived from murine Ig heavy chain type ε
SEQ ID NO: 168 Third nucleic acid derived from murine Ig heavy chain type γ2A
SEQ ID NO: 169 Second nucleic acid derived from human interleukin 4 receptor
SEQ ID NO: 170 Second nucleic acid derived from human immunoglobulin ε heavy chain (2)
SEQ ID NO: 171 Second nucleic acid derived from human immunoglobulin γ4 heavy chain
SEQ ID NO: 172 Second nucleic acid derived from murine immunoglobulin δ heavy chain
SEQ ID NO: 173 Second nucleic acid derived from human immunoglobulin ε heavy chain (2)
SEQ ID NO: 174 Third nucleic acid derived from human interleukin 4 receptor
SEQ ID NO: 175 Third nucleic acid derived from human immunoglobulin γ4 heavy chain
SEQ ID NO: 176 Third nucleic acid derived from murine Ig heavy chain type δ

EXAMPLES

Example 1

Cloning of Genomic Fragments and Construction of Eukaryotic sIgG/mIgG Expression Vectors a) Construction of the sIgG Expression Vector 'pIgG-A'

For the expression of an immunoglobulin with specificity against a protein "A" the vector 'pIgG-A' was constructed. It codes for the secreted sIgG form of the immunoglobulin and comprises the following elements (see FIG. 1C):

1. A transcription unit for a human gamma (γ) 1 heavy chain, composed of
   - the immediate early enhancer and promoter from the human cytomegalovirus (hCMV),
   - a synthetic 5' untranslated region including a Kozak consensus sequence (Kozak, M., Nucleic Acids Res. 15 (1987) 8125-48),
   - a murine immunoglobulin heavy chain signal sequence including the signal sequence intron,
   - a variable heavy chain cDNA of an antibody with specificity against a protein "A",
   - a mouse/human heavy chain hybrid intron 2 including the mouse Ig μ enhancer ($J_H3$-$J_H4$ switch region) joined with the human immunoglobulin heavy constant gamma 1 (IGHG1) gene including the exons from CH1 to CH3 with all intervening introns, and the adjacent 3' untranslated region containing the polyadenylation site for the heavy chain of the secreted form of IgG1.

The nucleotide sequence of the heavy chain constant region is reported in SEQ ID NO: 130. The amino acid sequence of the γ-chain constant region encoded by plasmid pIgG-A is reported in SEQ ID NO: 131.

2. A transcription unit for a human kappa (κ) light chain, composed of
   - the immediate early enhancer and promoter from the human cytomegalovirus (hCMV),
   - a synthetic 5' untranslated region including a Kozak consensus sequence,
   - a murine immunoglobulin heavy chain signal sequence including the signal sequence intron,
   - a variable κ chain cDNA of an antibody with specificity against a protein "A"
   - the mouse intron 2 Ig κ enhancer joined with the human immunoglobulin kappa constant (IGKC) gene, and
   - the human IGKC gene 3' untranslated region containing the polyadenylation site.
3. A neomycin phosphotransferase transcription unit as a selectable marker for mammalian cells.
4. An origin of replication from the vector pUC18 for the replication of the plasmid in E. coli.
5. A beta-lactamase gene conferring ampicillin resistance in E. coli.

b) Construction of the sIgG/mIgG Expression Vector 'pmIgG-A'

A 5.2 kb genomic fragment of the human immunoglobulin heavy constant gamma 1 (IGHG1) locus comprising the main part of the intron downstream of exon CH3 (intron 6), the exon M1, the intron downstream of exon M1 (intron 7), the exon M2, and the adjacent 3' untranslated region (3'UTR), including the polyadenylation signal for the membrane bound form of the gamma 1 chain, was amplified from human genomic DNA (Roche Diagnostics GmbH, Mannheim, Germany) by PCR using the Expand Long Template PCR System (Roche Diagnostics GmbH, Germany) and the oligonucleotide primer specified in Table 4.

TABLE 4

Oligonucleotide primer for cloning and mutagenesis.

| Use for | Name | Sequence (in 5' to 3' direction) | SEQ ID NO: |
|---|---|---|---|
| Amplification of 5.2 kb genomic IGHG1 fragment | TM-fw1 | GGCCGAGTCTGAGGCCTGAGT GGCATGAGGGAGGCAGAGT | 132 |
| | TM-rv1 | AACTGGATCCATGTAGAAAAGA GGAGAAGCCCCGGGGGTCCAT GTAGT | 133 |
| Amplification of 1.1 kb genomic IGHG3 fragment | TM-fw1 | GGCCGAGTCTGAGGCCTGAGT GGCATGAGGGAGGCAGAGT | 132 |
| | M1-rv | GATCCACTTCACCTTGAAGAAG GTGACGGTGGCACTGTAGCAC ACGC | 134 |
| Amplification of 1.6 kb genomic IGHG4 fragment | M2-fw | CACCTTCTTCAAGGTGAAGTGG ATCTTCTCCTCGGTGGTGGACC TGAAG | 135 |
| | TM-rv1 | AACTGGATCCATGTAGAAAAGA GGAGAAGCCCCGGGGGTCCAT GTAGT | 133 |
| Amplification of the joined IGHG3-IGHG4 fragment | TM-fw2 | CTCCAGCAGCAGCTGCCCTGG GCTGGGCCACGA | 136 |
| | TM-rv2 | CAGGGATCCCCCGAGGTGCAG CTGGACCAGCCTCCTCCTGACC GTGTTTT | 137 |
| Mutation of the Sph I site in the 3'UTR | mutSphI-1 | CTACCCCAGACCTCCGCTGCTT GGTGCcTGCAGGGCACTGGGG GCCAGGTGTCCCCTCAGCAGG ACGT* | 138 |
| | mutSphI-2 | CCTGCTGAGGGGACACCTGGC CCCCAGTGCCCTGCAgGCACCA AGCAGCGGAGGTCTGGGGT* | 139 |

*The altered nucleotides for the mutagenesis of the Sph I site are indicated by lower case letters.

Figure 2:
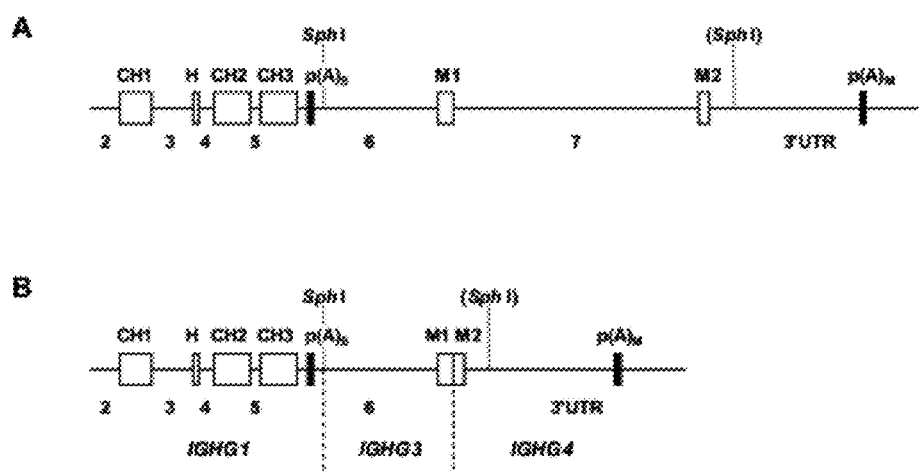
FIG. 2: Schematic depiction of the exon intron structures of the gamma chain expression cassettes.
  A: Structure of the gamma 1 chain constant region in the expression vector pmIgG-A. The approx. 7.2 kb DNA fragment is displayed as a black line. Exons are represented by clear boxes with their designations indicated above. The position of the polyadenylation site for the secreted form [p(A)s] and for the membrane bound form [p(A)$_M$] of the IgG are displayed by black bars. The numbering of the introns and the 3'UTR are indicated below the diagram. The relative positions of the Sph I restriction site in intron 6 and the mutated Sph I site in the 3'UTR (in parentheses) are shown.
  B: Structure of the approx. 4.8 kb hybrid gamma 1—gamma 3—gamma 4 chain constant region in the expression vector pmIgGΔ-A as depicted in A. Additionally the diagram indicates the regions derived from the three immunoglobulin heavy constant gamma gene loci (IGHG1, IGHG3, and IGHG4).

The amplified fragment corresponds to the nucleotides 87203513-87208691 of the "*Homo sapiens* chromosome 14 genomic contig" (NCBI accession: NT_026437, reverse complement). Sequencing of the subcloned PCR product revealed an identity of 98 percent compared to the corresponding chromosome 14 sequence with all differences found in introns or the 3' untranslated region (3'UTR). The Sph I restriction site 219 bp downstream of the exon M2 stop codon was destroyed by PCR based site directed mutagenesis using the oligonucleotide primers specified in Table 2. The fragment was then joined with the 5' flanking part of intron 6 by cloning via a Sph I restriction site into the immunoglobulin gamma 1 chain expression vector pIgG-A, thus leading to a complete genomically organized gamma 1 chain transcription unit. By subcloning the eukaryotic expression vector 'pmIgG-A' was constructed that codes for the secreted form (sIgG) and the membrane bound form (mIgG) of an antibody with specificity against a protein "A". The plasmid contains the following elements (see also FIG. 1A):

1. The afore mentioned transcription unit for a human gamma 1 heavy chain, composed of
   the immediate early enhancer and promoter from the human cytomegalovirus (hCMV),
   a synthetic 5' untranslated region including a Kozak consensus sequence,
   a murine immunoglobulin heavy chain signal sequence including the signal sequence intron,
   a variable heavy chain cDNA of an antibody with specificity against a protein "A",
   a mouse/human heavy chain hybrid intron 2 including the mouse Ig miu (μ) enhancer from the $J_H3$-$J_H4$ switch region (Banerji, J., et al., Cell 33 (1983) 729-740; Gillies, S. D., et al., Cell, 33 (1983) 717-728) joined with the human immunoglobulin heavy constant gamma 1 (IGHG1) gene including the exons from CH1 to M2 with all intervening introns, the polyadenylation site for the secreted form of IgG1 in intron 6, and the 3'UTR containing the polyadenylation site for the membrane bound form of IgG1.
   The genomic organization of the heavy chain constant region is depicted in FIG. 2A, the nucleotide sequence is reported in SEQ ID NO: 140. The amino acid sequences of the short (sIgG) isoform or the long (mIgG) isoform of the γ-chain constant region encoded by plasmid pmIgG-A are reported in SEQ ID NO: 141 or SEQ ID NO: 142, respectively.
2. A transcription unit for a human kappa (κ) light chain, composed of
   the immediate early enhancer and promoter from the human cytomegalovirus (hCMV),
   a synthetic 5' untranslated region including a Kozak consensus sequence,
   a murine immunoglobulin heavy chain signal sequence including the signal sequence intron,
   a variable κ chain cDNA of an antibody with specificity against a protein "A"
   the mouse intron 2 Ig κ enhancer (Emorine, L., et al., Nature 304 (1983) 447-449; Picard, D., and Schaffner, W., Nature (1984) 307, 80-82) joined with the human immunoglobulin κ constant (IGKC) gene, and
   the human IGKC gene 3'UTR containing the polyadenylation site.
3. A neomycin phosphotransferase transcription unit as a selectable marker for mammalian cells.
4. An origin of replication from the vector pUC18 for the replication of the plasmid in *E. coli*.
5. A beta(μ)-lactamase gene conferring ampicillin resistance in *E. coli*.

c) Construction of the sIgG/mIgG Expression Vectors 'pmIgGΔ-A' and 'pmIgGΔ-B'

In a similar way as described in example 1b), a 1.1 kb genomic fragment of the human immunoglobulin heavy constant gamma 3 (IGHG3) locus comprising the main part of the intron downstream of exon CH3 (intron 6), and the exon M1 was PCR amplified (for oligonucleotides see Table 2). The fragment corresponds to the nucleotides 87235195-87236300 of the "*Homo sapiens* chromosome 14 genomic contig" (NCBI accession: NT_026437, reverse complement), with a sequence identity of 98 percent. All differences are found within the intron except for one single nucleotide exchange within exon M1 that is silent, thus does not change the encoded amino acid sequence. Similarly, a 1.6 kb genomic fragment of the human immunoglobulin heavy constant gamma 4 (IGHG4) locus comprising exon M2 and the adjacent 3' untranslated region including the polyadenylation signal for the membrane bound form of the gamma 4 chain was PCR amplified (for oligonucleotides see Table 2). The fragment corresponds to the nucleotides 87087786-87089377 of the "*Homo sapiens* chromosome 14 genomic contig" (NCBI accession: NT_026437, reverse complement), with a sequence identity of 98 percent and all differences found in the 3'UTR. The Sph I site 212 bp downstream of the exon M2 stop codon was destroyed by PCR based site directed mutagenesis. Both fragments were joined between M1 and M2, amplified by PCR (for oligonucleotides see Table 2) and then cloned into the gamma 1 chain expression vector by a Sph I site in intron 6, thereby leading to a hybrid gamma 1—gamma 3—gamma 4 chain expression cassette with a genomic organization lacking the intron between M1 and M2 (intron 7). By subcloning the eukaryotic expression vector "pmIgGΔ-A" was constructed that codes for the secreted sIgG and the membrane bound mIgG form of an antibody with specificity against a protein "A". The plasmid contains the following elements (see also FIG. 1B):

1. The aforementioned transcription unit for a hybrid gamma 1—gamma 3—gamma 4 heavy chain, composed of
   the immediate early enhancer and promoter from the human cytomegalovirus (hCMV),
   a synthetic 5' untranslated region including a Kozak consensus sequence,
   a murine immunoglobulin heavy chain signal sequence including the signal sequence intron,
   a variable heavy chain cDNA of an antibody with specificity against a protein "A",
   a mouse/human heavy chain hybrid intron 2 including the mouse Ig μ enhancer ($J_H3$-$J_H4$ switch region) joined with the human IGHG1 gene including the exons from CH1 to $C_H3$ with all intervening introns, and the adjacent 5' part of intron 6 including the polyadenylation site for the secreted form of the immunoglobulin,
   the 3' part of intron 6 and exon M1 from the human IGHG3 gene, and
   the exon M2 and the 3' untranslated region containing the polyadenylation site for the membrane bound form of the immunoglobulin from the human IGHG4 gene.
   The genomic organization of the heavy chain constant region is depicted in FIG. 2B, the nucleotide sequence is reported in SEQ ID NO: 143. The amino acid sequences of the short (sIgG) isoform or the long (mIgG) isoform of the γ-chain constant region encoded by plasmid pmIgGΔ-A are reported in SEQ ID NO: 144 or SEQ ID NO: 145, respectively.

2. A transcription unit for a human kappa light chain, composed of
    the immediate early enhancer and promoter from the human cytomegalovirus (hCMV),
    a synthetic 5'UTR including a Kozak consensus sequence,
    a murine immunoglobulin heavy chain signal sequence including the signal sequence intron,
    a variable κ chain cDNA of an antibody with specificity against a protein "A"
    the mouse intron 2 Ig κ enhancer joined with the human immunoglobulin κ constant (IGKC) gene, and
    the human IGKC gene 3' untranslated region containing the polyadenylation site.
3. A neomycin phosphotransferase transcription unit as a selectable marker for mammalian cells.
4. An origin of replication from the vector pUC18 for the replication of the plasmid in E. coli.
5. A beta-lactamase gene conferring ampicillin resistance in E. coli.

By exchange of the cDNA sequences coding for the variable regions of the gamma and the kappa chain the sIgG/mIgG expression vector 'pmIgGΔ-B' was constructed. It has the same organization as described for pmIgGΔ-A above but codes for an immunoglobulin with specificity against a protein "B" instead.

Example 2

Transfection and Analysis of Sp2/0-Ag14 Cells
a) Cultivation and Electroporation of Sp2/0-Ag14 Cells
    Sp2/0-Ag14 hybridoma cells (ATCC No. CRL-1581, Shulman, M., et al., Nature 276 (1978) 269-270) are cultivated in RPMI medium (Invitrogen Corp., US) supplemented with 10% ultra-low IgG fetal calf serum (FCS) (Invitrogen Corp., US) and 2 mM glutamine (Invitrogen Corp., US) at 37° C., 5% $CO_2$ and 95% humidity. For transfection the cells are electroporated with 10 µg plasmid DNA per $10^6$ cells in 20 mM HEPES-buffer (N-(2-hydroxyethyl)-piperazine-N'-2-ethanesulfonic acid), pH 7.0 containing 137 mM NaCl, 5 mM KCl, 0.7 mM $Na_2HPO_4$, and 6 mM Glucose at 4° C. The electroporation is performed at 220 V and 960 µF with a Genepulser electroporation device (Bio-Rad Laboratories Inc., US). After the transfection the cells are distributed to 96 well plates with 5000 cells in 100 µl medium per well. For the selection of transfected cells 500 µg/ml G418 (Roche Diagnostics GmbH, Germany) is added to the medium one day after the electroporation. The medium is changed every two to three days to maintain the selection pressure. About two weeks after the transfection transfectoma clones are isolated from the 96 well plates and further propagated in appropriate culture vessels. For storage about $10^6$ cells of a clone are frozen in 10% dimethylsulfoxide (Sigma-Aldrich Co., Germany) in low IgG FCS (Invitrogen Corp., US) and stored in liquid nitrogen.

The transfections of each $10^6$ cells with the plasmids pmIgG-A, pmIgGΔ-A and pIgG-A led to 15, 19 and 12 independent clones, respectively. From each transfection 6 clones were randomly selected for further analysis.

b) IgG Quantification and Analysis by Flow Cytometry
    $10^5$ cells of each clone of Example 2a) were seeded in 2 ml medium containing G418 (as described above) in 6 well plates and cultivated for 48 hours. Thereafter the supernatants were collected and the amount of secreted IgG was quantified by Homogeneous Time-Resolved Fluorescence (HTRF) immunoassay using the 'Human Fc detection kit' (CIS bio international) according to the manufacturer's protocol. To analyze the plasma-membrane-bound antibodies by flow cytometry, $10^5$ cells of each clone were washed two times with PBS (phosphate buffered saline) at 4° C., then resuspended in 50 µl FITC-conjugated F(ab')$_2$ fragment mouse anti-human IgG (Dianova, Germany), diluted 1:50 in PBS containing 1% BSA (Roche Diagnostics GmbH, Germany), and incubated for one hour at 4° C. in the dark. After washing two times with PBS, the cells were resuspended in PBS and analyzed with a BD FACSCalibur flow cytometer (BD Biosciences, US). As a measure of the amount of IgG bound to the cell surface the median fluorescence intensity was determined for each clone.

Figure 3:
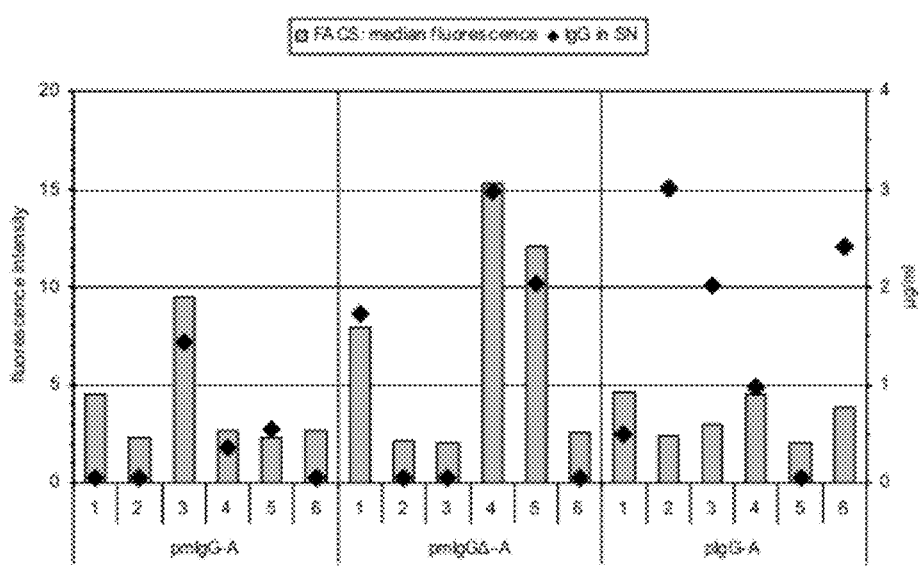
FIG. 3: Correlation of IgG secretion and cell surface signal in clones expressing mIgG. Six independent clones of Sp2/0-Ag14 cells transfected with the plasmid pmIgG-A (left), pmIgGΔ-A (middle), or pIgG-A (control (right) are cultivated for 48 hours under defined conditions. The median fluorescence intensity in flow cytometry as a measure of the amount of IgG bound to the plasma membrane is represented by grey bars. The concentration of secreted IgG in the corresponding cell culture supernatants is represented by black diamonds.

In FIG. 3 the median fluorescence intensity in flow cytometry is displayed together with the IgG concentration in the cell culture supernatant for each clone. It was observed that for clones transfected with pmIgG-A or pmIgGΔ-A (i.e. plasmids coding for both the sIgG and the mIgG form) an increased amount of secreted IgG corresponds with an elevated cell surface signal. Such a correlation was not observed for clones transfected with pIgG-A (i.e. the plasmid coding for only sIgG, the secreted form of the antibody).

Example 3

Figure 4:
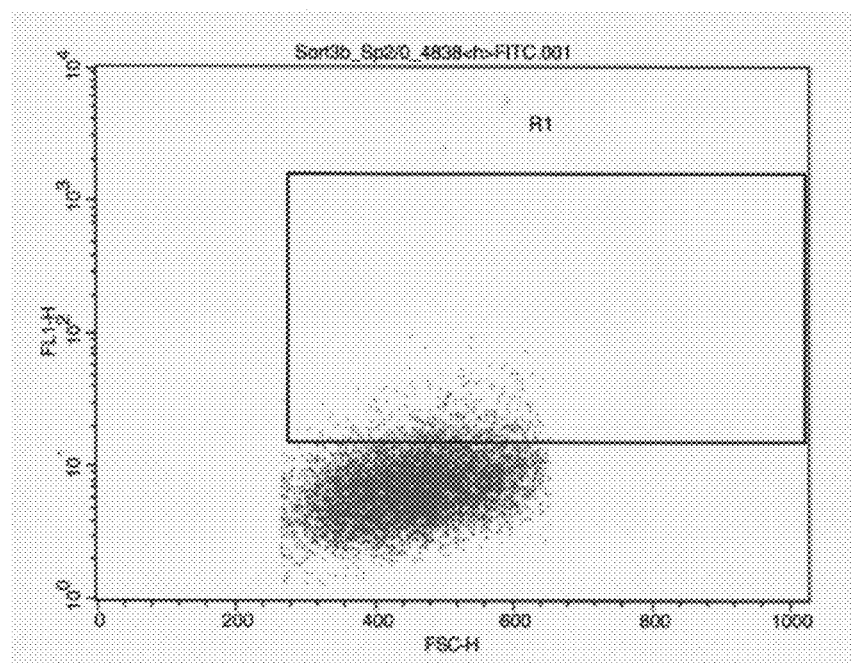
FIG. 4: Typical FL1/FSC dot plot used for sorting of cells on a FACS Vantage flow cytometer (BD). The gate R1 comprises 5.7% of the depicted live cell population that has been gated by a FSC/SSC dot plot before. Cells falling into R1 were collected during sorting process.

Sorting of Stably Transfected Cells by Flow Cytometry
    For the generation of clones stably expressing IgG $3\times10^6$ Sp2/0-Ag14 cells were transfected with the plasmid pmIgGΔ-B by electroporation as described above. One day after the transfection the cells were transferred to 500 µg/ml G418 selection medium and cultivated as pool for about two weeks. After the selection the IgG bound to the surface of the transfected cells was labeled and cells with the most intense signals were sorted by flow cytometry. Therefore $4\times10^6$ cells from the pool were washed two times with medium at 4° C. then incubated with fluorescein (FITC)-conjugated F(ab')$_2$ fragment mouse anti-human IgG (Dianova, Germany), 1:50 diluted in medium, for 20 minutes on ice. After two washing steps with medium the cells were resuspended in medium and transferred to a BD FACSVantage flow cytometer (BD Biosciences, US). A gate was set encompassing cells with the top 5-6% of fluorescence intensity of the sample population (FIG. 4), and cells sorted by this gate were collected. The collected cells were expanded by cultivation in selection medium for several days. With these cells a second and, consecutively, a third sorting cycle was performed as described above. Instead of collecting the sorted cells as pool, a fourth and final sorting step was used for single cell depositions into 96 well plates. The deposition led to 141 independent clones from which 21 were selected for IgG expression analysis by HTRF immunoassay as described in example 2b). Two clones out of these, 5B11 and 9B3, that showed the highest IgG secretion rates and, correspondingly, the strongest cell surface signals, were adapted to serum free growth in spinner culture for further assessment of their productivity.

Example 4

Determination of the Specific Productivity of Clones
    For the determination of their specific productivity, the clones 5B11 and 9B3 were cultivated under defined conditions in ProCHO 6k medium (Cambrex Corp., US), supplemented with 1× Colesterol/Lipid concentrate (Invitrogen Corp., US), 4 mM Glutamine (Invitrogen Corp., US) and 250 µg/ml G418 (Roche Diagnostics GmbH, Germany), in 100 ml spinner flasks (Belco, US.). The cells were grown at 37° C., 5% $CO_2$ and 95% humidity until they reached a stationary growth phase. At several time points during the exponential growth phase the cell count of every clone was determined with a CASY cell counter (Scharfe Systems, Germany) and the IgG concentration in the supernatants were determined by protein A affinity chromatography (see below). As reference, the clone J5-H3 was cultivated and analyzed under equal conditions. This clone was also derived from transfection of Sp2/0-Ag14 cells and stably expresses the identical antibody as the clones 5B11 and 9B3, albeit the secreted form only. Clone J5-H3 was generated conventionally by several limiting dilution and subcloning steps and has been selected out of more than 1000 clones to fulfill the productivity requirements for an industrial manufacturing process.

The IgG concentrations in cell culture supernatants were determined by analytical affinity chromatography using an Äkta™ explorer chromatography unit (GE Healthcare, former Amersham Biosciences, Sweden). A defined volume of a cell culture supernatant was applied to a protein A sepharose column to facilitate binding of IgG to the affinity matrix. The column was washed with 100 mM citric acid pH 5.0, and then bound antibodies were eluted with 100 mM citric acid pH 3.0. The elution was monitored by continuous recording of the UV absorption of the eluate at 280 nm. The antibody concentration of a sample was calculated from the integrated UV absorption after calibration of the system with standard samples containing defined antibody concentrations.

For every clone specific production rates (SPRs) were calculated from the cell counts and the IgG concentrations in cell culture supernatants by the following equation:

$$SPR = \frac{\Delta c(IgG)}{\overline{c(\text{cells})} \cdot \Delta t} \left[ \frac{pg}{\text{cell} \cdot \text{day}} \right],$$

wherein
"$\Delta c(IgG)$" being the difference of the IgG concentration in the supernatant between beginning and end of the time interval in [pg/ml],
"$\overline{c(\text{cells})}$" being the arithmetic average of the cell count of the beginning and the end of the time interval in [cells/ml], and
"$\Delta t$" being the length of the time interval in [days].

Figure 5:
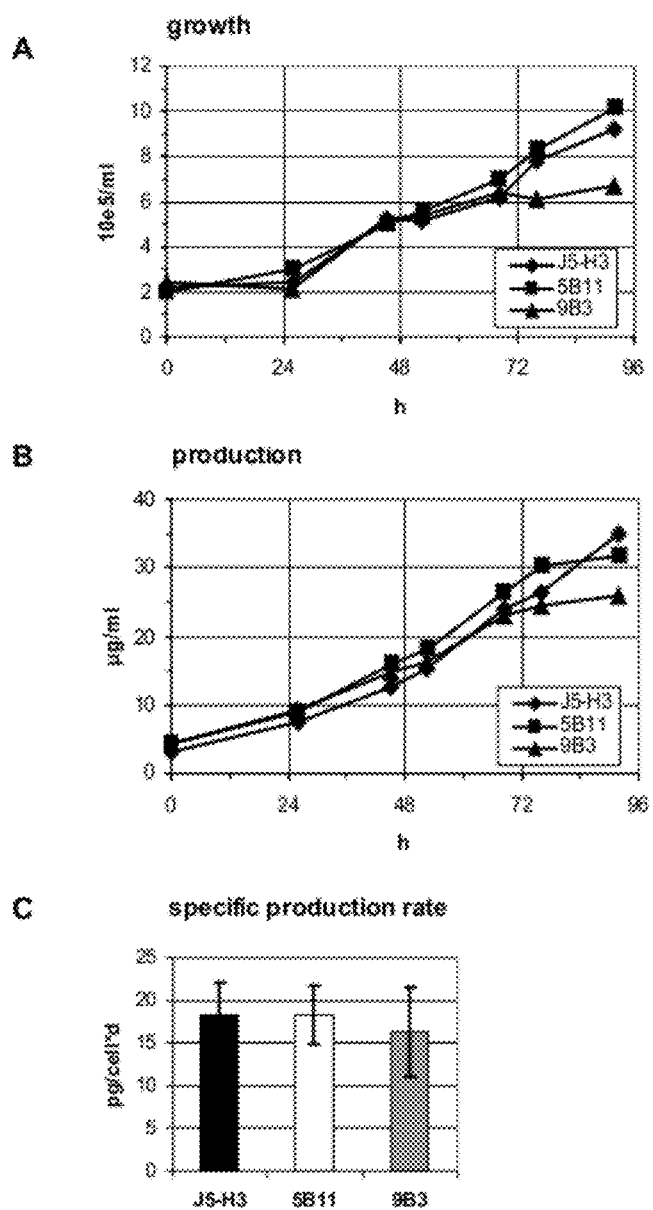
FIG. 5: Determination of specific production rates. The clones 5B11, B3 and J5-H3 were cultivated in spinner flasks for 92 hours.
  A: Cell growth. At the indicated time points after starting the spinner cultures the cell count of each clone was measured with a CASY cell counter.
  B: IgG production. At the indicated time points (as in A) the IgG concentrations in the cell culture supernatants were determined by protein A affinity chromatography.
  C: Specific production rates. The bar chart shows the average specific production rate for each clone calculated from the cell counts and IgG measurements within the first 69 hours (see Table 2 and see text for further details). The standard deviations are indicated by error bars.

An average SPR was determined for every clone based on four distinct SPRs calculated at several time points during the exponential growth phase (FIG. 5 and Table 5).

TABLE 5

Determination of specific production rates (SPR).

| Clone | expressed IgG form | time interval [h] | SPR [pg · cell$^{-1}$ · d$^{-1}$] | average SPR ± SD [pg · cell$^{-1}$ · d$^{-1}$] |
|---|---|---|---|---|
| 5B11 | sIgG, mIgG | 0-26.2 | 16.9 | 18.3 ± 3.4 |
|  |  | 26.2-45.3 | 22.3 |  |
|  |  | 45.3-52.7 | 14.3 |  |
|  |  | 52.7-68.5 | 19.6 |  |
| 9B3 | sIgG, mIgG | 0-25.7 | 19.9 | 16.3 ± 5.3 |
|  |  | 25.7-45 | 19.3 |  |
|  |  | 45-52.4 | 8.5 |  |
|  |  | 52.4-68.3 | 17.4 |  |
| J5-H3 | sIgG | 0-26 | 16.7 | 18.4 ± 3.7 |
|  |  | 26-45.2 | 17.3 |  |
|  |  | 45.2-52.6 | 15.6 |  |
|  |  | 52.6-68.4 | 23.8 |  |

Both clones sorted by membrane bound mIgG, 5B11 and 9B3, exhibited average SPRs between 15 and 20 pg·cell$^{-1}$·d$^{-1}$, which is in a range that is suitable for manufacturing clones in an industrial scale. The SPRs of these clones are comparable to an SPR that can be achieved with a clone obtained by a laborious conventional strategy in the same cell line and expressing the same antibody (clone J5-H3).

Example 5

Detection of sIgG and mIgG by Immunofluorescence Microscopy

Intracellular and cell surface bound antibodies were detected by immunofluorescence microscopy. For intracellular staining cells attached to poly-L-lysine-coated microscopy slides were fixed with 2% (v/v) formaldehyde in PBS for 10 minutes, permeabilized with 0.2% (v/v) Triton X-100 in PBS for 10 minutes and washed twice with PBS. Unspecific binding sites were blocked with 3% (w/v) BSA (bovine serum albumin) in PBS for 30 min. The cells were washed twice with washing buffer (WB: 0.2% (w/v) BSA, 0.1% (v/v) Tween 20 in PBS), then incubated with R-Phycoerythrin-conjugated F(ab')$_2$ fragment goat anti-human IgG (Dianova, Germany), 1:50 diluted in WB, for one hour. After washing four times with WB and twice with doubly deionized H$_2$O, the cells were mounted under a coverslip and stored at 4° C. in the dark until microscopy. For staining of cell surface bound antibodies 10$^5$ cells were washed with cold 1% (w/v) BSA in PBS, then unspecific binding sites were blocked with 1% BSA in PBS on ice for 30 minutes. For IgG labeling the cells were incubated with R-Phycoerythrin-conjugated F(ab')$_2$ fragment goat anti-human IgG (Dianova, Germany), 1:50 diluted in 1% (w/v) BSA in PBS, for one hour on ice. After washing three times with cold PBS the cells were attached to poly-L-lysine-coated microscopy slides and fixed with 2% (v/v) formaldehyde in PBS for 10 minutes at room temperature. After washing twice with PBS the cells were mounted under a coverslip and stored at 4° C. in the dark until microscopy. Intracellular and surface labeled cells were analyzed on an Axiophot fluorescence microscope using a Plan-APOCHROMAT 40×/1.0 objective (Carl Zeiss, Germany).

Figure 6:
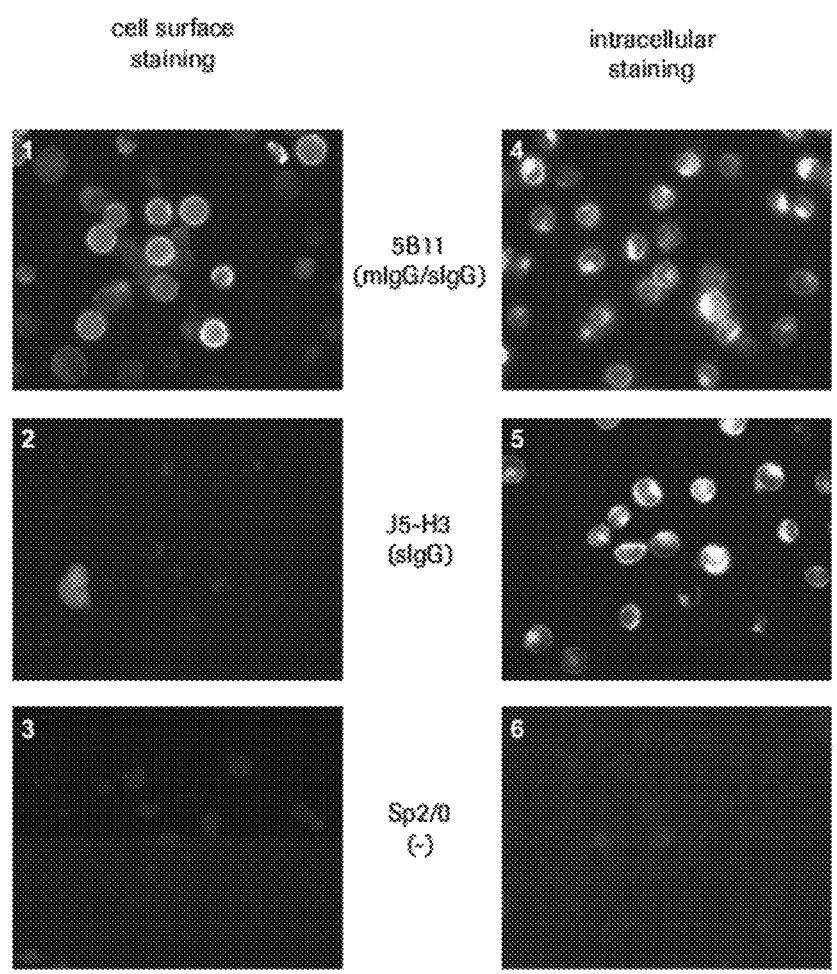
FIG. 6: Immunofluorescence microscopy. The clone 5B11 (images 1, 4), expressing secreted sIgG and membrane bound mIgG, the clone J5-H3 (images 2, 5), expressing secreted sIgG only, or untransfected Sp2/0-Ag14 cells (images 3, 6), were labeled for IgG on the cell surface (images 1-3), or intracellular IgG (images 4-6), and images recorded at an Axiophot fluorescence microscope.

In the clone 5B11 antibodies can be detected on the cell surface (FIG. 6, image 1), which is mainly the mIgG form, as well as intracellular (image 4), which are both IgG forms on the expression/secretion pathways. In contrast, in the clone J5-H3 only intracellular antibodies can be detected (FIG. 6, images 2 and 5), as this clones does not express mIgG. No staining with both methods is observed in the untransfected cell line Sp2/0-Ag14 (FIG. 6, images 3 and 6), since these cells express no IgG at all.

Example 6

Detection of γ-Chain mRNA Isoforms by Northern Blotting

Figure 7:
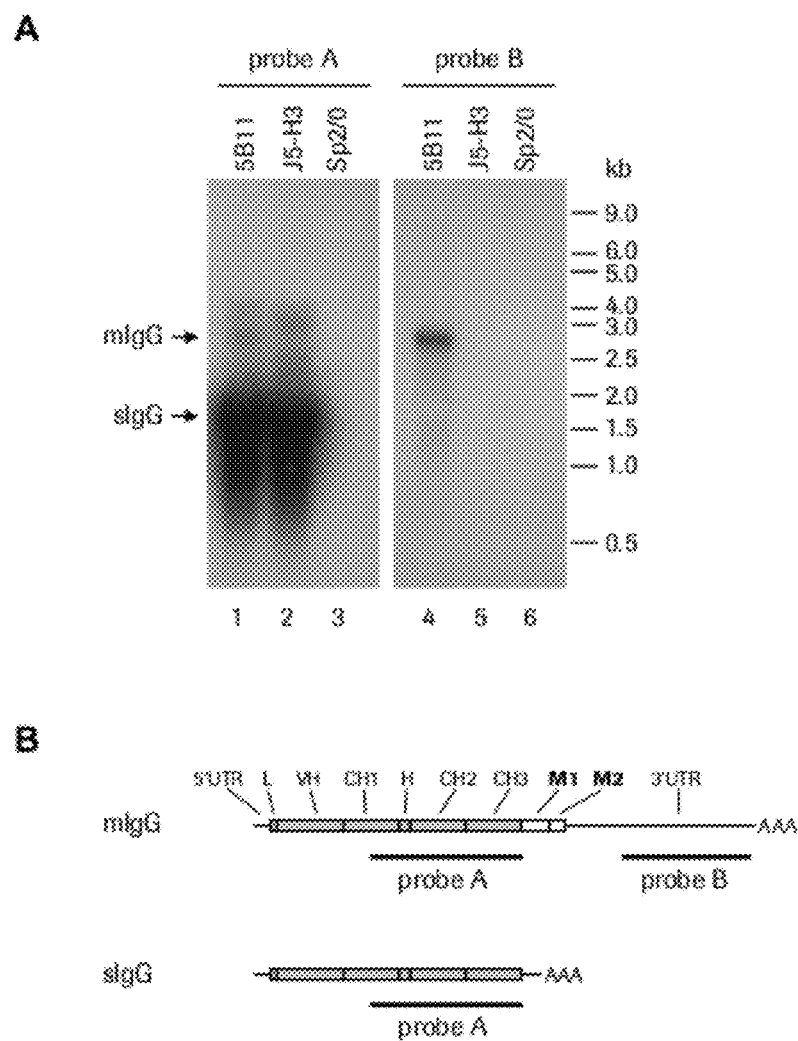
FIG. 7: Analysis of mRNA by Northern blot.
  A: Autoradiography of a Northern blot hybridized with [α-$^{32}$P] labeled probe A (lanes 1-3) or probe B (lanes 4-6). In each lane 10 μg total RNA isolated from clone 5B11 (lanes 1, 4), clone J5-H3 (lanes 2, 5) or untransfected Sp2/0-Ag14 cells (lanes 3, 6), was separated by denaturating agarose gel electrophoresis and transferred to a nylon membrane.
  B: Schematic depiction of the two mRNA isoforms encoding the heavy chain of membrane bound mIgG or secreted sIgG. The exons are represented by boxes. The regions complementary to the probes A and B are marked with black bars.

To define the ratio between the two heavy chain isoforms that emerge by alternative splicing/polyadenylation of the primary transcript, RNA of stably transfected clones was analyzed by Northern blot. Therefore total RNA was isolated from cells using the RNeasy technology (Qiagen, Germany). In each case 10 µg of total RNA were then fractionated by denaturating agarose gel electrophoresis and transferred to a nylon membrane using the NorthernMax System (Ambion Inc., US). For hybridization of the blot membrane two different DNA probes were marked with [alpha-$^{32}$P] by the random priming method using the DECAprime II kit (Ambion Inc. US). As depicted in FIG. 7B, probe 'A' is complementary to the heavy chain mRNA between exon CH1 and CH3 and thus hybridizes to both isoforms. In contrast, probe 'B' only binds to the 3'UTR of the long mIgG heavy chain mRNA. After hybridization and stringent washing of the membrane the blot was analyzed by autoradiography.

FIG. 7A represents an autoradiography of a Northern blot with total RNA from clone 5B11, clone J5-H3 and the cell line Sp2/0-Ag14. The hybridization with probe 'A' shows a predominant 1.8 kb signal in both antibody expressing clones (lanes 1 and 2), which corresponds to the expected size of the short mRNA isoform that encodes the heavy chain of the sIgG. In the depicted long exposure also some weak signals between 2 and 4 kb are detected. The 3.3 kb band, which is only seen in clone 5B11 (lane 1), represents the long mRNA isoform that encodes the heavy chain of the mIgG, since a band with the same migration pattern is detected as single signal when the blot is hybridized with probe 'B' (lane 4). The comparison of the relative signal strengths of the 1.8 kb and the 3.3 kb band in lane 1 suggests that the primary transcript of the antibody heavy chain transgene is predominantly processed to the small mRNA isoform, giving rise to the secreted sIgG form of the antibody. Only a minor amount (less than 5%) is completely spliced to the long mRNA isoform, thus leading to plasma-membrane-bound mIgG.

Example 7

Purification and Detection of IgG Heavy Chain Isoforms by Alkaline Carbonate Extraction and Immunoblotting To detect the mIgG heavy chain, membrane proteins were extracted from stably transfected cells using the alkaline carbonate extraction method developed by Fujiki (Fujiki, Y., et al., J. Cell Biol. 93 (1982) 97-102). In each case 10$^7$ cells were washed twice with PBS, then once with 0.1 M NaCl on ice. After resuspension in 1 ml cold 0.1 M Na$_2$CO$_3$ pH 11.5 the cells were disrupted by sonification for 20 seconds, incubated on ice for 30 minutes and then centrifuged for 60 minutes with 200,000×g at 4° C. By this step cellular membranes still containing integral membrane proteins are separated from soluble contents. The supernatants were collected and it was added Triton X-100 to a final concentration of 1% (w/v), N-octyl-beta-D-glucopyranoside to a final concentration of 60 mM, TRIS-HCl pH 7.4 to a final concentration of 50 mM and NaCl to a final concentration of 300 mM ("SN fraction"). Accordingly, the membrane pellets were resolved in 1.1 ml 0.1 M Na$_2$CO$_3$ pH 11.5, 1% (w/v) Triton X-100, 60 mM N-octyl-beta-D-glucopyranoside, 50 mM TRIS-HCl pH 7.4 and 300 mM NaCl. Insoluble components after that step were removed by centrifugation for 10 minutes at 15,000×g and the supernatants collected as "membrane fraction". Protein A pull down assays were performed to purify the antibody isoforms from the membrane or SN fractions. Therefore each fraction was incubated with 30 µl bed volume Protein A sepharose (GE Healthcare formerly Amersham Biosciences, Sweden) for 60 minutes at 4° C., then washed four times with PBS containing 0.02% (v/v) Igepal CA360. Proteins bound to the protein A matrix were eluted with reducing protein gel sample buffer at 70° C. and separated by SDS polyacrylamide gel electrophoresis (NuPAGE®-system, Invitrogen Corp., US). After the separation the proteins were transferred to a PVDF (polyvinylidenfluoride) membrane according to the semidry immunoblotting method (Ausubel, F. A., et al. (eds.) Current Protocols in Molecular Biology, Vol. 2, John Wiley and Sons, Inc., New York (1995)). IgG heavy chains immobilized on the membrane were labeled with polyclonal rabbit anti-human IgG antibodies coupled to horseradish peroxidase (DakoCytomation, DAKO A/S, Denmark) and detected by chemiluminescence reaction (LUMI-Light PLUS Western Blotting Kit, Roche Diagnostics GmbH) on a LUMI-Imager F1 (Roche Diagnostics GmbH).

Figure 8:
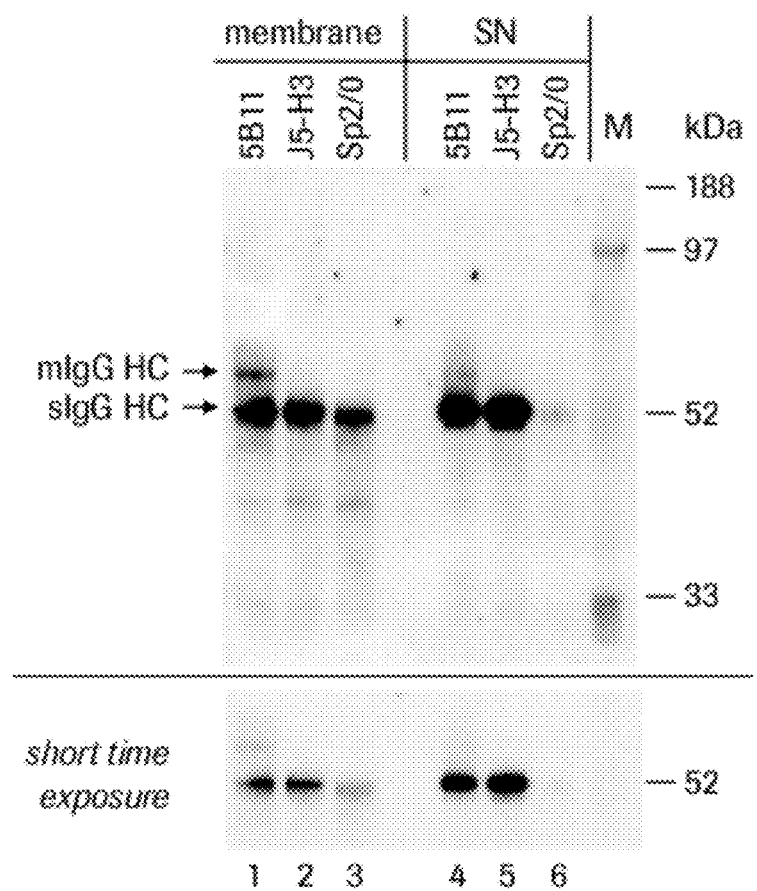
FIG. 8: Immunoblot analysis of IgG heavy chain isoforms. The clones 5B11 (lanes 1, 4), J5-H3 (lanes 2, 5) or untransfected Sp2/0-Ag14 cells (lanes 3, 6) were extracted according to the alkaline carbonate extraction method (see text). Immunoglobulins from the membrane fractions, that contain integral membrane proteins (lanes 1-3), or from the SN fractions, that predominantly contain soluble contents of the cells (lanes 4-6), were purified by protein A pull down assay and separated by denaturating SDS polyacrylamide gel electrophoresis. After blotting and labeling with a horseradish peroxidase-coupled secondary antibody the heavy chains were visualized by a chemiluminescence reaction. Secreted sIgG heavy chains (sIgG HC) and membrane bound mIgG heavy chains (mIgG HC) are indicated. The lower panel shows a short time exposure of a section of the blot in the upper panel.

A strong signal according to the heavy chain of sIgG could be detected in the membrane and SN fraction of both clones expressing antibodies (clones 5B11 and J5-H3, see FIG. 8, lanes 1, 2, 4 and 5). In the case of clone 5B11 an additional protein is detected which migrates above the sIgG heavy chain (FIG. 8, lane 1). This band is predominantly found in the membrane fraction of this clone in which the integral membrane proteins are enriched. It represents the larger mIgG heavy chain isoform, which has a calculated molecular weight 8 kDa higher than the sIgG heavy chain. Consistently there is no corresponding signal in clone J5-H3 (FIG. 8, lane 2) as this clone solely expresses the secreted form of the antibody.

Example 8

Cultivation and Transfection of CHO-K1 Cells.

CHO-K1 cells (ATCC No. CCL-61; Puck, T. T., et al., J. Exp. Med. 108 (1958), 945-956), that have been pre-adapted to serum-free growth in suspension culture, were cultivated in ProCHO4-CDM medium (Cambrex Corp., US), supplemented with 8 mM L-Alanyl-L-glutamine (Invitrogen Corp., US) and 1× HT supplement (Invitrogen Corp., US), at 37° C., 5% CO$_2$ and 95% humidity in suspension flasks. Every 3-4 days the cells are splitted with 2×10$^5$ cells/ml into fresh medium. For transfection, the cells are electroporated with 20 µg plasmid DNA per 7.5×10$^6$ cells in a total volume of 200 µl PBS at room temperature. The electroporations are performed with a Gene Pulser XCell electroporation device (Bio-Rad Laboratories, US) in a 2 mm gap cuvette, using a square wave protocol with a single 160 V pulse for 15 ms. For the generation of clones stably expressing IgG, 6×10$^7$ cells were electroporated with the plasmid pmIgGΔ-B as described. Afterwards the cells were cultivated as pool in the medium specified above for about two weeks with 700 µg/ml G418 (Roche Diagnostics GmbH, Germany) added to the culture one day after the transfection for selection of stably transfected cells.

Example 9

Sorting of Stably Transfected CHO-K1 Cells by Flow Cytometry

After the selection the IgG bound to the surface of the transfected cells was labeled and cells with the most intense signals were sorted by flow cytometry. Therefore 4×10$^7$ cells from the pool were first passed through a 40 µM nylon mesh to remove large cell aggregates and then incubated with Accumax (PAA) for 15 minutes at 37° C. to separate remaining smaller aggregates. The cells were incubated in 1% (w/v) BSA in medium (see example 8) for 20 minutes on ice, then stained with 10 ng/ml Protein A Alexa Fluor 488 (Molecular Probes Inc., Invitrogen Corp., US), in a total volume of 8 ml medium with 1% (w/v) BSA in for 30 minutes on ice in the dark. After two washing steps with 1% (w/v) BSA in medium the cells were resuspended in medium and transferred to a BD FACSAria cell sorter (BD Biosciences, US). The population of live single cells was gated by a forward-scatter/side-scatter (FSC/SSC) dot plot. A subpopulation was defined encompassing the cells with the top 5% of fluorescence intensity of the gated live cells, and about 45,000 cells from this subpopulation were collected (mIgG-sorted cell pool). As control about 40,000 cells were collected randomly from the FSC/SSC-gated live cell population regardless of their fluorescence (control cell pool). The collected cell pools were expanded by cultivation in selection medium (see example 8) for two weeks. A second sorting cycle was then performed. The cells from the mIgG-sorted cell pool were stained for cell surface IgG as described above. Using a BD FACSAria cell sorter (BD Biosciences, US) the cells with the top 4% of fluorescence intensity were sorted from the population of live single cells (gated by FSC/SSC dot plot). The sorted cells were collected as single cells into 96 well plates. From the control cell pool single cells were collected randomly from the FSC/SSC-gated, unstained live cell population. Single cell clones were expanded by cultivation in selection medium (see example 8) for three weeks.

Example 10

Determination of IgG Concentrations by ELISA

The immunoglobulin concentration in cell culture supernatants was determined by a sandwich ELISA which used a biotinylated anti-human IgG F(ab')2 fragment as the capture reagent and for detection a peroxidase-conjugated anti-human IgG F(ab')$_2$ antibody fragment.

Streptavidin coated 96 well plates (Pierce Reacti-Bind™ Streptavidin Coated Polystyrene Strip Plates, Code No. 15121) were coated with 0.5 µg/ml biotinylated goat polyclonal anti-human IgG F(ab')2 antibody fragment (F(ab')2<h-Fcγ>Bi; Dianova, Germany, Code No. 109-066-098) capture antibody (0.1 ml/well) in diluent buffer (diluent buffer: PBS buffer containing 0.5% weight by volume (w/v) bovine serum albumin) by incubation for one hour at room temperature (RT) under shaking. Thereafter, the plates were washed three times with more than 0.3 ml wash buffer (wash buffer: PBS containing 1% (w/v) Tween 20). IgG containing cell culture supernatants (samples) were diluted serially (twofold) up to a concentration of 0.5-20 ng/ml in diluent buffer, added to the wells and incubated for one hour at RT with shaking. Purified standard antibody (0.5-20 ng/ml) in diluent buffer was used for the generation of an IgG protein standard curve. After washing the plates three times with 0.3 ml/well wash buffer, bound complexes to anti-human Fcγ were detected with a peroxidase-conjugated F(ab')2 fragment of goat polyclonal anti-human F(ab')2-specific IgG (F(ab')2<h-Fcγ>POD; Dianova, Germany, Code No. 109-036-098). After washing the plates three times with 0.3 ml/well wash buffer the plates were developed with ABTS® (2,2'-azino-bis(3-ethylbenzthiazoline-6-sulfonic acid) peroxidase substrate solution (Roche Diagnostics GmbH, Germany, Code No. 1684302). After 10-30 minutes the absorbance was measured at 405 nm and 490 nm against a reagent blank (incubation buffer+ABTS solution) on a Tecan Spectrafluorplus plate reader (Tecan Deutschland GmbH, Germany). For background correction the absorbance at 490 nm was subtracted from the absorbance at 405 nm according to the following formula:

$$\Delta A = (A_{sample}^{405nm} - A_{sample}^{490nm}) - (A_{blank}^{405nm} - A_{blank}^{490nm})$$

The IgG content of the samples were calculated from the standard curve.

Example 11

Screening and Selection of mIgG Expressing CHO Clones

Three weeks after single cell depositions into 96 well plates, cell culture supernatants of 515 mIgG-sorted clones, and of 550 control clones were analyzed by ELISA (see example 10). Table 6 shows the distribution of clones to different IgG concentration levels.

TABLE 6

Screening of 96 well plate deposited clones by ELISA.

| IgG in SN | mIgG-sorted clones | | control clones | |
|---|---|---|---|---|
| [µg/ml] | # clones | % clones | # clones | % clones |
| ≦1 | 0 | 0 | 495 | 90.0 |
| ≦2 | 65 | 12.6 | 44 | 8.0 |
| ≦3 | 76 | 14.8 | 5 | 0.9 |
| ≦4 | 67 | 13.0 | 2 | 0.4 |

TABLE 6-continued

Screening of 96 well plate deposited clones by ELISA.

| IgG in SN | mIgG-sorted clones | | control clones | |
|---|---|---|---|---|
| [µg/ml] | # clones | % clones | # clones | % clones |
| ≦5 | 66 | 12.8 | 0 | 0 |
| ≦6 | 58 | 11.3 | 1 | 0.2 |
| ≦7 | 35 | 6.8 | 0 | 0 |
| ≦8 | 39 | 7.5 | 0 | 0 |
| ≦9 | 32 | 6.2 | 1 | 0.1 |
| ≦10 | 21 | 4.1 | 0 | 0 |
| ≦11 | 16 | 3.1 | 0 | 0 |
| ≦12 | 9 | 1.8 | 1 | 0.2 |
| ≦13 | 6 | 1.1 | 1 | 0.2 |
| ≦14 | 4 | 0.8 | | |
| ≦15 | 3 | 0.6 | | |
| ≦16 | 2 | 0.4 | | |
| ≦17 | 3 | 0.6 | | |
| ≦18 | 2 | 0.4 | | |
| ≦19 | 1 | 0.2 | | |
| ≦20 | 2 | 0.3 | | |
| ≦21 | 1 | 0.2 | | |
| ≦22 | 1 | 0.2 | | |
| >22 | 6 | 1.2 | | |

It was observed that in the control approach 90 percent of all clones showed an IgG concentration of 1 µg/ml and below. In contrast, no mIgG-sorted clone fell into this group. Moreover in this approach IgG concentrations of greater than 22 µg/ml were reached by 6 clones, whereas the highest IgG-concentration measured in the control approach was 12.3 µg/ml. All mIgG-sorted clones with more than 10 µg/ml and all control clones with more than 3 µg/ml were then transferred to 24 well plates for a second screening. The clones were outgrown by cultivation in selection medium (see example 8) for 20 days, then the IgG concentrations in the cell culture supernatants were determined by ELISA. Table 7 shows the distribution of clones to different IgG concentration levels.

TABLE 7

Screening of 24 well deposited clones by ELISA.

| IgG in SN | mIgG-sorted clones | | control clones | |
|---|---|---|---|---|
| [µg/ml] | # clones | % clones | # clones | % clones |
| ≦5 | 2 | 3.7 | 3 | 50.0 |
| ≦10 | 1 | 1.9 | 1 | 16.7 |
| ≦15 | 2 | 3.7 | 1 | 16.6 |
| ≦20 | 1 | 1.8 | 1 | 16.7 |
| ≦25 | 5 | 9.3 | | |
| ≦30 | 12 | 22.2 | | |
| ≦35 | 13 | 24.1 | | |
| ≦40 | 7 | 12.9 | | |
| ≦45 | 5 | 9.3 | | |
| ≦50 | 4 | 7.4 | | |
| ≦55 | 1 | 1.8 | | |
| ≦60 | 1 | 1.9 | | |
| average IgG conc. (µg/ml) | 31.4 | | 6.1 | |

The control clones displayed expression levels up to 16.8 µg/ml with an average IgG concentration of 6.1 µg/ml. In contrast, the average expression of the mIgG-sorted clones was 31.4 µg/ml, with 58.9 µg/ml being the highest observed IgG concentration of one clone in this group. The six mIgG-sorted clones with more than 45 µg/ml and the two control clones with more than 10 µg/ml were then transferred to 125 ml shaker flasks for further assessment.

Example 12

Productivity Assessment of Selected CHO Clones

For adaptation to shaking the selected clones of Example 11 were transferred to 125 ml shaker flasks, and cultivated in 25 ml selection medium (see example 8) for one week on a gyratory shaker with 150 rpm under standard conditions (see example 8). Thereafter, for each clone 25 ml ProCHO5-CDM medium (Cambrex Corp., US), supplemented with 8 mM L-Alanyl-L-glutamine (Invitrogen Corp., US), 1×HT supplement (Invitrogen Corp., US) and 400 µg/ml G418 (Roche Diagnostics GmbH, Germany) was inoculated with 1×10$^6$ cells/ml and cultivated in 125 ml shaker flasks as described before. On day 0, 1, 2, 3, 4, and 7 the cell count of every clone was determined with a CASY® TT cell counter (Scharfe Systems, Germany), indicating a comparable growth of all tested clones (see Table 8).

TABLE 8

Cell count of shaker cultures.

| clone | cell count [10$^6$/ml] | | | | | |
|---|---|---|---|---|---|---|
| | day 0 | day 1 | day 2 | day 3 | day 4 | day 7 |
| mIgG-sorted clones | | | | | | |
| 1A1 | 1.10 | 1.15 | 4.30 | 5.57 | 7.46 | 9.96 |
| 1B6 | 1.10 | 1.22 | 4.12 | 5.60 | 6.58 | 8.76 |
| 1C5 | 0.99 | 1.81 | 5.59 | 5.53 | 6.06 | 5.76 |
| 1D1 | 0.99 | 1.58 | 3.08 | 5.77 | 5.39 | 5.40 |
| 1D6 | 1.11 | 1.31 | 5.06 | 5.70 | 6.60 | 8.36 |
| 2D6 | 1.09 | 1.42 | 3.37 | 5.32 | 5.42 | 5.12 |
| control clones | | | | | | |
| KO2 | 1.07 | 1.42 | 3.23 | 4.94 | 5.06 | 7.12 |
| KO6 | 1.03 | 1.55 | 5.89 | 5.56 | 7.44 | 8.00 |

On day 10 the cell culture supernatants were collected and IgG concentrations were determined by ELISA (see Table 9).

TABLE 9

Productivity determination of 10 day shaker cultures by ELISA.

| clone | IgG in SN [µg/ml] |
|---|---|
| mIgG-sorted clones | |
| 1A1 | 47.9 |
| 1B6 | 57.2 |
| 1C5 | 188.9 |
| 1D1 | 151.0 |
| 1D6 | 59.1 |
| 2D6 | 165.6 |
| control clones | |
| KO2 | 56.5 |
| KO6 | 34.6 |

It was observed that three of six mIgG-sorted clones (i.e. clones 1A1, 1B6, and 1D6) showed expression levels in a range comparable to the two control clones. The other three mIgG-sorted clones (i.e. clones 1C5, 1D1, and 2D6) showed a markedly elevated IgG expression that was up to 3.3 fold greater than observed in the control clones.

Example 13

Northern Blot Analysis of Selected CHO Clones

Figure 9:
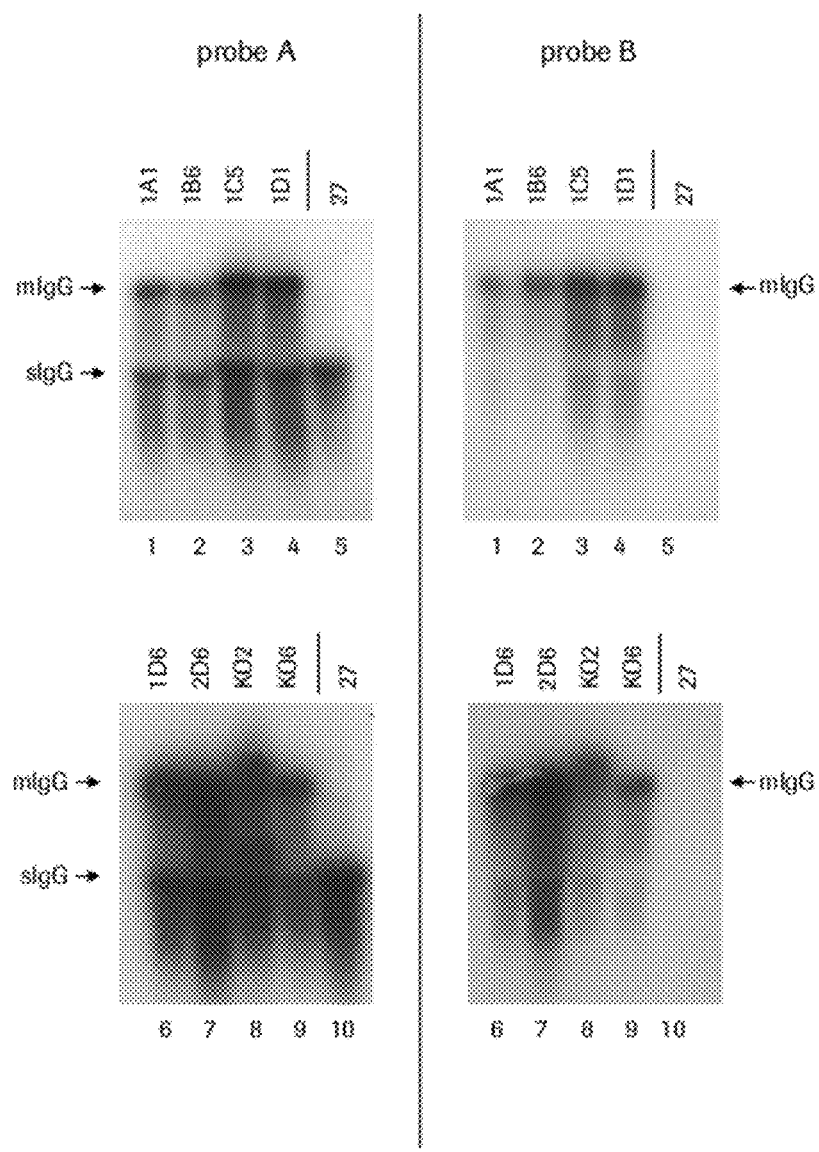
FIG. 9 Analysis of mRNA by Northern blot. Autoradiography of Northern blots hybridized with [α-$^{32}$P] labeled probe A (left panel) or probe B (right panel) as shown in FIG. 7B. In each lane 10 μg total RNA isolated from clones 1A1, 1B6, 1C5, or 1D1 (lanes 1-4), and clones 1D6, 2D6, KO2 or KO6 (lanes 6-9) was separated by denaturating agarose gel electrophoresis and transferred to a nylon membrane. Clone "27" expresses sIgG only and was added for control (lanes 5, 10). The heavy chain mRNAs of the mIgG and the sIgG isoform are indicated.

The six mIgG-sorted clones and the two control clones adapted to growth in shaker flasks (see example 12) were analyzed by Northern blot to define the ratio between the two heavy chain isoforms that emerge by alternative splicing of the primary transcript. For comparison the clone '27' was analyzed in parallel. This clone has been obtained by stable transfection of CHO-K1 cells with a genomically organized expression vector for only the secreted form of the identical antibody. The Northern blot was performed as described in example 6 in detail and is shown in FIG. 9.

Example 14

Construction of the sIgG/IgG-GPI Expression Vector 'pIgG-GPI-B'

For plasma membrane anchoring of an immunoglobulin the native transmembrane domain encoded by the 3' part of exon M1 and the intracellular region encoded by exon M2 are replaced by the carboxy-terminal signal peptide of the human placental alkaline phosphatase which mediates glycosylphosphatidylinositol (GPI) anchoring. Therefore the DNA sequence in plasmid pmIgGΔ-B (see example 1c) encoding the following 53 amino acids

LWTTITIFITLFLLSVCYSATVTFFKV    (SEQ ID NO: 146)
KWIFSSVVDLKQTIVPDYRNMIRQGA is replaced by the DNA sequence coding for the following amino acid sequence of the carboxy-terminal signal peptide of the human placental alkaline phosphatase (NCBI accession: M13077; nucleotides: 1542-1643)

(SEQ ID NO: 147)
AGTTDAAHPGRSVVPALLPLLAGTLLLLETATAP.

The nucleic acid sequence of the gamma-chain expression cassette constant region, from CH1 to 3'UTR of expression plasmid pIgG-GPI-B is given in SEQ ID NO: 148.

The corresponding amino acid sequence of the sIgG isoform of the gamma-chain constant region encoded by plasmid pIgG-GPI-B is given in SEQ ID NO: 149.

The corresponding amino acid sequence of the long isoform of the gamma-chain constant region including the carboxy-terminal signal peptide of the human placental alkaline phosphatase encoded by plasmid pIgG-GPI-B is given in SEQ ID NO: 150.

Figure 10:
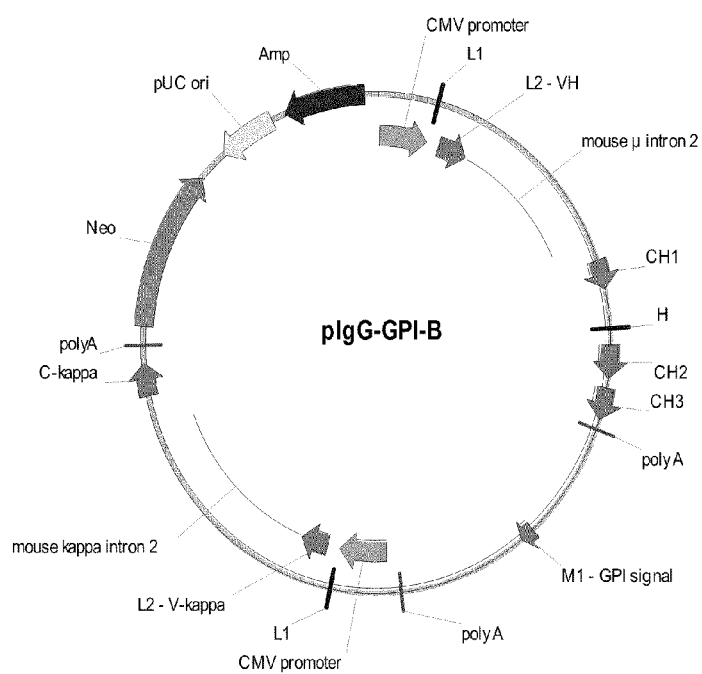
FIG. 10 Plasmid card of the sIgG/IgG-GPI expression vector pIgG-GPI-B.

This plasmid allows for the expression of the secreted form (sIgG) and a GPI-anchored form of an antibody by alternative splicing of the heavy chain pre-mRNA (see FIG. 10).

---

The invention claimed is:

1. A nucleic acid comprising in a 5' to 3' direction
   a) a first nucleic acid encoding an immunoglobulin heavy chain without an in frame stop codon at its 3' terminus,
   b) a second nucleic acid beginning with a 5' splice donor site and terminated by a 3' splice acceptor site comprising an in frame translational stop codon and a polyadenylation signal of a human or mouse immunoglobulin α, ε, γ and µ heavy chain, and
   c) a third nucleic acid encoding at least 60% of a complete human immunoglobulin transmembrane domain,
   wherein said immunoglobulin heavy chain and a marker are expressed from the same nucleic acid, wherein the marker is a plasma-membrane bound form of the expressed immunoglobulin heavy chain.

2. The nucleic acid of claim 1, characterized in that said second nucleic acid comprises only one 5' splice donor site and only one 3' splice acceptor site.

3. The nucleic acid of claim 2, characterized in that said second nucleic acid is a germline-derived immunoglobulin heavy chain intron, wherein in said intron 50 consecutive nucleotides are deleted.

4. The nucleic acid of claim 1, characterized in that said first nucleic acid encodes an human immunoglobulin heavy chain comprising all exons and all but one intron of the genomically organized immunoglobulin heavy chain gene.

5. An isolated eukaryotic cell comprising a nucleic acid according to claim 1.

6. The eukaryotic cell according to claim 5, characterized in that said eukaryotic cell is selected from the group consisting of CHO cells, NSO cells, Sp2/0 cells, COS cells, K562 cells, BHK cells, PER.C6® cells, and HEK cells.

7. A method for selecting a eukaryotic cell expressing an immunoglobulin heavy chain, whereby the method comprises
   a) transfecting a eukaryotic cell with a nucleic acid comprising in a 5' to 3' direction
      i) a first nucleic acid encoding a immunoglobulin heavy chain without an in frame translational stop codon,
      ii) a second nucleic acid beginning with a splice donor site and terminated by a splice acceptor site comprising an in frame translational stop codon and a polyadenylation signal,
      iii) a third nucleic acid encoding at least 60% of a complete immunoglobulin transmembrane domain,
   b) culturing of said transfected cell under conditions suitable for the production of pre-mRNA from said nucleic acid, processing of said pre-MRNA, and translation of said processed mRNA into a polypeptide, wherein said transfected cell produces soluble immunoglobulin heavy chain and plasma-membrane-bound immunoglobulin heavy chain by alternative splicing of said pre-mRNA, and c) selecting a cell with plasma-membrane-bound immunoglobulin heavy chain to be said cell expressing an immunoglobulin heavy chain.

8. The method of claim 7, characterized in that i) said first nucleic acid encodes at least 60% of an immunoglobulin heavy chain $C_H3$ or $C_H4$ domain, ii) said second nucleic acid is beginning with the 5' splice donor site of an immunoglobulin heavy chain $C_H3$ or $C_H4$ domain exon and is terminated by the 3' splice acceptor site of the immunoglobulin heavy chain transmembrane domain exon M1, iii) said third nucleic acid comprises at least 60% of an immunoglobulin transmembrane domain.

9. The method of claim 7, characterized in that said second nucleic acid is obtained from the nucleic acid encoding a polypeptide or protein selected from the group consisting of the C3b/C4b receptor; human, chicken, and rat EGFR; FGFR; human and mouse immunoglobulin α, ε, γ. μ heavy chain; human $PLA_2$ receptor; chicken Cek5; and mouse leukemia inhibitory factor receptor α-chain.

10. The method of claim 7, characterized in that only one intron of the produced pre-mRNA can be spliced alternatively.

11. The method of claim 10, characterized in that said selecting a cell is performed by a method selected from the group consisting_of flow cytometry, ELISA, immunoprecipitation, immunoaffinity column chromatography, magnetic bead imunoafflinity sorting, microscopy-based isolation methods, or immunological binding.

12. The method of claim 11, characterized in that the 5' splice site is an alternatively spliceable nucleic acid, resulting in a molecular ratio of soluble polypeptide to plasma-membrane-bound polypeptide of from more than 50:50 to less than 100:0.

* * * * *

UNITED STATES PATENT AND TRADEMARK OFFICE
CERTIFICATE OF CORRECTION

PATENT NO. : 8,354,516 B2  Page 1 of 1
APPLICATION NO. : 12/299918
DATED : January 15, 2013
INVENTOR(S) : Endl et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 299 days.

Signed and Sealed this
First Day of September, 2015

Michelle K. Lee
*Director of the United States Patent and Trademark Office*